United States Patent
Latham et al.

(10) Patent No.: US 10,324,141 B2
(45) Date of Patent: Jun. 18, 2019

(54) PACKAGES FOR COIL ACTUATED POSITION SENSORS

(71) Applicant: Allegro MicroSystems, LLC, Manchester, NH (US)

(72) Inventors: Alexander Latham, Harvard, MA (US); Michael C. Doogue, Bedford, NH (US); Jason Boudreau, Exeter, NH (US)

(73) Assignee: Allegro MicroSystems, LLC, Manchester, NH (US)

( * ) Notice: Subject to any disclaimer, the term of this patent is extended or adjusted under 35 U.S.C. 154(b) by 46 days.

(21) Appl. No.: 15/606,262

(22) Filed: May 26, 2017

(65) Prior Publication Data

US 2018/0340987 A1 Nov. 29, 2018

(51) Int. Cl.
*G01R 33/09* (2006.01)
*G01R 33/12* (2006.01)
*G01R 35/00* (2006.01)
*G01D 5/14* (2006.01)
*G01D 5/20* (2006.01)
(Continued)

(52) U.S. Cl.
CPC ......... *G01R 33/0094* (2013.01); *G01N 27/90* (2013.01); *G01R 33/0005* (2013.01); *G01R 33/0011* (2013.01); *G01R 33/0017* (2013.01); *G01R 33/0029* (2013.01); *G01R 33/025* (2013.01); *G01R 33/032* (2013.01); *G01R 33/1284* (2013.01); *H01F 5/003* (2013.01); *H01F 2027/348* (2013.01)

(58) Field of Classification Search
CPC ...... G01R 33/00; G01R 33/02; G01R 33/025; G01R 33/09; G01R 33/12; G01R 35/00; G01D 5/14; G01D 5/20; G01N 27/72; G01N 27/82; H01F 5/04
See application file for complete search history.

(56) References Cited

U.S. PATENT DOCUMENTS 3,132,337 A 5/1964 Martin
3,195,043 A 7/1965 Burig et al.
(Continued)

FOREIGN PATENT DOCUMENTS

CH 683 469 A5 3/1994
DE 25 18 054 11/1976
(Continued)

OTHER PUBLICATIONS

U.S. Appl. No. 15/606,332, filed May 26, 2017, Latham et al.
(Continued)

*Primary Examiner* — Neel D Shah
(74) *Attorney, Agent, or Firm* — Daly, Crowley, Mofford & Durkee, LLP

(57) ABSTRACT

An apparatus comprises one or more substrates and one or more coils. At least one of the coils is configured to produce a first magnetic field that induces eddy currents in a conductive target, which generates a reflected magnetic field. One or more magnetic field sensing elements supported by the one or more substrates detect the reflected magnetic field. A conductive support structure supports the one or more substrates. The support structure includes a gap in an area adjacent to the one or more coils so that the support structure does not generate a reflected magnetic field in response to the first magnetic field.

15 Claims, 38 Drawing Sheets

(51) Int. Cl.
  *G01N 27/72*   (2006.01)
  *G01N 27/82*   (2006.01)
  *H01F 5/04*    (2006.01)
  *G01R 33/00*   (2006.01)
  *G01R 33/025*  (2006.01)
  *G01R 33/032*  (2006.01)
  *G01N 27/90*   (2006.01)
  *H01F 5/00*    (2006.01)
  *H01F 27/34*   (2006.01)

(56) References Cited

U.S. PATENT DOCUMENTS

| | | | |
|---|---|---|---|
| 3,281,628 A | 10/1966 | Bauer et al. | |
| 3,607,528 A | 9/1971 | Gassaway | |
| 3,611,138 A | 10/1971 | Winebrener | |
| 3,661,061 A | 5/1972 | Tokarz | |
| 3,728,786 A | 4/1973 | Lucas et al. | |
| 4,048,670 A | 9/1977 | Eysermans | |
| 4,188,605 A | 2/1980 | Stout | |
| 4,204,317 A | 5/1980 | Winn | |
| 4,236,832 A | 12/1980 | Komatsu et al. | |
| 4,283,643 A | 8/1981 | Levin | |
| 4,315,523 A | 2/1982 | Mahawili et al. | |
| 4,438,347 A | 3/1984 | Gehring | |
| 4,573,258 A | 3/1986 | Io et al. | |
| 4,614,111 A | 9/1986 | Wolff | |
| 4,649,796 A | 3/1987 | Schmidt | |
| 4,670,715 A | 6/1987 | Fuzzell | |
| 4,703,378 A | 10/1987 | Imakoshi et al. | |
| 4,719,419 A | 1/1988 | Dawley | |
| 4,733,455 A | 3/1988 | Nakamura et al. | |
| 4,745,363 A | 5/1988 | Carr et al. | |
| 4,746,859 A | 5/1988 | Malik | |
| 4,752,733 A | 6/1988 | Petr et al. | |
| 4,758,943 A | 7/1988 | Aström et al. | |
| 4,760,285 A | 7/1988 | Nelson | |
| 4,764,767 A | 8/1988 | Ichikawa et al. | |
| 4,769,344 A | 9/1988 | Sakai et al. | |
| 4,772,929 A | 9/1988 | Manchester | |
| 4,789,826 A | 12/1988 | Willett | |
| 4,796,354 A | 1/1989 | Yokoyama et al. | |
| 4,823,075 A | 4/1989 | Alley | |
| 4,833,406 A | 5/1989 | Foster | |
| 4,893,027 A | 1/1990 | Kammerer et al. | |
| 4,908,685 A | 3/1990 | Shibasaki et al. | |
| 4,910,861 A | 3/1990 | Dohogne | |
| 4,935,698 A | 6/1990 | Kawaji et al. | |
| 4,944,028 A | 7/1990 | Iijima et al. | |
| 4,954,777 A | 9/1990 | Klopfer et al. | |
| 4,970,411 A | 11/1990 | Halg et al. | |
| 4,983,916 A | 1/1991 | Iijima et al. | |
| 5,012,322 A | 4/1991 | Guillotte et al. | |
| 5,021,493 A | 6/1991 | Sandstrom | |
| 5,028,868 A | 7/1991 | Murata et al. | |
| 5,045,920 A | 9/1991 | Vig et al. | |
| 5,078,944 A | 1/1992 | Yoshino | |
| 5,084,289 A | 1/1992 | Shin et al. | |
| 5,121,289 A | 6/1992 | Gagliardi | |
| 5,137,677 A | 8/1992 | Murata | |
| 5,139,973 A | 8/1992 | Nagy et al. | |
| 5,167,896 A | 12/1992 | Hirota et al. | |
| 5,185,919 A | 2/1993 | Hickey | |
| 5,196,794 A | 3/1993 | Murata | |
| 5,200,698 A | 4/1993 | Thibaud | |
| 5,210,493 A | 5/1993 | Schroeder et al. | |
| 5,216,405 A | 6/1993 | Schroeder et al. | |
| 5,244,834 A | 9/1993 | Suzuki et al. | |
| 5,247,202 A | 9/1993 | Popovic et al. | |
| 5,247,278 A | 9/1993 | Pant et al. | |
| 5,250,925 A | 10/1993 | Shinkle | |
| 5,286,426 A | 2/1994 | Rano, Jr. et al. | |
| 5,289,344 A | 2/1994 | Gagnon et al. | |
| 5,315,245 A | 5/1994 | Schroeder et al. | |
| 5,329,416 A | 7/1994 | Ushiyama et al. | |
| 5,332,956 A | 7/1994 | Oh | |
| 5,332,965 A | 7/1994 | Wolf et al. | |
| 5,399,968 A | 3/1995 | Sheppard et al. | |
| 5,412,255 A | 5/1995 | Wallrafen | |
| 5,414,355 A | 5/1995 | Davidson et al. | |
| 5,424,558 A | 6/1995 | Borden et al. | |
| 5,432,444 A | 7/1995 | Yasohama et al. | |
| 5,434,105 A | 7/1995 | Liou | |
| 5,453,727 A | 9/1995 | Shibasaki et al. | |
| 5,469,058 A | 11/1995 | Dunnam | |
| 5,479,695 A | 1/1996 | Grader et al. | |
| 5,486,759 A | 1/1996 | Seiler et al. | |
| 5,488,294 A | 1/1996 | Liddell et al. | |
| 5,491,633 A | 2/1996 | Henry et al. | |
| 5,497,081 A | 3/1996 | Wolf et al. | |
| 5,500,589 A | 3/1996 | Sumcad | |
| 5,500,994 A | 3/1996 | Itaya | |
| 5,508,611 A | 4/1996 | Schroeder et al. | |
| 5,521,501 A | 5/1996 | Dettmann et al. | |
| 5,545,983 A | 8/1996 | Okeya et al. | |
| 5,551,146 A | 9/1996 | Kawabata et al. | |
| 5,581,170 A | 12/1996 | Mammano et al. | |
| 5,581,179 A | 12/1996 | Engel et al. | |
| 5,596,272 A | 1/1997 | Busch | |
| 5,621,319 A | 4/1997 | Bilotti et al. | |
| 5,627,315 A | 5/1997 | Figi et al. | |
| 5,631,557 A | 5/1997 | Davidson | |
| 5,640,090 A | 6/1997 | Furuya et al. | |
| 5,691,637 A | 11/1997 | Oswald et al. | |
| 5,696,790 A | 12/1997 | Graham et al. | |
| 5,712,562 A | 1/1998 | Berg | |
| 5,714,102 A | 2/1998 | Highum et al. | |
| 5,719,496 A | 2/1998 | Wolf | |
| 5,729,128 A | 3/1998 | Bunyer et al. | |
| 5,757,181 A | 5/1998 | Wolf et al. | |
| 5,781,005 A | 7/1998 | Vig et al. | |
| 5,789,658 A | 8/1998 | Henn et al. | |
| 5,789,915 A | 8/1998 | Ingraham | |
| 5,796,249 A | 8/1998 | Andräet et al. | |
| 5,818,222 A | 10/1998 | Ramsden | |
| 5,818,223 A | 10/1998 | Wolf | |
| 5,839,185 A | 11/1998 | Smith et al. | |
| 5,841,276 A | 11/1998 | Makino et al. | |
| 5,859,387 A | 1/1999 | Gagnon | |
| 5,883,567 A | 3/1999 | Mullins, Jr. | |
| 5,886,070 A | 3/1999 | Honkura et al. | |
| 5,896,030 A | 4/1999 | Hasken | |
| 5,912,556 A | 6/1999 | Frazee et al. | |
| 5,963,028 A | 10/1999 | Engel et al. | |
| 6,011,770 A | 1/2000 | Tan | |
| 6,016,055 A | 1/2000 | Jager et al. | |
| 6,043,644 A | 3/2000 | de Coulon et al. | |
| 6,043,646 A | 3/2000 | Jansseune | |
| 6,064,198 A | 5/2000 | Wolf et al. | |
| 6,136,250 A | 10/2000 | Brown | |
| 6,150,809 A * | 11/2000 | Tiernan | G01N 27/82 |
| | | | 324/225 |
| 6,169,396 B1 | 1/2001 | Yokotani et al. | |
| 6,175,233 B1 | 1/2001 | McCurley et al. | |
| 6,180,041 B1 | 1/2001 | Takizawa | |
| 6,184,679 B1 | 2/2001 | Popovic et al. | |
| 6,198,373 B1 | 3/2001 | Ogawa et al. | |
| 6,242,604 B1 | 6/2001 | Hudlicky et al. | |
| 6,242,904 B1 | 6/2001 | Shirai et al. | |
| 6,242,905 B1 | 6/2001 | Draxelmayr | |
| 6,265,865 B1 | 7/2001 | Engel et al. | |
| 6,278,269 B1 | 8/2001 | Vig et al. | |
| 6,297,627 B1 | 10/2001 | Towne et al. | |
| 6,339,322 B1 | 1/2002 | Loreck et al. | |
| 6,351,506 B1 | 2/2002 | Lewicki | |
| 6,356,068 B1 | 3/2002 | Steiner et al. | |
| 6,392,478 B1 | 5/2002 | Mulder et al. | |
| 6,429,640 B1 | 8/2002 | Daughton et al. | |
| 6,436,748 B1 | 8/2002 | Forbes et al. | |
| 6,437,558 B2 | 8/2002 | Li et al. | |
| 6,452,381 B1 | 9/2002 | Nakatani et al. | |
| 6,462,536 B1 | 10/2002 | Mednikov et al. | |
| 6,492,804 B2 | 12/2002 | Tsuge et al. | |
| 6,501,270 B1 | 12/2002 | Opie | |

(56) References Cited

U.S. PATENT DOCUMENTS

| | | |
|---|---|---|
| 6,504,363 B1 | 1/2003 | Dogaru et al. |
| 6,525,531 B2 | 2/2003 | Forrest et al. |
| 6,528,992 B2 | 3/2003 | Shinjo et al. |
| 6,542,847 B1 | 4/2003 | Lohberg et al. |
| 6,545,332 B2 | 4/2003 | Huang |
| 6,545,457 B2 | 4/2003 | Goto et al. |
| 6,545,462 B2 | 4/2003 | Schott et al. |
| 6,566,872 B1 | 5/2003 | Sugitani |
| 6,640,451 B1 | 11/2003 | Vinarcik |
| 6,653,968 B1 | 11/2003 | Schneider |
| 6,674,679 B1 | 1/2004 | Perner et al. |
| 6,687,644 B1 | 2/2004 | Zinke et al. |
| 6,692,676 B1 | 2/2004 | Vig et al. |
| 6,707,298 B2 | 3/2004 | Suzuki et al. |
| 6,759,843 B2 | 7/2004 | Furlong |
| 6,770,163 B1 | 8/2004 | Kuah et al. |
| 6,781,233 B2 | 8/2004 | Zverev et al. |
| 6,781,359 B2 | 8/2004 | Stauth et al. |
| 6,798,193 B2 | 9/2004 | Zimmerman et al. |
| 6,815,944 B2 | 11/2004 | Vig et al. |
| 6,822,443 B1 | 11/2004 | Dogaru |
| 6,853,178 B2 | 2/2005 | Hayat-Dawoodi |
| 6,896,407 B2 | 5/2005 | Nomiyama et al. |
| 6,902,951 B2 | 6/2005 | Goller et al. |
| 6,917,321 B1 | 7/2005 | Haurie et al. |
| 6,956,366 B2 | 10/2005 | Butzmann |
| 7,023,205 B1 | 4/2006 | Krupp |
| 7,026,808 B2 | 4/2006 | Vig et al. |
| 7,031,170 B2 | 4/2006 | Daeche et al. |
| 7,038,448 B2 | 5/2006 | Schott et al. |
| 7,049,924 B2 | 5/2006 | Hayashi et al. |
| 7,112,955 B2 | 9/2006 | Buchhold |
| 7,112,957 B2 | 9/2006 | Bicking |
| 7,126,327 B1 | 10/2006 | Busch |
| 7,132,825 B2 | 11/2006 | Martin |
| 7,190,784 B2 | 3/2007 | Li |
| 7,193,412 B2 | 3/2007 | Freeman |
| 7,199,579 B2 | 4/2007 | Scheller et al. |
| 7,259,545 B2 | 8/2007 | Stauth et al. |
| 7,265,531 B2 | 9/2007 | Stauth et al. |
| 7,269,992 B2 | 9/2007 | Lamb et al. |
| 7,285,952 B1 | 10/2007 | Hatanaka et al. |
| 7,292,095 B2 | 11/2007 | Burt et al. |
| 7,295,000 B2 | 11/2007 | Werth |
| 7,319,319 B2 | 1/2008 | Jones et al. |
| 7,323,780 B2 | 1/2008 | Daubenspeck et al. |
| 7,323,870 B2 | 1/2008 | Tatschl et al. |
| 7,325,175 B2 | 1/2008 | Momtaz |
| 7,345,468 B2 | 3/2008 | Okada et al. |
| 7,355,388 B2 | 4/2008 | Ishio |
| 7,361,531 B2 | 4/2008 | Sharma et al. |
| 7,362,094 B2 | 4/2008 | Voisine et al. |
| 7,365,530 B2 | 4/2008 | Bailey et al. |
| 7,385,394 B2 | 6/2008 | Auburger et al. |
| 7,425,821 B2 | 9/2008 | Monreal et al. |
| 7,474,093 B2 | 1/2009 | Ausserlechner |
| 7,476,953 B2 | 1/2009 | Taylor et al. |
| 7,518,354 B2 | 4/2009 | Stauth et al. |
| 7,592,801 B2 | 9/2009 | Bailey et al. |
| 7,598,601 B2 | 10/2009 | Taylor et al. |
| 7,605,647 B1 | 10/2009 | Romero et al. |
| 7,635,993 B2 | 12/2009 | Boeve |
| 7,694,200 B2 | 4/2010 | Forrest et al. |
| 7,701,208 B2 | 4/2010 | Nishikawa |
| 7,705,586 B2 | 4/2010 | Van Zon et al. |
| 7,729,675 B2 | 6/2010 | Krone |
| 7,746,056 B2 | 6/2010 | Stauth et al. |
| 7,746,065 B2 | 6/2010 | Pastre et al. |
| 7,764,118 B2 | 7/2010 | Kusuda et al. |
| 7,768,083 B2 | 8/2010 | Doogue et al. |
| 7,769,110 B2 | 8/2010 | Momtaz |
| 7,800,389 B2 | 9/2010 | Friedrich et al. |
| 7,808,074 B2 | 10/2010 | Knittl |
| 7,816,772 B2 | 10/2010 | Engel et al. |
| 7,816,905 B2 | 10/2010 | Doogue et al. |
| 7,839,141 B2 | 11/2010 | Werth et al. |
| 7,923,996 B2 | 4/2011 | Doogue et al. |
| 7,936,144 B2 | 5/2011 | Vig et al. |
| 7,956,604 B2 | 6/2011 | Ausserlechner |
| 7,961,823 B2 | 6/2011 | Kolze et al. |
| 7,982,454 B2 | 7/2011 | Fernandez et al. |
| 7,990,209 B2 | 8/2011 | Romero |
| 8,030,918 B2 | 10/2011 | Doogue et al. |
| 8,058,870 B2 | 11/2011 | Sterling |
| 8,063,631 B2 | 11/2011 | Fermon et al. |
| 8,063,634 B2 | 11/2011 | Sauber et al. |
| 8,080,993 B2 | 12/2011 | Theuss et al. |
| 8,106,654 B2 | 1/2012 | Theuss et al. |
| 8,128,549 B2 | 3/2012 | Testani et al. |
| 8,134,358 B2 | 3/2012 | Charlier et al. |
| 8,143,169 B2 | 3/2012 | Engel et al. |
| 8,253,210 B2 | 8/2012 | Theuss et al. |
| 8,274,279 B2 | 9/2012 | Gies |
| 8,299,783 B2 | 10/2012 | Fernandez et al. |
| 8,362,579 B2 | 1/2013 | Theuss et al. |
| 8,447,556 B2 | 5/2013 | Friedrich et al. |
| 8,461,677 B2 | 6/2013 | Ararao et al. |
| 8,486,755 B2 | 7/2013 | Ararao et al. |
| 8,542,010 B2 | 9/2013 | Cesaretti et al. |
| 8,577,634 B2 | 11/2013 | Donovan et al. |
| 8,610,430 B2 | 12/2013 | Werth et al. |
| 8,624,588 B2 | 1/2014 | Vig et al. |
| 8,629,520 B2 | 1/2014 | Doogue et al. |
| 8,629,539 B2 | 1/2014 | Milano et al. |
| 8,680,846 B2 | 3/2014 | Cesaretti et al. |
| 8,680,848 B2 | 3/2014 | Foletto et al. |
| 8,754,640 B2 | 6/2014 | Vig et al. |
| 8,773,124 B2 | 7/2014 | Ausserlechner |
| 9,081,041 B2 | 7/2015 | Friedrich et al. |
| 9,116,018 B2 | 8/2015 | Frachon |
| 9,164,156 B2 | 10/2015 | Elian et al. |
| 9,201,122 B2 | 12/2015 | Cesaeretti et al. |
| 9,201,123 B2 | 12/2015 | Elian et al. |
| 9,228,860 B2 | 1/2016 | Sharma et al. |
| 9,411,025 B2 | 8/2016 | David et al. |
| 9,494,660 B2 | 11/2016 | David et al. |
| 9,664,494 B2 | 5/2017 | Fernandez et al. |
| 2001/0002791 A1 | 6/2001 | Tsuge et al. |
| 2001/0009367 A1 | 7/2001 | Seitzer et al. |
| 2002/0027488 A1 | 3/2002 | Hayat-Dawoodi et al. |
| 2002/0084923 A1 | 7/2002 | Li |
| 2003/0001563 A1 | 1/2003 | Turner |
| 2003/0038675 A1 | 2/2003 | Gailus et al. |
| 2003/0062891 A1 | 4/2003 | Slates |
| 2003/0102909 A1 | 6/2003 | Motz |
| 2003/0222642 A1 | 12/2003 | Butzmann |
| 2003/0227286 A1 | 12/2003 | Dunisch et al. |
| 2004/0021461 A1 | 2/2004 | Goldfine et al. |
| 2004/0032251 A1 | 2/2004 | Zimmerman et al. |
| 2004/0046248 A1 | 3/2004 | Waelti et al. |
| 2004/0062362 A1 | 4/2004 | Matsuya |
| 2004/0080314 A1 | 4/2004 | Tsujii et al. |
| 2004/0135220 A1 | 7/2004 | Goto |
| 2004/0174164 A1 | 9/2004 | Ao |
| 2004/0184196 A1 | 9/2004 | Jayasekara |
| 2004/0196045 A1 | 10/2004 | Larsen |
| 2005/0017709 A1 | 1/2005 | Stolfus et al. |
| 2005/0120782 A1 | 6/2005 | Kishibata et al. |
| 2005/0122095 A1 | 6/2005 | Dooley |
| 2005/0122099 A1 | 6/2005 | Imamoto et al. |
| 2005/0167790 A1 | 8/2005 | Khor et al. |
| 2005/0179429 A1 | 8/2005 | Lohberg |
| 2005/0225318 A1 | 10/2005 | Bailey et al. |
| 2005/0280411 A1 | 12/2005 | Bicking |
| 2006/0033487 A1 | 2/2006 | Nagano et al. |
| 2006/0038559 A1 | 2/2006 | Lamb et al. |
| 2006/0068237 A1 | 3/2006 | Murphy et al. |
| 2006/0097717 A1 | 5/2006 | Tokuhara et al. |
| 2006/0125473 A1 | 6/2006 | Frachon et al. |
| 2006/0181263 A1 | 8/2006 | Doogue et al. |
| 2006/0202692 A1 | 9/2006 | Tatschl et al. |
| 2006/0261801 A1 | 11/2006 | Busch |
| 2007/0110199 A1 | 5/2007 | Momtaz et al. |
| 2007/0114992 A1 | 5/2007 | Muniraju et al. |

(56) References Cited

U.S. PATENT DOCUMENTS

| | | |
|---|---|---|
| 2007/0170533 A1 | 7/2007 | Doogue et al. |
| 2007/0247141 A1 | 10/2007 | Pastre et al. |
| 2007/0285089 A1 | 12/2007 | Ibuki et al. |
| 2008/0013298 A1 | 1/2008 | Sharma et al. |
| 2008/0137784 A1 | 6/2008 | Krone |
| 2008/0237818 A1 | 10/2008 | Engel et al. |
| 2008/0238410 A1 | 10/2008 | Charlier et al. |
| 2008/0270067 A1 | 10/2008 | Eriksen et al. |
| 2009/0001964 A1 | 1/2009 | Strzalkowski |
| 2009/0009163 A1 | 1/2009 | Yamada |
| 2009/0058404 A1 | 3/2009 | Kurumado |
| 2009/0085706 A1 | 4/2009 | Baarman et al. |
| 2009/0102467 A1 | 4/2009 | Snell et al. |
| 2009/0140725 A1 | 6/2009 | Ausserlechner |
| 2009/0146647 A1 | 6/2009 | Ausserlechner |
| 2009/0152696 A1 | 6/2009 | Dimasacat et al. |
| 2009/0167298 A1 | 7/2009 | Kreutzbruck et al. |
| 2009/0168286 A1 | 7/2009 | Berkley et al. |
| 2009/0206831 A1 | 8/2009 | Fermon et al. |
| 2009/0243601 A1 | 10/2009 | Feldtkeller |
| 2009/0251134 A1 | 10/2009 | Uenoyama |
| 2009/0315543 A1 | 12/2009 | Guo et al. |
| 2010/0033175 A1 | 2/2010 | Boeve et al. |
| 2010/0052667 A1 | 3/2010 | Kohama et al. |
| 2010/0072988 A1 | 3/2010 | Hammerschmidt et al. |
| 2010/0188078 A1 | 7/2010 | Foletto et al. |
| 2010/0201356 A1 | 8/2010 | Koller et al. |
| 2010/0276769 A1 | 11/2010 | Theuss et al. |
| 2010/0295140 A1 | 11/2010 | Theuss et al. |
| 2011/0018533 A1 | 1/2011 | Cesaretti et al. |
| 2011/0031960 A1 | 2/2011 | Hohe et al. |
| 2011/0127998 A1 | 6/2011 | Elian et al. |
| 2011/0133732 A1 | 6/2011 | Sauber |
| 2011/0267040 A1 | 11/2011 | Frachon |
| 2011/0285384 A1 | 11/2011 | Nomura |
| 2012/0019236 A1 | 1/2012 | Tiernan et al. |
| 2012/0062215 A1 | 3/2012 | Ide et al. |
| 2013/0113474 A1 | 5/2013 | Elian |
| 2013/0214777 A1 | 8/2013 | Itoi |
| 2013/0241543 A1 | 9/2013 | Stenson et al. |
| 2013/0249029 A1 | 9/2013 | Vig et al. |
| 2013/0249544 A1 | 9/2013 | Vig et al. |
| 2013/0278246 A1 | 10/2013 | Stegerer et al. |
| 2013/0285970 A1* | 10/2013 | Ahn .................. G06F 3/044 345/173 |
| 2013/0300401 A1 | 11/2013 | Krapf et al. |
| 2013/0300406 A1 | 11/2013 | Pepka et al. |
| 2014/0327435 A1 | 11/2014 | Rohrer |
| 2015/0022187 A1 | 1/2015 | Taylor et al. |
| 2015/0022193 A1 | 1/2015 | Burdette et al. |
| 2015/0022197 A1 | 1/2015 | David et al. |
| 2015/0022198 A1 | 1/2015 | David et al. |
| 2015/0048390 A1* | 2/2015 | Imazu ................ H01L 25/0756 257/88 |
| 2016/0123771 A1 | 5/2016 | David et al. |

FOREIGN PATENT DOCUMENTS

| | | |
|---|---|---|
| DE | 40 31 560 A | 4/1992 |
| DE | 195 39 458 A1 | 4/1997 |
| DE | 196 34 715 A1 | 3/1998 |
| DE | 196 50 935 A1 | 6/1998 |
| DE | 198 38 433 | 3/1999 |
| DE | 198 51 839 A1 | 11/1999 |
| DE | 199 61 504 A1 | 6/2001 |
| DE | 102 10 184 | 9/2003 |
| DE | 103 14 602 A1 | 10/2004 |
| DE | 10 2006 037 226 A1 | 2/2008 |
| DE | 10 2007 018 238 A1 | 10/2008 |
| DE | 10 2007 041 230 B3 | 4/2009 |
| DE | 10 2010 016 584 | 11/2010 |
| DE | 10 2011 102483 | 11/2012 |
| EP | 0 289 414 A2 | 11/1988 |
| EP | 0 289 414 A3 | 11/1988 |
| EP | 0 357 013 A2 | 3/1990 |
| EP | 0 357 013 A3 | 3/1990 |
| EP | 0 361 456 A2 | 4/1990 |
| EP | 0 361 456 A3 | 4/1990 |
| EP | 0629834 A1 | 12/1994 |
| EP | 0 680 103 A1 | 11/1995 |
| EP | 0 898 180 A2 | 2/1999 |
| EP | 0 944 888 B1 | 10/2001 |
| EP | 1306687 A2 | 5/2003 |
| EP | 1 443 332 A1 | 8/2004 |
| EP | 1 580 560 A1 | 9/2005 |
| EP | 1 637 898 A1 | 3/2006 |
| EP | 1 662 353 A1 | 5/2006 |
| EP | 1 679 524 A1 | 7/2006 |
| EP | 1 850 143 A1 | 10/2007 |
| EP | 2 063 229 | 5/2009 |
| EP | 1797496 | 7/2009 |
| EP | 2402719 | 1/2012 |
| EP | 3 139 190 A1 | 8/2017 |
| FR | 2 748 105 A1 | 10/1997 |
| FR | 2 909 756 | 6/2008 |
| GB | 2135060 A | 8/1984 |
| GB | 2276727 A | 10/1994 |
| GB | 2 481 482 | 12/2011 |
| JP | S5771504 A | 5/1982 |
| JP | S60182503 A | 9/1985 |
| JP | 61-48777 | 3/1986 |
| JP | 363 084176 A | 4/1988 |
| JP | 63-263782 | 10/1988 |
| JP | 63-300911 | 12/1988 |
| JP | H02-116753 | 5/1990 |
| JP | H03-29817 | 2/1991 |
| JP | H0335182 A | 2/1991 |
| JP | H04-095817 | 3/1992 |
| JP | H06-273437 | 9/1994 |
| JP | 08-097486 | 4/1996 |
| JP | H08-511348 A | 11/1996 |
| JP | 09-166612 | 6/1997 |
| JP | 10-332725 | 12/1998 |
| JP | H10-318784 A | 12/1998 |
| JP | 11-064363 | 3/1999 |
| JP | 11-074142 | 3/1999 |
| JP | 2000-183241 | 6/2000 |
| JP | 2001-043475 A | 2/2001 |
| JP | 2001-141738 | 5/2001 |
| JP | 2001-165702 A | 6/2001 |
| JP | 2001-1659951 | 6/2001 |
| JP | 2002-117500 A | 4/2002 |
| JP | 2002-149013 A | 5/2002 |
| JP | 2002-357920 A | 12/2002 |
| JP | 2003-177171 | 6/2003 |
| JP | 2003-202365 A | 7/2003 |
| JP | 2004-055932 | 2/2004 |
| JP | 2004-093381 | 3/2004 |
| JP | 2004-152688 | 5/2004 |
| JP | 2004-356338 A | 12/2004 |
| JP | 2004-357858 A | 12/2004 |
| JP | 2005-517928 | 6/2005 |
| JP | 2005-337866 | 12/2005 |
| JP | 2005-345302 | 12/2005 |
| JP | 2006-003096 A | 1/2006 |
| JP | 2006-3116 A | 1/2006 |
| JP | 2006-275764 | 10/2006 |
| JP | 2006-284466 A | 10/2006 |
| JP | 2007-012582 A | 1/2007 |
| JP | 2007-218799 | 8/2007 |
| JP | 2008-180550 | 8/2008 |
| JP | 2008-264569 | 11/2008 |
| JP | 2009-222524 | 10/2009 |
| JP | 2011/086479 | 4/2011 |
| JP | 2012-501446 A | 1/2012 |
| WO | WO 88/09026 | 11/1988 |
| WO | WO 1993/12403 | 6/1993 |
| WO | WO 1994/08203 | 4/1994 |
| WO | WO 94/29672 A1 | 12/1994 |
| WO | WO 1995/18982 | 7/1995 |
| WO | WO 96/02849 A1 | 2/1996 |
| WO | WO 1999/49322 | 9/1999 |
| WO | WO 2001/40790 A1 | 6/2001 |

(56) References Cited

FOREIGN PATENT DOCUMENTS

| WO | WO 2001/74139 A2 | 10/2001 |
|---|---|---|
| WO | WO 2001/74139 A3 | 10/2001 |
| WO | WO 2003/069358 A2 | 8/2003 |
| WO | WO 2003/069358 A3 | 8/2003 |
| WO | WO 2003/107018 A1 | 12/2003 |
| WO | WO 2004/027436 | 4/2004 |
| WO | WO 2004/072672 A1 | 8/2004 |
| WO | WO 2005/013363 A2 | 2/2005 |
| WO | WO 2005/013363 A3 | 2/2005 |
| WO | WO 2006/056829 | 6/2006 |
| WO | WO 2006/083479 | 8/2006 |
| WO | WO 2007/095971 A1 | 8/2007 |
| WO | WO 2007/138508 A1 | 12/2007 |
| WO | WO 2008/008140 A2 | 1/2008 |
| WO | WO 2008/008140 A3 | 1/2008 |
| WO | WO 2008/048379 A1 | 4/2008 |
| WO | WO 2008/121443 A1 | 10/2008 |
| WO | WO 2008/145662 A1 | 12/2008 |
| WO | WO 2009/108422 A2 | 9/2009 |
| WO | WO 2009/108422 A3 | 9/2009 |
| WO | WO 2010/014309 A1 | 2/2010 |
| WO | WO 2010/027658 A2 | 3/2010 |
| WO | WO 2010/065315 A1 | 6/2010 |
| WO | WO 2010/096367 A1 | 8/2010 |
| WO | WO 2011/011479 A1 | 1/2011 |
| WO | WO 2012/148646 A1 | 11/2012 |
| WO | WO 2013/169455 | 11/2013 |
| WO | WO 2014/105302 A1 | 7/2014 |
| WO | WO2015/058733 A1 | 4/2015 |

OTHER PUBLICATIONS

U.S. Appl. No. 15/606,325, filed May 26, 2017, Romero.
U.S. Appl. No. 15/709,739, filed Sep. 20, 2017, Pepka et al.
Japanese Office Action (with English Translation) dated Jan. 13, 2017 for Japanese Application No. 2015-511491; 14 Pages.
Ahn et al.; "A New Toroidal-Meander Type Integrated Inductor with a Multilevel Meander Magnetic Core;" IEEE Transaction on Magnetics; vol. 30; No. 1; Jan. 1, 1994; 7 pages.
Allegro "Two-Wire True Zero Speed Miniature Differential Peak-Detecting Gear Tooth Sensor;" ATS645LSH; 2004; Allegro MicroSystems, Inc., Worcester, MA 01615; 14 pages.
Allegro Microsystems, Inc., "Gear-Tooth Sensor for Automotive Applications," Aug. 3, 2001; 2 pages.
Allegro MicroSystems, Inc., Hall-Effect IC Applications Guide, http://www.allegromicro.com/en/Products/Design/an/an27701.pdf, Copyright 1987, 1997; 36 pages.
Alllegro "True Zero-Speed Low-Jitter High Accuracy Gear Tooth Sensor;" ATS625LSG; 2005; Allegro MicroSystems, Inc. Worcester, MA 01615; 21 pages.
Amendment and RCE dated Jun. 9, 2015; for U.S. Appl. No. 13/946,400; 12 pages.
Ausserlechner et al.; "Compensation of the Piezo-Hall Effect in Integrated Hall Sensors on (100)-Si;" IEEE Sensors Journal, vol. 7, No. 11; Nov. 2007; ISBN: 1530-437X; 8 pages.
Ausserlechner et al.; "Drift of Magnetic Sensitivity of Small Hall Sensors Due to Moisture Absorbed by the IC-Package;" Proceedings of IEEE Sensors, 2004; vol. 1; Oct. 24, 2004; ISBN:0-7803-8692-2; 4 pages.
Ausserlechner; "Limits of Offset Cancellation by the Principle of Spinning Current Hall Probe;" Proceedings of IEEE Sensors; Oct. 2004; 4 pages.
Ausserlechner; "The piezo-Hall effect in n-silicon for arbitrary crystal orientation;" Proceedings of IEEE Sensors; vol. 3; Oct. 24, 2004; ISBN: 0-7803-8692-2; 4 pages.
Bahreyni, et al.; "A Resonant Micromachined Magnetic Field Sensor;" IEEE Sensors Journal; vol. 7, No. 9, Sep. 2007; 9 pages.
Barrettino, et al.; "CMOS-Based Monolithic Controllers for Smart Sensors Comprising Micromembranes and Microcantilevers;" IEEE Transactions on Circuits and Systems-I Regular Papers vol. 54, No. 1; Jan. 2007; 12 pages.

Baschirotto et al.; "Development and Analysis of PCB Vector 2-D Magnetic Field Sensor System for Electronic Compass;" IEEE Sensors Journal vol. 6, No. 2; Apr. 2006; 7 pages.
Bilotti et al.; "Monolithic Magnetic Hall Sensor Using Dynamic Quadrature Offset Cancellation;" IEEE Journal of Solid-State Circuits; vol. 32, Issue 6; Jun. 1997; 8 pages.
Bowers et al., "Microfabrication and Process Integration of Powder-Based Permanent Magnets", Interdisciplinary Microsystems Group, Dept. Electrical and Computer Engineering, University of Florida, USA; Technologies for Future Micro-Nano Manufacturing Workshop, Napa, California, Aug. 8-10; 4 pages.
Communication Pursuant to Rule 161(1) and 162 EPC dated Feb. 23, 2016; for European Pat. App. No. 14742423.8; 2 pages.
Communication Pursuant to Rules 161(1) and 162 dated Nov. 12, 2015 for European Application No. 14726492.3-1560; 2 pages.
Daughton J: "Spin-dependent sensors", Proceedings of the IEEE New York, US, vol. 91. No.5 May 1, 2003; 6 pages.
Decision to Grant dated Oct. 27, 2016; for European Pat. App. No. 13722619.7; 2 pages.
Demierre, et al.; "Reference Magnetic Actuator for Self-Calibration of a Very Small Hall Sensor Array;" Sensors and Actuators A97-98; Apr. 2002; 8 pages.
Dwyer, "Back-Biased Packaging Advances (SE, SG & SH versus SA & SB)," http://www.allegromicro.com/en/Products/Design/packaging_advances/index.asp, Copyright 2008; 5 pages.
European Communication under Rule 71(3) EPC, Intention to Grant dated Jun. 2, 2016 corresponding to European Application No. 13722619.7; 26 Pages.
European Extended Search Report dated Dec. 22, 2016; for European Pat. App. No. 16193227.2; 11 pages.
European Response filed on Aug. 24, 2016 to the official communication dated Feb. 23, 2016; for European Pat. App. No. 14742423.8; 13 pages.
European Response to Written Opinion filed on May 21, 2015; for European Pat. App. No. 13722619.7, 9 pages.
Final Office Action dated Aug. 28, 2015; for U.S. Appl. No. 13/946,417; 30 pages.
Final Office Action dated Jun. 9, 2015; for U.S. Appl. No. 13/946,400; 17 pages.
Final Office Action dated Oct. 20, 2016 for U.S. Appl. No. 13/946,400; 34 pages.
Final Office Action dated Oct. 6, 2016; for U.S. Appl. No. 13/946,417; 29 pages.
Frick, et al.; "CMOS Microsystem for AC Current Measurement with Galvanic Isolation;" IEEE Sensors Journal; vol. 3, No. 6; Dec. 2003; 9 pages.
Halg; "Piezo-Hall Coefficients of n-Type Silicon;" Journal of Applied Physics; vol. 64, No. 1; Jul. 1, 1988; 7 pages.
Honeywell International, Inc., "Hall Effect Sensing and Application," Micro Switch Sensing and Control, Chapter 3, http://content.honeywell.com/sensing/prodinfo/solidstate/technical/hallbook.pdf, date unavailable but believed to be before Jan. 2008; 11 pages.
Hosticka; "CMOS Sensor Systems;" Sensors and Actuators A66; Apr. 1998; 7 pages.
Infineon Product Brief, TLE 4941plusC, Differential Hall IC for Wheel Speed Sensing, Oct. 2010, www.infineon.com/sensors, 2 pages.
International Preliminary Report on Patentability dated Jan. 19, 2016 for Int'l PCT Application PCT/US2014/044993; 8 pages.
International Search Report and Written Opinion dated Nov. 3, 2014 for Int'l PCT Application PCT/US2014/044993; 13 pages.
International Search Report and Written Opinion dated Oct. 28, 2014 for Int'l PCT Application PCT/US2014/044991; 13 pages.
Japanese Office Action (with English Translation) dated May 18, 2017 for Japanese Application No. 2015-511491; 8 Pages.
Japanese Office Action dated Jan. 18, 2017 for Japanese Application No. 2016-512930; 7 pages.
Japanese Voluntary Amendment with English Claims dated Dec. 28, 2016; for Japanese Pat. App. No. 2016-528006; 8 pages.
Johnson et al., "Hybrid Hall Effect Device," Appl. Phys. Lett., vol. 71, No. 7, Aug. 1997; 3 pages.

(56) References Cited

OTHER PUBLICATIONS

Kanda et al.; "The Piezo-Hall Effect in n-Silicon;" $22^{nd}$ International Conference on the Physics of Semiconductors; vol. 1, Jan. 1995; 4 pages.
Kapser et al.; "Integrated GMR Based Wheel Speed Sensor for Automotive Applications;" IEEE 2007 Conference on Sensors; Oct. 2007; 4 pages.
Kammerer et al.: "A Hall effect sensors network insensitive to mechanical stress;" Proceedings of IEEE Sensors; vol. 3, Oct. 2004; 4 pages.
Lagorce et al.; "Magnetic and Mechanical Properties of Micromachined Strontium Ferrite/Polyimide Composites;" Journal of Microelectromechanical Systems; vol. 6, No. 4; Dec. 1997; 6 pages.
Lequesne et al.; "High-Accuracy Magnetic Position Encoder Concept;" IEEE Transactions on Industry Applications; vol. 35, No. 3; May/Jun. 1999; 9 pages.
Magnani et al.; "Mechanical Stress Measurement Electronics Based on Piezo-Resistive and Piezo-Hall Effects; " $9^{th}$ International Conference on Electronics, Circuits and Systems 2002; vol. 1; SBN: 0-7803-7596-3; Dec. 2002; 4 pages.
Manic et al.; "Short and Long-Term Stability Problems of Hall Plates in Plastic Packages;" IEEE $38^{th}$ Annual International Reliability Physics Symposium; Apr. 2000; 6 pages.
Manic; "Drift in Silicon Integrated Sensors and Circuits Due to the Thermo-Mechanical Stresses;" Lausanne, École Polytechnique Fédérale De Lausanne 2000; 176 pages.
Melexis Microelectronic Systems, Hall Applications Guide, Section 3—Applications,1997; 48 pages.
Motz et al.; "An Integrated Magnetic Sensor with Two Continuous-Time $\Delta\Sigma$-Converters and Stress Compensation Capability;" IEEE International Solid-State Circuits Conference; Digest of Technical Papers; Feb. 6, 2006; ISBN: 1-4244-0079-1; 7 pages.
Motz, et al.; "A Chopped Hall Sensor with Small Jitter and Programmable "True Power-On" Function;" IEEE Journal of Solid-State Circuits; vol. 40, No. 7; Jul. 2005; 8 pages.
Motz, et al.; "An Integrated Hall Sensor Platform Design for Position, Angle and Current Sensing;" IEEE Sensors 2006; Exco, Daegu, Korea / Oct. 22-25, 2006; 4 pages.
Munter; "A Low-offset Spinning-current Hall Plate;" Sensors and Actuators A21-A23; 1990; 4 pages.
Munter; "Electronic Circuitry for a Smart Spinning-current Hall Plate with Low Offset;" Sensors and Actuators A; Jun. 1991; 5 pages.
Non-Final Office Action dated Dec. 3, 2015; for U.S. Appl. No. 13/946,417; 26 pages.
Non-Final Office Action dated Nov. 19, 2015; for U.S. Appl. No. 13/946,400; 24 pages.
Notice of Allowance dated Apr. 19, 2017 for U.S. Appl. No. 13/891,519; 11 pages.
Notice of Allowance dated Jul. 25, 2017 for U.S. Appl. No. 13/468,478; 10 Pages.
Notice of Allowance dated Mar. 1, 2017 for U.S. Appl. No. 13/891,519; 7 pages.
Notice of Allowance dated May 15, 2017 for U.S. Appl. No. 13/468,478; 15 Pages.
Office Action dated Mar. 20, 2015; for U.S. Appl. No. 13/946,417; 20 pages.
Office Action dated Oct. 20, 2016; for U.S. Appl. No. 13/946,400; 34 pages.
Office Action in U.S. Appl. No. 13/468,478 dated Jan. 15, 2014, 36 pages.
Oniku et al.; "High-Energy-Density Permanent Micromagnets Formed from Heterogeneous Magnetic Powder Mixtures;" IEEE $25^{th}$ International Conference on Micro Electro Mechanical Systems, Jan. 2012; 4 pages.
Park et al.; "Ferrite-Based Integrated Planar Inductors and Transformers Fabricated at Low Temperature;" IEEE Transactions on Magnetics; vol. 33; No. 5; Sep. 1997; 3 pages.
Park et al.;"Batch-Fabricated Microinductors with Electroplated Magnetically Anisotropic and Laminated Alloy Cores", IEEE Transactions on Magnetics, vol. 35, No. 5, Sep. 1999, 10 pages.
Partin et al.; "Temperature Stable Hall Effect Sensors;" IEEE Sensors Journal, vol. 6, No. 1; Feb. 2006; 5 pages.
Pastre, et al.; "A Hall Sensor Analog Front End for Current Measurement with Continuous Gain Calibration;" IEEE Sensors Journal; vol. 7, No. 5; May 2007; 8 pages.
Pastre, et al.; "A Hall Sensor-Based Current Measurement Microsystem With Continuous Gain Calibration;" Research in Microelectronics and Electronics, IEEE vol. 2; Jul. 25; 2005; ISBN: 0-7803-9345-7; 4 pages.
PCT International Preliminary Report and Written Opinion dated Jan. 28, 2016 for International Application No. PCT/US2014/044991; 9 pages.
PCT International Preliminary Report dated Nov. 19, 2015 for International Application No. PCT/US2014/035594; 13 pages.
PCT International Preliminary Report on Patentability and Written Opinion of the ISA dated Nov. 20, 2014; for PCT Pat. App. No. PCT/US2013/037065; 10 pages.
PCT International Search Report and Written Opinion dated Jul. 13, 2013 for International Application No. PCT/US2013/037065; 13 pages.
PCT International Search Report and Written Opinion dated Sep. 12, 2014 for International Application No. PCT/US2014/035594; 16 pages.
Popovic; "Sensor Microsystems;" Proc. $20^{th}$ International Conference on Microelectronics (MWIL 95); vol. 2, NIS, Serbia, Sep. 12-14, 1995; 7 pages.
Randhawa; "Monolithic Integrated Hall Devices in Silicon Circuits;" Microelectronics Journal; vol. 12, No. 6; Sep. 14-17, 1981; 6 pages.
Response (with Amended Claims in English) to Japanese Office Action dated Feb. 13, 2017 for Japanese Application No. 2015-511491; Response filed on Apr. 11, 2017; 10 Pages.
Response (with RCE) to U.S. Final Office Action dated Sep. 16, 2015 for U.S. Appl. No. 13/468,478; Response filed Jan. 14, 2016; 18 Pages.
Response and RCE to U.S. Final Office Action dated Feb. 16, 2016 for U.S. Appl. No. 13/891,519; Response filed on May 12, 2016; 13 pages.
Response and RCE to U.S. Final Office Action dated Nov. 25, 2016 for U.S. Appl. No. 13/891,519; Response filed on Feb. 6, 2017; 18 pages.
Response filed Mar. 3, 2016 to Office Action dated Dec. 3, 2015; for U.S. Appl. No. 13/946,417; 17 pages.
Response filed Nov. 9, 2015 to Final Office Action dated Aug. 28, 2015; for U.S. Appl. No. 13/946,417; 14 pages.
Response filed Apr. 3, 2015; to Office Action dated Jan. 5, 2015; for U.S. Appl. No. 13/946,400; 13 pages.
Response filed on Jan. 19, 2017 to Final Office Action dated Oct. 20, 2016; for U.S Appl. No. 13/946,400; 12 Pages.
Response filed on Jun. 19, 2015 to Office Action dated Mar. 20, 2015; for U.S. Appl. No. 13/946,417; 15 pages.
Response filed on Oct. 3, 2016 to the Office Action dated May 10, 2016; for U.S. Appl. No. 13/468,478; 17 pages.
Response to Communication dated Dec. 11, 2015 for European Application No. 14726492.3-1560; 17 pages.
Response to Japanese Office Action dated Jan. 18, 2017 for Japanese Application No. 2016-512930; Response Filed Apr. 18, 2017; 13 pages.
Response and RCE to Oct. 6, 2016 Final Office Action from U.S. Appl. No. 13/946,417 as filed on Jan. 24, 2017; 14 Pages.
Response to Office Action filed on Jun. 30, 2017 for U.S. Appl. No. 13/946,400; 12 pages.
Response to U.S. Final Office Action dated Feb. 10, 2017 for U.S. Appl. No. 13/468,478; Response filed on May 3, 2017; 9 Pages.
Response and RCE to U.S. Final Office Action dated Jul. 17, 2014 for U.S. Appl. No. 13/468,478; Response Filed Jan. 19, 2015; 12 Pages.
Response to U.S. Final Office Action dated Oct. 20, 2016 (w/RCE) for U.S. Appl. No. 13/946,400; Response filed on Feb. 23, 2017; 17 Pages.

(56) References Cited

OTHER PUBLICATIONS

Response to U.S. Non-Final Office Action dated Apr. 24, 2015 for U.S. Appl. No. 13/891,519; Response filed on Nov. 20, 2015; 11 pages.
Response to U.S. Non-Final Office Action dated Feb. 12, 2015 for U.S. Appl. No. 13/468,478; Response filed Jun. 18, 2015; 11 Pages.
Response to U.S. Non-Final Office Action dated Jan. 15, 2014 for U.S. Appl. No. 13/468,478; Response filed on Jun. 12, 2014; 11 Pages.
Response to U.S. Non-Final Office Action dated Jun. 3, 2016 for U.S. Appl. No. 13/891,519; Response filed on Sep. 1, 2016; 14 pages.
Response to U.S. Non-Final Office Action dated Mar. 15, 2017 for U.S. Appl. No. 13/946,417; Response filed on Jun. 14, 2017; 10 pages.
Response to U.S. Non-Final Office Action dated Nov. 19, 2015 for U.S. Appl. No. 13/946,400; Response filed Feb. 17, 2016; 11 Pages.
Ruther et al.; "Integrated CMOS-Based Sensor Array for Mechanical Stress Mapping;" 5$^{th}$ IEEE Conference on Sensors, Oct. 2007; 4 pages.
Ruther et al.; "Thermomagnetic Residual Offset in Integrated Hall Plates;" IEEE Sensors Journal; vol. 3, No. 6; Dec. 2003; 7 pages.
Sargent; "Switched-capacitor IC controls feedback loop;" EDN; Design Ideas; Feb. 17, 2000; 2 pages.
Schneider; "Temperature Calibration of CMOS Magnetic Vector Probe for Contactless Angle Measurement System," IEDM 1996 4 Pages.
Schott et al.; "Linearizing Integrated Hall Devices;" 1997 International Conference on Solid-State Sensors and Actuators, Jun. 16-19, 1997; 4 Pages.
Schott, et al.; "CMOS Single-Chip Electronic Compass with Microcontroller;" IEEE Journal of Solid-State Circuits; vol. 42, No. 12; Dec. 2007; 11 pages.
Simon et al.; "Autocalibration of Silicon Hall Devices;" 8$^{th}$ International Conference on Solid-State Sensors and Actuators; vol. 2; Jun. 25, 1995; 4 pages.
Smith et al.; "Low Magnetic Field Sensing with GMR Sensors;" Sensor Magazine; Part 1; Sep. 1999; http://archives.sensorsmag.com/articles/0999/76mail.shtml; pp. 1-8.
Smith et al.; "Low Magnetic Field Sensing with GMR Sensors;" Sensor Magazine; Part 2; Oct. 1999; http://archives.sensorsmag.com/articles/1099/84/mail.shtml; pp. 1-11.
Steiner et al.; "Double-Hall Sensor with Self-Compensated Offset;" International Electron Devices Meeting; Dec. 7, 1997; ISBN: 0-7803-4100-7; 4 pages.
Steiner et al; Offset Reduction in Hall Devices by Continuous Spinning Current Method; Sensors and Actuators A66; 1998; 6 pages.
Stellrecht et al.; Characterization of Hygroscopic Swelling Behavior of Mold Compounds and Plastic Packages; IEEE Transactions on Components and Packaging Technologies; vol. 27, No. 3; Sep. 2004; 8 pages.
Tian et al.; "Multiple Sensors on Pulsed Eddy-Current Detection for 3-D Subsurface Crack Assessment;" IEEE Sensors Journal, vol. 5, No. 1; Feb. 2005; 7 pages.
Trontelj et al; "CMOS Integrated Magnetic Field Source Used as a Reference in Magnetic Field Sensors on Common Substrate;" WEP 1-6; IMTC; May 1994; 3 pages.
U.S. Advisory Action dated Feb. 16, 2017 for U.S. Appl. No. 13/946,400; 4 Pages.
U.S. Final Office Action dated Feb. 10, 2017 for U.S. Appl. No. 13/468,478; 27 Pages.
U.S. Final Office Action dated Feb. 16, 2016 for U.S. Appl. No. 13/891,519; 14 pages.
U.S. Final Office Action dated Jul. 17, 2014 for U.S. Appl. No. 13/468,478; 13 Pages.
U.S. Final Office Action dated Nov. 25, 2016 for U.S. Appl. No. 13/891,519; 13 pages.
U.S. Final Office Action dated Sep. 16, 2015 for U.S. Appl. No. 13/468,478; 19 Pages.
U.S. Final Office Action dated Sep. 8, 2017 for U.S. Appl. No. 13/946,417; 56 pages.
U.S. Non-Final Office Action dated Apr. 6, 2017 for U.S. Appl. No. 13/946,400; 36 Pages.
U.S. Non-Final Office Action dated Aug. 24, 2015 for U.S. Appl. No. 13/891,519; 14 pages.
U.S. Non-Final Office Action dated Feb. 12, 2015 for U.S. Appl. No. 13/468,478; 14 Pages.
U.S. Non-Final Office Action dated Jan. 5, 2015 for U.S. Appl. No. 13/946,400; 56 Pages.
U.S. Non-Final Office Action dated Jun. 3, 2016 for U.S. Appl. No. 13/891,519; 19 pages.
U.S. Non-Final Office Action dated Mar. 15, 2017 from U.S. Appl. No. 13/946,417; 25 Pages.
U.S. Non-Final Office Action dated May 10, 2016 corresponding to U.S. Appl. No. 13/468,478; 20 Pages.
Udo; "Limits of Offset Cancellation by the Principle of Spinning Current Hall Probe;" Proceedings of IEEE Sensors; Oct. 2004; 4 pages.
Voluntary Amendment dated Nov. 2, 2016 with English claims for Chinese Application No. 201480040243.6; 13 pages.
Voluntary Amendment with English Claims dated Nov. 7, 2016 for Korean App. No. 10-2016-7004178; 11 Pages.
Wu, et al.; "A Chopper Current-Feedback Instrumentation Amplifier with a 1mHz 1/f Noise Corner and an AC-Coupled Ripple-Reduction Loop;" IEEE International Solid-State Circuits Conference; Feb. 10, 2009; 3 pages.
Zou et al.; "Three-Dimensional Die Surface Stress Measurements in Delaminated and Non-Delaminated Plastic Packages;" 48th Electronic Components and Technology Conference; May 25, 1998; 12 pages.
Response to Official Communication dated Mar. 13, 2017 for European Application No. 16193227.2; 7 pages.
U.S. Final Office Action dated Oct. 5, 2017 for U.S. Appl. No. 13/946,400; 39 pages.
PCT International Search Report and Written Opinion of the International Searching Authority dated Feb. 12, 2019 for International Application No. PCT/US2018/028822; 20 pages.
PCT International Search Report and Written Opinion of the International Searching Authority dated Jan. 18, 2019 for International Application No. PCT/US2018/028822; 20 pages.

\* cited by examiner

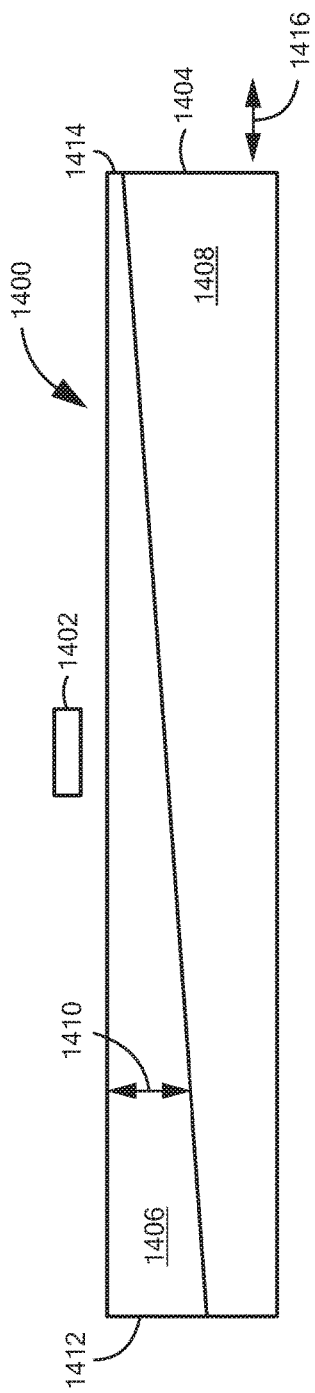
*FIGURE 14*
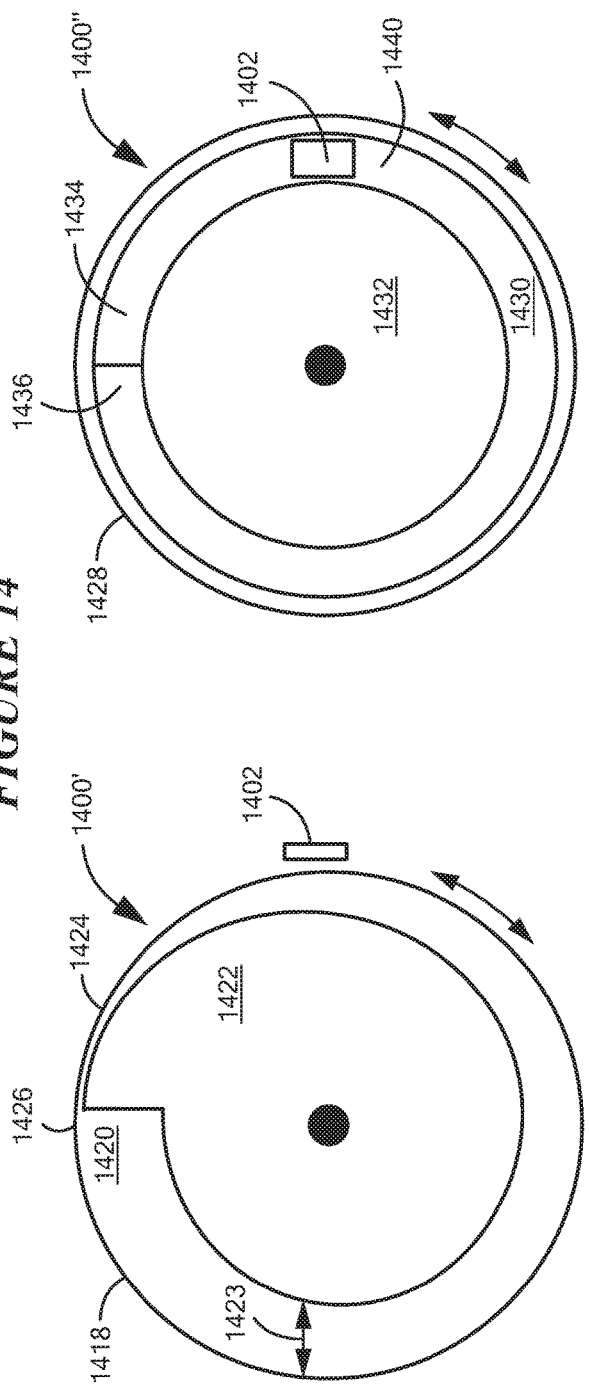
*FIGURE 14A*
*FIGURE 14B*

PACKAGES FOR COIL ACTUATED POSITION SENSORS

FIELD

This disclosure relates to magnetic field sensing and, more particularly, to structural arrangements for magnetic field sensors that generate reflected magnetic fields.

BACKGROUND

Magnetic field sensors are often used to detect a ferromagnetic target. They often act as sensors to detect motion or position of the target. Such sensors are ubiquitous in many areas of technology including robotics, automotive, manufacturing, etc. For example, a magnetic field sensor may be used to detect when a vehicle's wheel locks up, triggering the vehicle's control processor to engage the anti-lock braking system. In this example, the magnetic field sensor may detect rotation of the wheel. Magnetic field sensor may also detect distance to an object. For example, a magnetic field sensor may be used to detect the position of a hydraulic piston.

SUMMARY

In an embodiment, an apparatus comprises one or more substrates; one or more coils, at least one of the coils configured to produce a first magnetic field that induces eddy currents in a conductive target that generates a reflected magnetic field; one or more magnetic field sensing elements supported by the one or more substrates to detect the reflected magnetic field; and a conductive support structure to support the one or more substrates, the support structure having a gap in an area adjacent to the one or more coils so that the support structure does not generate a reflected magnetic field in response to the first magnetic field.

One or more of the following features may be included.

The one or more magnetic field sensing elements may be arranged in a grid pattern on the one or more substrates.

At least one of the coils may comprise a plurality of traces and wherein the one or more magnetic field sensing elements are positioned on the substrate in a space between traces of the coil.

The coil may include a counter coil to produce a local magnetic field in a direction opposite to the direction of the first magnetic field.

At least one of the coils may comprise a plurality of traces and wherein the one or more magnetic field sensing elements are positioned in a space between one or more traces of the counter coil.

The one or more substrates may comprise one or more of: a semiconductor material, a glass material, or a ceramic material.

A first substrate of the one or more substrates may support the one or more coils and one or more second substrates of the one or more substrates support the one or more magnetic field sensing elements.

A third substrate of the one or more substrates may support a processing circuit.

The first substrate may support two or more coils.

The first substrate may support one or more coils and one or more magnetic field sensing elements.

The second one or more substrates may support one or more processing circuits.

Each of the magnetic field sensing elements may be supported by a different substrate.

The substrates, coils, and magnetic field sensing elements may form one or more magnetic field sensors.

An adhesive may adhere at least two of the one or more substrates to each other.

The conductive support structure may include a lead frame or a pad frame.

At least one of the one or more coils may be supported by at least one of the one or more substrates.

In another embodiment, an apparatus comprises a first substrate; two coils supported by the first substrate and arranged next to each other, the coils configured to each generate a magnetic field which produces eddy currents in and a reflected magnetic field from a conductive target, the two coils arranged so their respectively generated magnetic fields substantially cancel each other in an area between the coils; and one or more magnetic field sensing elements positioned in the area between the coils and configured to detect the reflected magnetic field.

One or more of the following features may be included.

The one or more magnetic field sensing elements may comprise a bridge circuit.

The one or more magnetic field sensing elements may comprise at least two pairs of magnetic field sensing elements.

A center area of the conductive target may be adjacent to one of the pairs of magnetic field sensing elements and an edge of the conductive target may be adjacent to another of the pairs of magnetic field sensing elements.

The apparatus may include second substrate, wherein the one or more magnetic field sensing elements and/or a processing circuit are supported by the second substrate.

The second substrate may be centered in the area between the coils.

The first and/or second substrates may comprise one or more of: a semiconductor material, a glass material, or a ceramic material.

In another embodiment, an apparatus comprises a first substrate; a first magnetic field sensor supported by the first substrate, the first magnetic field sensor comprising a first pair of two coils supported by the first substrate and arranged next to each other, the coils configured to each generate a magnetic field which produces eddy currents in and a first reflected magnetic field from a first conductive target, the first pair of two coils arranged so their respectively generated magnetic fields substantially cancel each other in an area between the coils. The apparatus includes a second substrate supporting one or more magnetic field sensing elements positioned in the area between the first pair of two coils and configured to detect the first reflected magnetic field; and a second magnetic field sensor supported by the first substrate, the second magnetic field sensor comprising a second pair of two coils supported by the first substrate and arranged next to each other, the second pair of two coils configured to each generate a magnetic field which produces eddy currents in and a reflected magnetic field from a second conductive target, the second pair of two coils arranged so their respectively generated magnetic fields substantially cancel each other in an area between the coils. The apparatus includes a third substrate supporting one or more magnetic field sensing elements positioned in the area between the second pair of two coils and configured to detect the second reflected magnetic field.

In another embodiment, a system comprises one or more substrates; one or more magnetic field sensing elements supported by the one or more substrates to detect an alternating magnetic field; and a conductive support structure to support the one or more substrates, the support structure having a shape in an area adjacent to the magnetic field sensing elements that does not generate a reflected magnetic field in response to the alternating magnetic field.

One or more of the following features may be included. The apparatus may include one or more coils, wherein at least one of the one or more coils generates the alternating magnetic field.

At least one of the one or more coils may be supported by at least one of the one or more substrates.

BRIEF DESCRIPTION OF THE DRAWINGS

The foregoing features may be more fully understood from the following description of the drawings. The drawings aid in explaining and understanding the disclosed technology. Since it is often impractical or impossible to illustrate and describe every possible embodiment, the provided figures depict one or more examples of embodiments. Accordingly, the figures are not intended to limit the scope of the invention. Like numbers in the figures denote like elements.

FIG. 8A is an isometric view of embodiments of the pressure sensor of FIG. 8.

FIG. 14 is a side view of a magnetic field sensor and a magnetic target having material of varying thickness.

FIG. 14A is a side view of a magnetic field sensor and a magnetic target having material of varying thickness.

FIG. 14B is a side view of a magnetic field sensor and a magnetic target having material of varying thickness.

DETAILED DESCRIPTION

Figure 1:
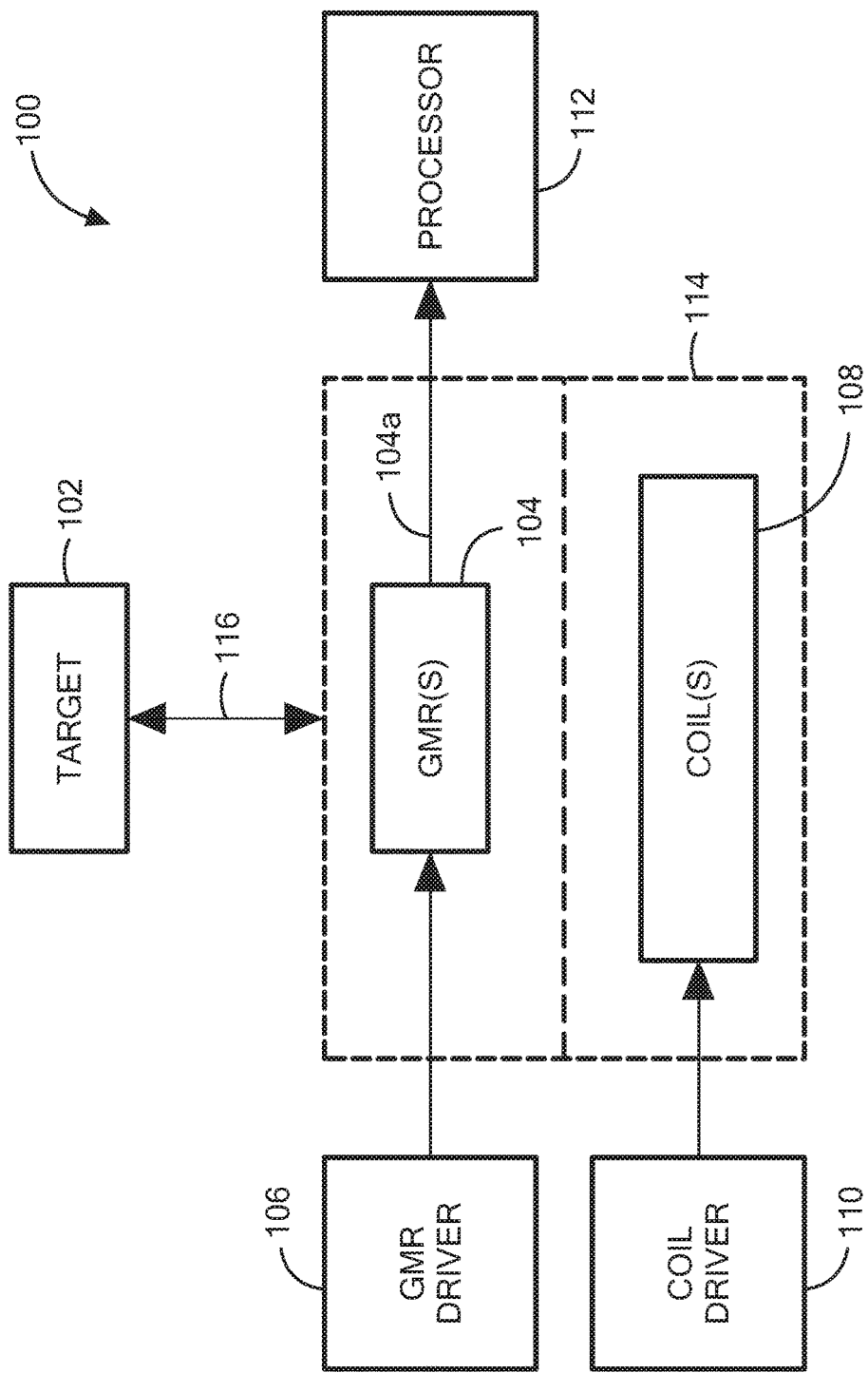
FIG. 1 is a block diagram of a system for sensing a target.

As used herein, the term "magnetic field sensing element" is used to describe a variety of electronic elements that can sense a magnetic field. The magnetic field sensing element can be, but is not limited to, a Hall Effect element, a magnetoresistance (MR) element, or a magnetotransistor. As is known, there are different types of Hall Effect elements, for example, a planar Hall element, a vertical Hall element, and a Circular Vertical Hall (CVH) element. As is also known, there are different types of magnetoresistance elements, for example, a semiconductor magnetoresistance element such as Indium Antimonide (InSb), a giant magnetoresistance (MR) element, an anisotropic magnetoresistance element (AMR), a tunneling magnetoresistance (TMR) element, and a magnetic tunnel junction (MTJ). The magnetic field sensing element may be a single element or, alternatively, may include two or more magnetic field sensing elements arranged in various configurations, e.g., a half bridge or full (Wheatstone) bridge. Depending on the device type and other application requirements, the magnetic field sensing element may be a device made of a type IV semiconductor material such as Silicon (Si) or Germanium (Ge), or a type III-V semiconductor material like Gallium-Arsenide (GaAs) or an Indium compound, e.g., Indium-Antimonide (InSb).

As is known, some of the above-described magnetic field sensing elements tend to have an axis of maximum sensitivity parallel to a substrate that supports the magnetic field sensing element, and others of the above-described magnetic field sensing elements tend to have an axis of maximum sensitivity perpendicular to a substrate that supports the magnetic field sensing element. In particular, planar Hall elements tend to have axes of sensitivity perpendicular to a substrate, while metal based or metallic magnetoresistance elements (e.g., MR, TMR, AMR) and vertical Hall elements tend to have axes of sensitivity parallel to a substrate.

As used herein, the term "magnetic field sensor" is used to describe a circuit that uses a magnetic field sensing element, generally in combination with other circuits. Magnetic field sensors are used in a variety of applications, including, but not limited to, an angle sensor that senses an angle of a direction of a magnetic field, a current sensor that senses a magnetic field generated by a current carried by a current-carrying conductor, a magnetic switch that senses the proximity of a ferromagnetic object, a rotation detector that senses passing ferromagnetic articles, for example, magnetic domains of a ring magnet or a ferromagnetic target (e.g., gear teeth) where the magnetic field sensor is used in combination with a back-biased or other magnet, and a magnetic field sensor that senses a magnetic field density of a magnetic field.

As used herein, the terms "target" and "magnetic target" are used to describe an object to be sensed or detected by a magnetic field sensor or magnetic field sensing element. The target may comprise a conductive material that allows for eddy currents to flow within the target, for example a metallic target that conducts electricity.

FIG. 1 is a block diagram of a system 100 for detecting a conductive target 102. Target 102 may be magnetic or non-magnetic in various embodiments. System 100 includes one or more magnetoresistance (MR) elements 104 and an MR driver circuit 106. MR driver circuit may include a power supply or other circuit that provides power to MR elements 104. In embodiments, MR elements 104 may be replaced with other types of magnetic field sensing elements such as Hall effect elements, etc. MR elements 104 may comprise a single MR element or multiple MR elements. The MR elements may be arranged in a bridge configuration, in certain embodiments.

System 100 may also include one or more coils 108 and a coil driver circuit 110. Coils 108 may be electrical coils, windings, wires, traces, etc. configured to generate a magnetic field when current flows through the coils 108. In embodiments, coils 108 comprise two or more coils, each a conductive trace supported by substrate, such as a semiconductor substrate, a glass substrate, a ceramic substrate, or the like. In other embodiments, coils 108 may not be supported by a substrate. For example, coils 108 may be supported by a chip package, a frame, a PCB, or any other type of structure that can support traces of a coil. In other embodiments, coils 108 may be free standing wire, i.e. not supported by a separate supporting structure.

Coil driver 110 is a power circuit that supplies current to coils 108 to generate the magnetic field. In an embodiment, coil driver 110 may produce an alternating current so that coils 108 produce alternating magnetic fields (i.e. magnetic fields with magnetic moments that change over time). Coil driver 110 may be a circuit implemented, in whole or in part, on the semiconductor die.

System 100 may also include processor 112 coupled to receive signal 104a from MR elements 104, which may represent the magnetic field as detected by MR elements 104. Processor 100 may receive signal 104a and use it to determine a position, speed, direction, or other property of target 102.

MR elements 104 and coils 108 may be positioned on substrate 114. Substrate 114 may comprise semiconductor substrates, such as silicon substrates, a chip package, PCB or other type of board-level substrates, or any type of platform that can support MR elements 104 and coils 108. Substrate 114 may include a single substrate or multiple substrates, as well as a single type of substrate or multiple types of substrates.

In operation, MR driver 106 provides power to MR elements 104 and coil driver 110 provides current to coils 108. In response, coils 108 produce a magnetic field that can be detected by MR elements 104, which produce signal 104a representing the detected magnetic field.

As target 102 moves in relation to the magnetic field, its position and movement through the field changes the field. In response, signal 104a produced by MR elements 104 changes. Processor 112 receives signal 104a and processes the changes in (and/or the state of) the signal to determine position, movement, or other characteristics of target 102. In an embodiment, system 100 can detect movement or position of target 102 along axis 116. In other words, system 100 may detect the position of target 102 in proximity to MR elements 104 as target 102 moves toward or away from MR elements 104 and coils 108. System 102 may also be able to detect other types of position or movement of target 102.

Figure 2:
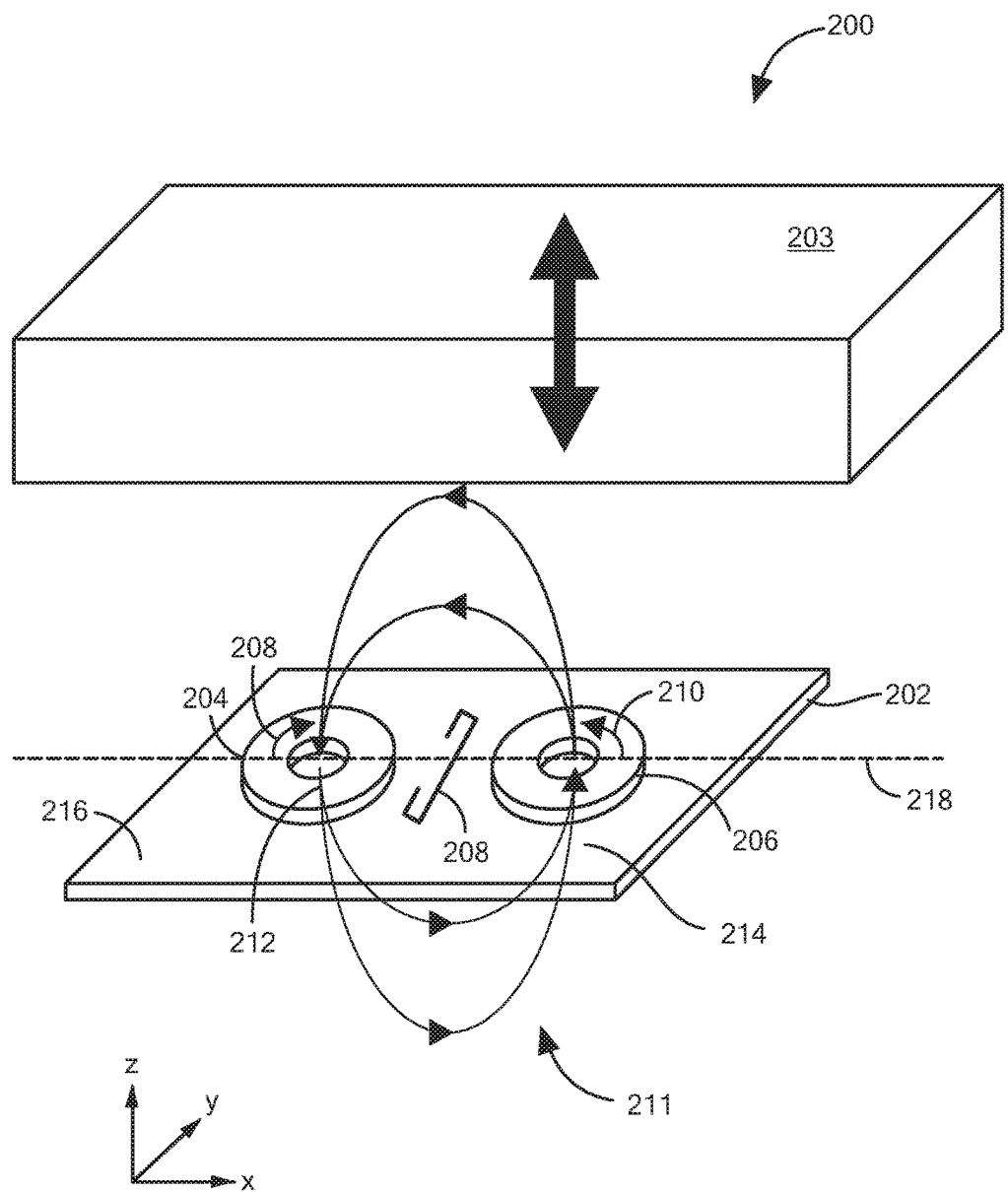
FIG. 2 is an isometric diagram of a system for sensing a target.

Referring now to FIG. 2, system 200 may be the same as or similar to system 100. Substrate 202 may be the same as or similar to substrate 114, and may support coil 204, coil 206, and MR element 208. Although one MR element is shown, MR element 208 may comprise two or more MR elements depending on the embodiment of system 200. Target 203 may be the same as or similar to target 102.

Although not shown, an MR driver circuit 106 may provide current to MR element 208 and coil driver circuit 110 may provide current to coils 204 and 206.

Coil 204 and 206 may be arranged so that the current flows through coils 204 and 206 in opposite directions, as shown by arrow 208 (indicating a clockwise current in coil 204) and arrow 210 (indicating a counterclockwise current in coil 206). As a result, coil 204 may produce a magnetic field having a magnetic moment in the negative Z direction (i.e. down, in FIG. 2), as indicated by arrow 212. Similarly, coil 206 may produce a magnetic field having a magnetic moment in the opposite direction, the positive Z direction, as indicated by arrow 214. An aggregate magnetic field 211 produced by both coils may have a shape similar to that shown by magnetic field lines 211. It will be appreciated that coils 204, 206 may be formed by a single coil structure respectively wound so that the current through the coils flows in opposite directions. Alternatively, coils 204, 206 may be formed by separate coil structures.

In an embodiment, MR element 208 may be placed between coils 204 and 206. In this arrangement, absent any other magnetic fields aside from those produced by coils 204 and 206, the net magnetic field at MR element 208 may be zero. For example, the negative Z component of the magnetic field produced by coil 204 may be canceled out by the positive Z component of the magnetic field produced by coil 206, and the negative X component of the magnetic field shown above substrate 202 may be canceled out by the positive X component of the magnetic field shown below substrate 202. In other embodiments, additional coils may be added to substrate 202 and arranged so that the net magnetic field at MR element 208 is substantially nil.

To achieve a substantially zero magnetic field at the location of MR element 208, coil 204 and coil 206 may be placed so that current through the coils flows in circular patterns substantially in the same plane. For example, the current through coil 204 and 206 is flowing in circular patterns through the coils. As shown, those circular patterns are substantially coplanar with each other, and with the top surface 216 of substrate 202.

As noted above, coil driver 110 may produce an alternating field. In this arrangement, the magnetic field shown by magnetic field lines 211 may change direction and magnitude over time. However, during these changes, the magnetic field at the location of MR element 208 may remain substantially nil.

In operation, as target 203 moves toward and away from MR element 208 (i.e. in the positive and negative Z direction), magnetic field 211 will cause eddy currents to flow within target 203. These eddy currents will create their own magnetic fields, which will produce a non-zero magnetic field in the plane of the MR element 208, which non-zero magnetic field can be sensed to detect the motion or position of target 203.

Figure 2A:
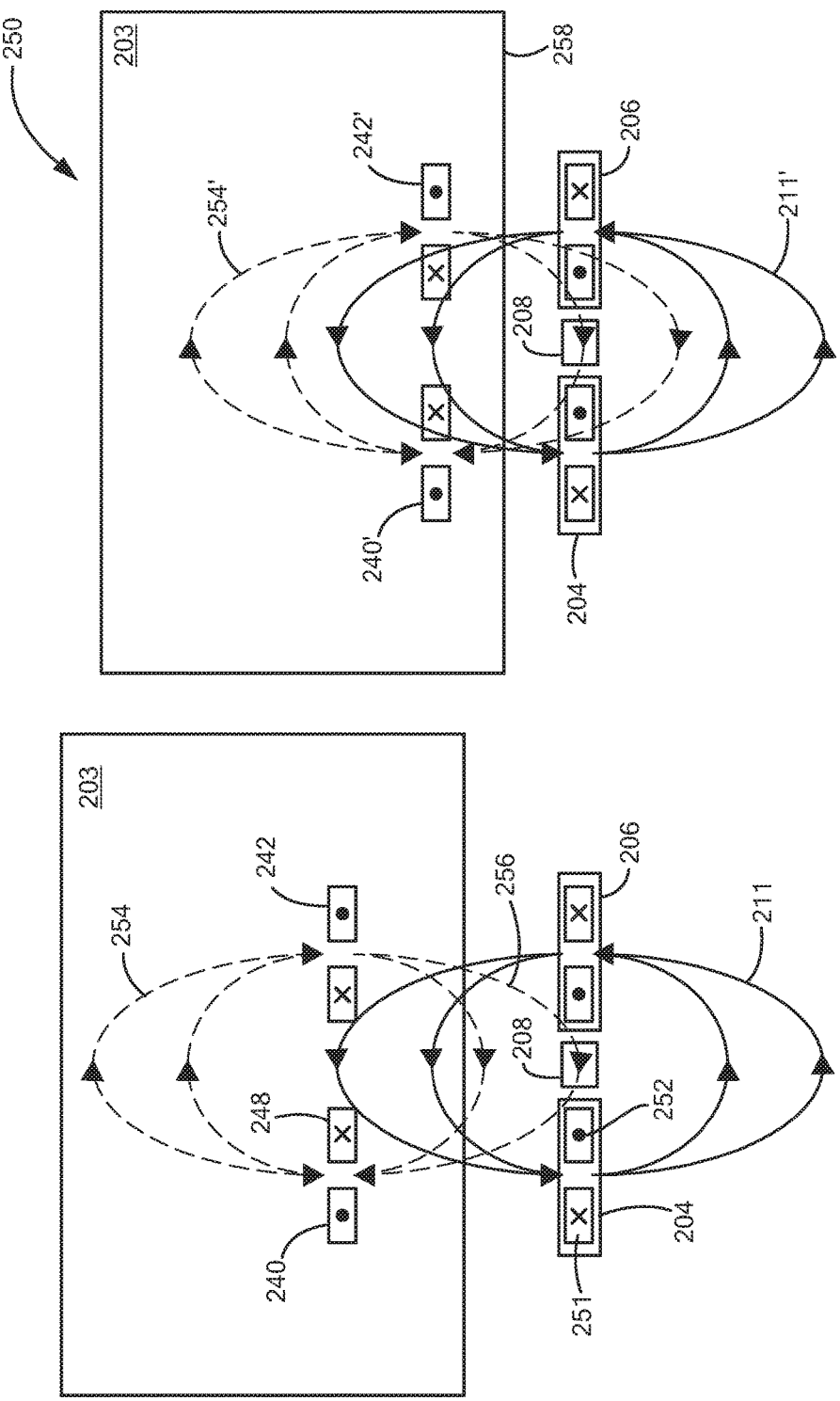
FIG. 2A shows cross-sectional views of the system of FIG. 2.

Referring to FIG. 2A, a cross-sectional view 250 of system 200, as viewed at line 218 in the Y direction, illustrates the eddy currents within target 203. The 'x' symbol represents a current flowing into the page and the '•' symbol represents a current flowing out of the page. As noted above, the current through coils 204 and 206 may be an alternating current, which may result in an alternating strength of magnetic field 211. In embodiments, the phase of the alternating current through coil 204 matches the phase of the alternating current through coil 206 so that magnetic field 211 is an alternating or periodic field.

Alternating magnetic field 211 may produce reflected eddy currents 240 and 242 within magnetic target 203. Eddy currents 240 and 242 may be opposite in direction to the current flowing through coils 204 and 206, respectively. As shown, eddy current 246 flows out of the page and eddy current 248 flows into the page, while coil current 251 flows into the page and current 252 flows out of the page. Also, as shown, the direction of eddy current 242 is opposite the direction of the current through coil 206.

Eddy currents 240 and 242 form a reflected magnetic field 254 that has a direction opposite to magnetic field 211. As noted above, MR element 208 detects a net magnetic field of zero due to magnetic field 211. However, MR element 208 will detect a non-zero magnetic field in the presence of reflected magnetic field 254. As illustrated by magnetic field line 256, the value of reflected magnetic field 254 is non-zero at MR element 208.

As target 203 moves closer to coils 204 and 206, magnetic field 211 may produce stronger eddy currents in target 203. As a result, the strength of magnetic field 254 may change. In FIG. 2A, magnetic field 211' (in the right-hand panel of FIG. 2A) may represent a stronger magnetic field than magnetic field 211 due, for example, to the closer proximity of target 203 to coils 204 and 206. Thus, eddy currents 240' and 242' may be stronger currents than eddy currents 240 and 242, and magnetic field 254' may be stronger than magnetic field 254. This phenomenon may result in MR element 208 detecting a stronger magnetic field (i.e. magnetic field 254') when target 203 is closer to coils 204 and 206, and a weaker magnetic field (i.e. magnetic field 254) when target 203 is further away from coils 204 and 206.

Also, eddy currents 240' and 242' generally occur on or near the surface of target 203. Therefore, as target 203 moves closer to co MR element 208, MR element 208 may experience a stronger magnetic field from the eddy currents because the source of the magnetic field is closer to MR element 208.

Figure 3:
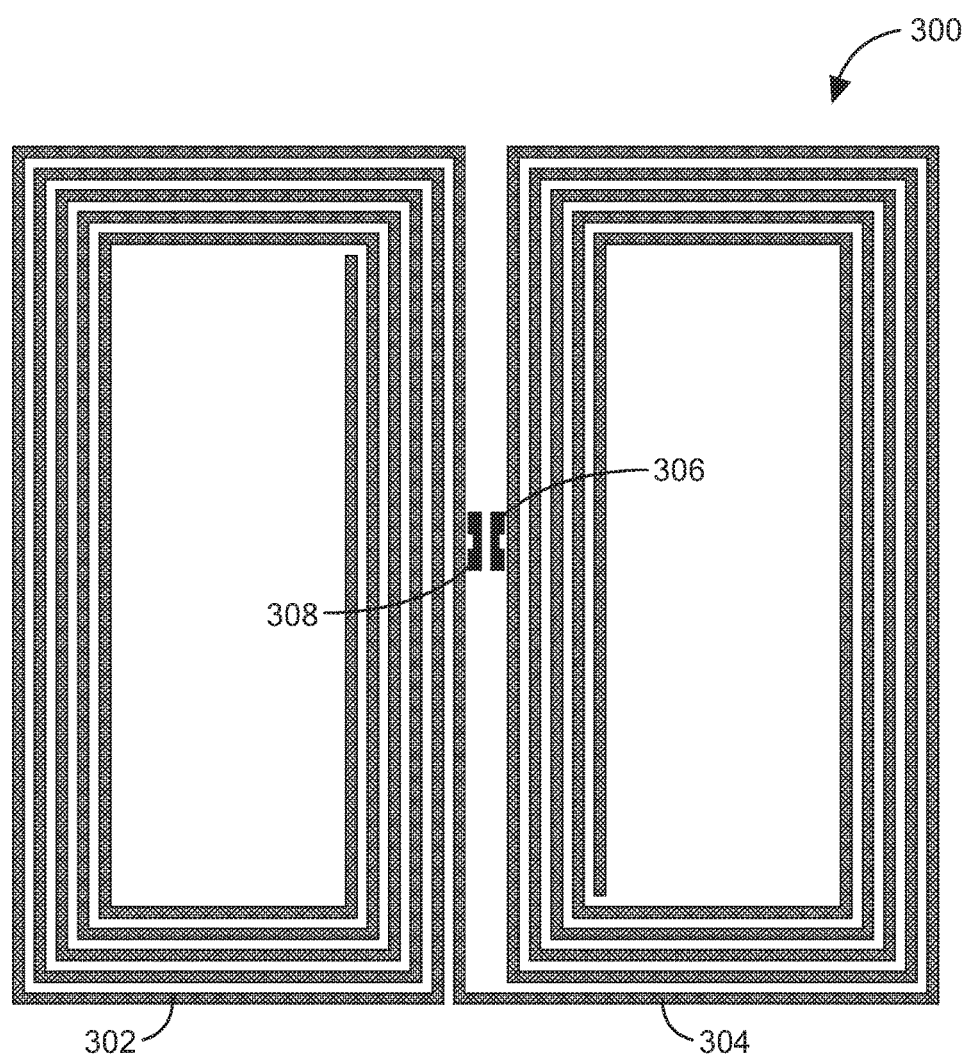
FIG. 3 is a schematic diagram of a coil and magnetoresistance (MR) elements for sensing a target.

FIG. 3 is a schematic diagram of a circuit 300 including coils 302 and 304, and MR elements 306 and 308. Coils 302 and 304 may be the same as or similar to coils 204 and 206, and MR elements 306 and 308 may each be the same as or similar to MR element 208.

In an embodiment, coils 302 and 304, and MR elements 306 and 308 may be supported by a substrate. For example, coils 302 and 304 may comprise conductive traces supported by a substrate and MR elements 306 and 308 may be formed on a surface of or in the substrate.

In an embodiment, coils 302 and 304 may comprise a single conductive trace that carries current. The portion of the trace forming coil 302 may loop or spiral in a direction opposite to the portion of the trace forming coil 304, so that the current through each coil is equal and flows in opposite directions. In other embodiments, multiple traces may be used.

Coils 302 and 304 are symmetrically positioned on opposite sides of MR elements 306 and 308, with MR elements 308 and 304 in the middle. This may result in MR elements 306 and 308 being in the center of the magnetic field produced by coils 302 and 304, so that, absent any other stimulus, the magnetic field detected by MR elements 306 and 308 as a result of magnetic fields produced by coils 302 and 304 (referred to herein as the directly coupled magnetic field) is substantially nil.

Figure 3A:
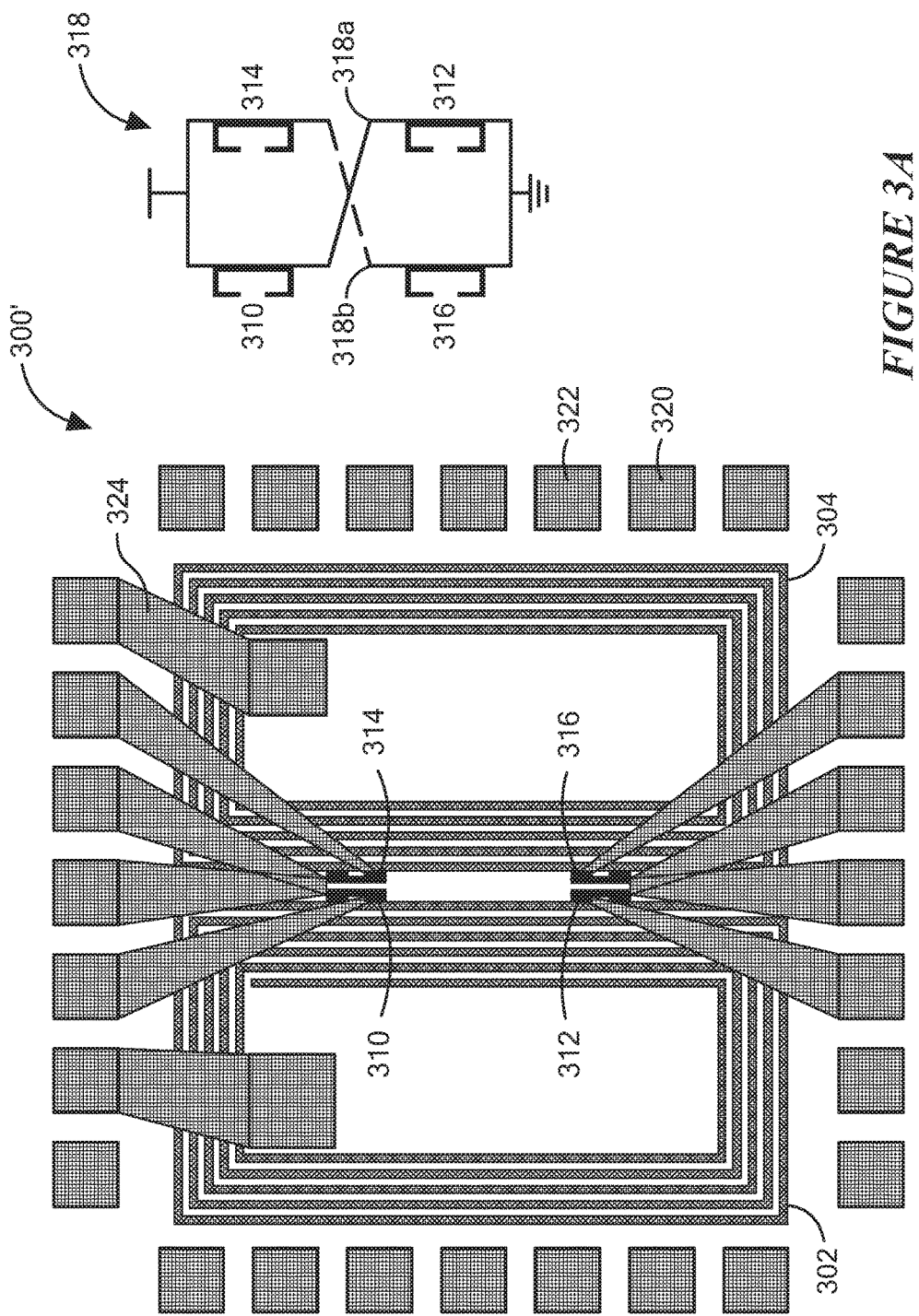
FIG. 3A is a schematic diagram of an embodiment of a coil and MR elements for sensing a target, including bond pads.

FIG. 3A is a schematic diagram of an embodiment of a magnetic field detection circuit 300', which may be the same as or similar to system 100 in FIG. 1. Coils 302 and 304 may be supported by a substrate as described above. Circuit 300' may include four MR elements 310, 312, 314, and 316, which may be coupled in a bridge configuration 318. In embodiments, bridge 318 may produce a differential output consisting of signals 318a and 318b.

Arranging the MR elements in a bridge may, in certain embodiments, increase the sensitivity of the magnetic field sensor. In an embodiment, a target is movable with respect to the circuit 300' such that as the target approaches the circuit it mainly moves towards MR elements 310, 312, but not towards MR elements 314, 316. With this configuration, the resistance of MR elements 310 and 312 may change and the resistance of MR elements 314 and 316 may remain relatively constant as the target approaches and recedes from the MR elements. If, for example, MR elements are aligned so that the MR resistance of 310, 312 decreases and the resistance of MR elements 314, 316 increases as the target approaches, then signal 318a will decrease and signal 318b will increase in voltage as the target approaches. The opposite reaction of the MR elements (and the differential signals 318a and 318b) may increase sensitivity of the magnetic field detection circuit while also allowing the processor that receives the differential signal to ignore any common mode noise.

In embodiments, arranging MR elements 310-316 in a bridge may allow for detection of the difference in the position of the target over the set of resistors and/or detection of a phase difference between the bridge outputs. This may be utilized, for example, to detect tilt or deformation of a target.

Circuit 300' may also include a bond pads 320 having multiple leads 322 that can be accessed and form connections external to a chip package (not shown). Lead wires or conductive traces 324 may connect MR elements 310, 312, 314, and 316 to external leads or pads 322 so they can be coupled to other circuits like, for example, MR driver 106.

Figure 3B:
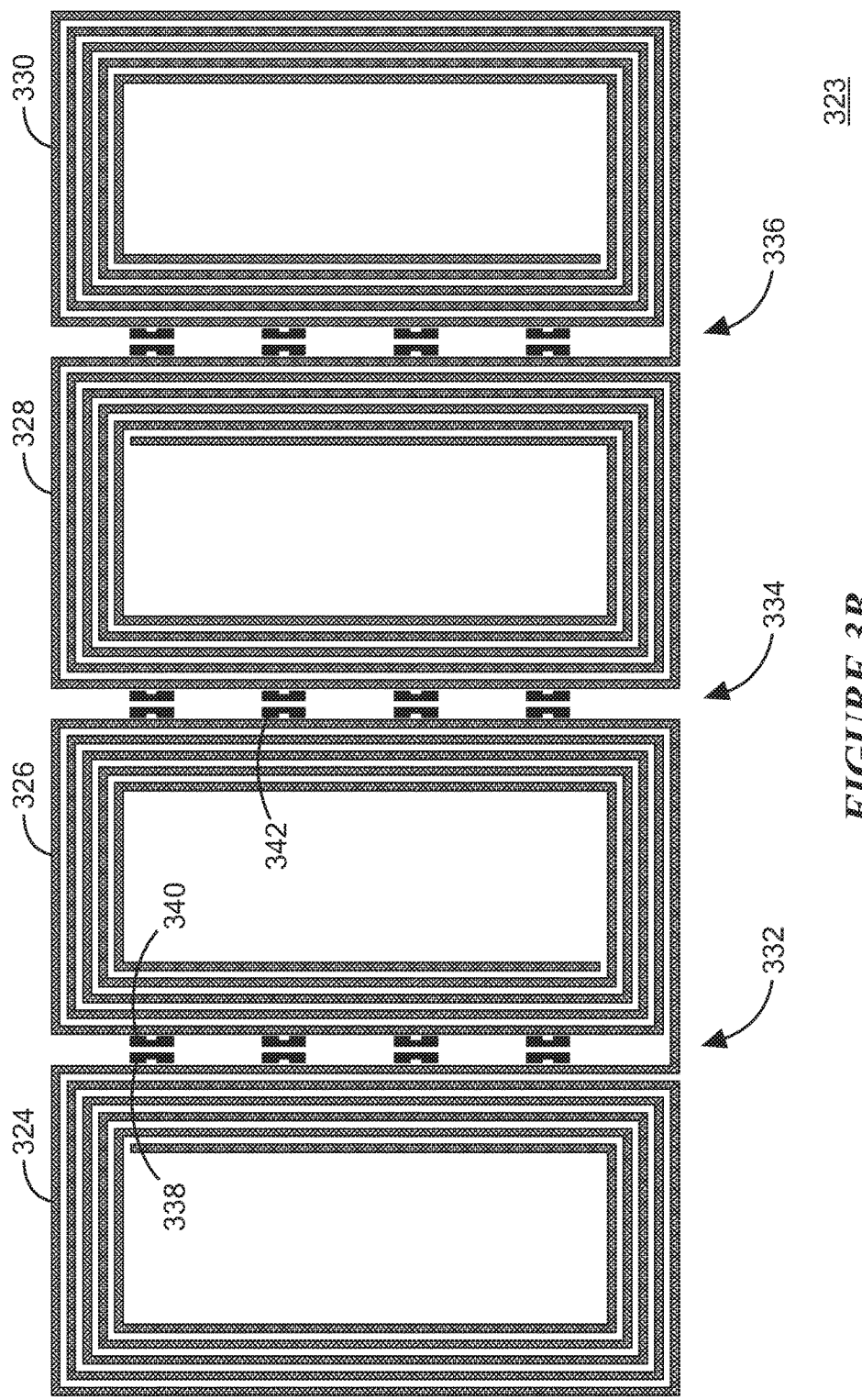
FIG. 3B is schematic diagram of an embodiment of coil and MR elements for sensing a target.

Referring to FIG. 3B, a circuit 323 includes four coils 324-330 and three rows 332, 334, and 336 of MR elements. Circuit 323 may be used to detect location or motion of a target.

The coils may produce magnetic fields in alternating patterns. For example, coil 324 may produce a field going into the page, coil 326 may produce a field coming out of the page, coil 328 may produce a field going into the page, and coil 330 may produce a field coming out of the page. As a result, the magnetic field detected by the MR elements in rows 332, 334, and 336 as a result of magnetic fields produced by coils 324, 326, 328, 330 may be substantially nil.

Circuit 323 may also be extended by adding additional coils and additional MR elements. In embodiments, the additional coils may be configured to create magnetic fields with alternating directions, as described above, and the MR elements between the coils may be placed so that they detect a magnetic field that is substantially nil.

The MR elements in rows 332, 334, and 336 may form a grid. As a target moves above the grid and approaches the MR elements, the MR elements will be exposed to and detect the reflected magnetic field produced by the eddy currents flowing in the target as a result of the magnetic fields produced by the coils 324-330. For example, if a target moves over MR elements 338 and 340, those MR elements may detect the reflected magnetic field and produce an output signal indicating as much. A processor receiving the output signals from the MR elements can then identify the location of the target as above or near MR elements 338 and 340. If the target then moves close to MR element 342, MR element 342 will detect the reflected magnetic field from the target and produce an output signal indicating the target was detected. The processor receiving the output signals can then identify the location of the target as above or near MR element 342.

A single large target may be placed in front of the grid 332,334 and 336. Then the difference of reflected fields experienced by each MR element is a mapping of the parallelism of the target and the plane of the grid. It can be also used to map the deformations of the target as function of an external constraint.

Figure 4:
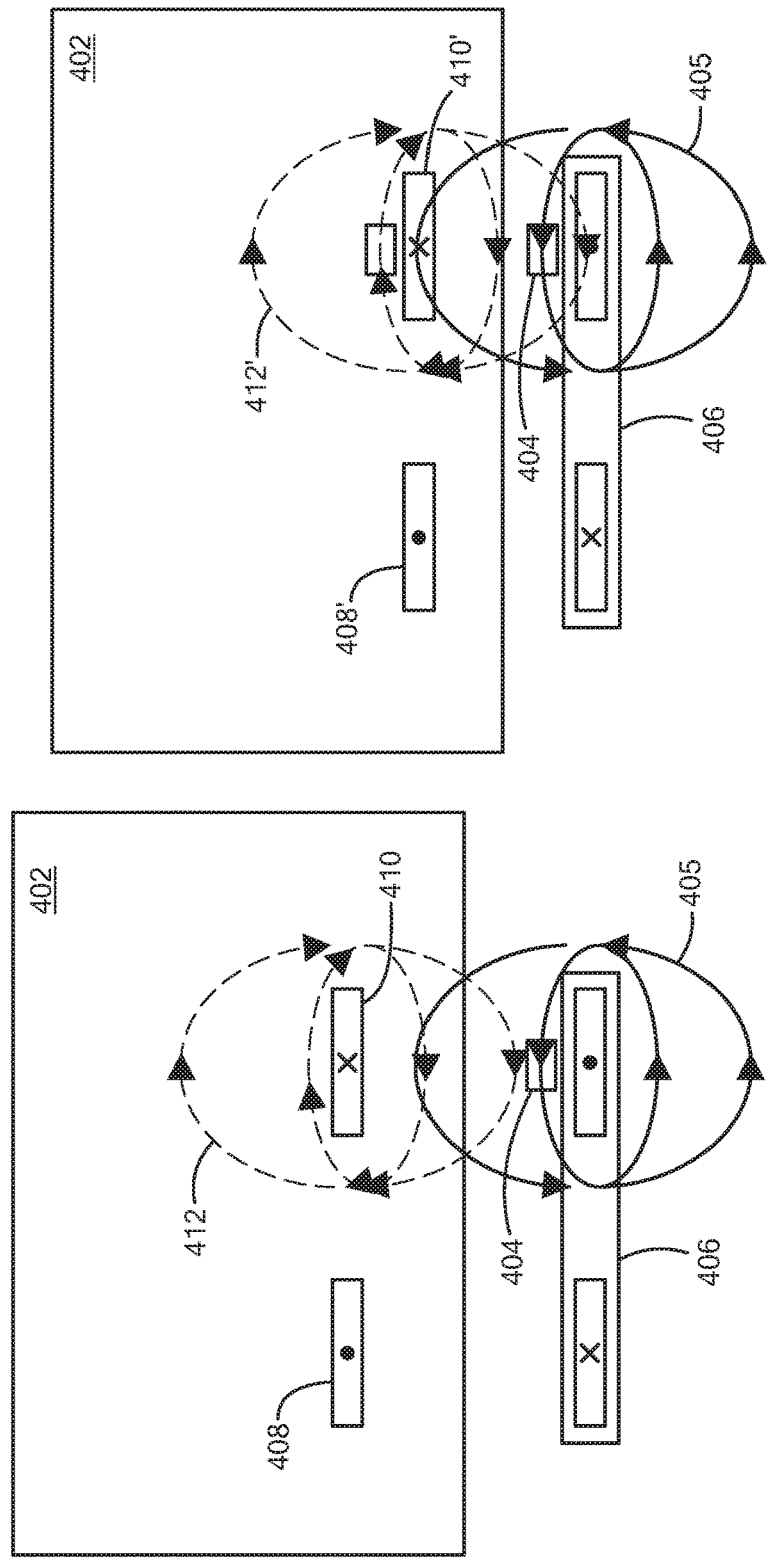
FIG. 4 is a cross-sectional view of a system for sensing a target.

Referring to FIG. 4, a system 400 for detecting a target 402 may use a single coil and MR element to detect target 402. MR element 404 may be placed proximate to coil 406. In an embodiment, MR element 404 may be placed between coil 406 and target 402. In other embodiments, the traces of coil 406 may be placed between MR element 404 and target 402 (not shown).

In the single coil configuration, MR element 404 may be subject to a magnetic field even in the absence of magnetic target 402. If magnetic target 402 is absent, there will be no eddy current and no reflected magnetic field. However, because MR element 404 is placed proximate to a single coil 406, and not placed between two opposing coils, it may be subject to a directly coupled magnetic field 405 produced by the coil 406.

The presence of target 402 may result in a reflected magnetic field and this additional field can be detected by MR element 404 to indicate the presence of target 402. For example, current through coil 406 may produce eddy currents (shown by currents 408 and 410) in target 402, which may produce reflected magnetic field 412. Reflected magnetic field 412 may increase the strength of the magnetic field experienced by MR element 404. Thus, when target 402 is present, MR element 404 may detect a stronger magnetic field than when target 402 is absent.

The proximity of target 402 may also increase or decrease the strength of the reflected magnetic field detected by MR element 404. As target 402 moves closer to coil 406 (or vice versa), the eddy currents (shown by currents 408' and 410') will increase in strength, which will produce a reflected magnetic field 412' with greater strength. Thus, MR element 404 will detect stronger magnetic field as target 402 moves closer to coil 406.

In the embodiment shown in FIG. 4, MR element 404 is positioned adjacent to loops of coil 406. This may result in greater sensitivity of MR element 404 to detect reflected field 412. However, because the field produced by coil 406 is not zero at the position of MR element 404, MR element 404 may also detect not only the reflected field, but also the magnetic field directly produced by the coil 406, i.e. a "directly coupled" magnetic field. Various techniques may be used to reduce MR element 404's sensitivity to the directly coupled magnetic field.

Figure 5:
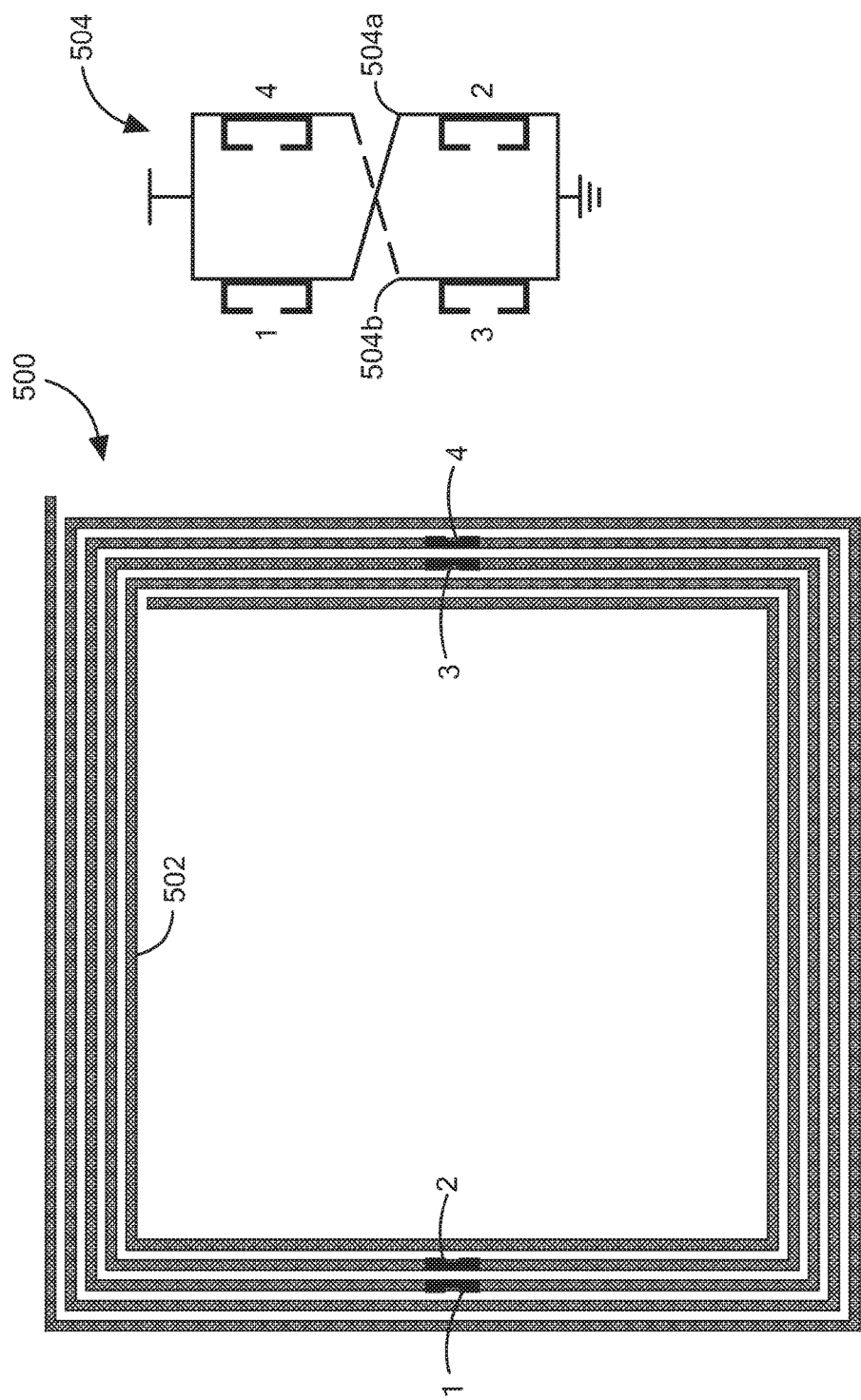
FIG. 5 is a schematic diagram of a coil and MR elements for sensing a target.

Referring to FIG. 5, circuit 500 includes a coil 502 and four MR elements 1-4 placed above or below traces of coil 502. The MR elements may be connected in a bridge configuration 504. The bridge configuration may provide a differential output consisting of signals 504a and 504b.

In embodiments, circuit 500 may be used as a single-coil circuit for detecting a target. For example, as a target approaches MR elements 1 and 2, output signal 504a may change, and as the target approaches MR elements 3 and 4, output signal 504b may change. MR elements 1-4 may be aligned so that, as the target approaches elements 1-4, output signal 504a increase in value and output signal 504b decreases in value, or vice versa. For example, in such embodiments, the field created by the coil near the elements 1 and 2 is opposite is sign compared to the field created by the coil near the elements 3 and 4. Hence the reflected fields are in opposite direction enhancing the sensitivity of the bridge differential output to the reflected field while suppressing the variation due to external common fields.

Figure 5A:
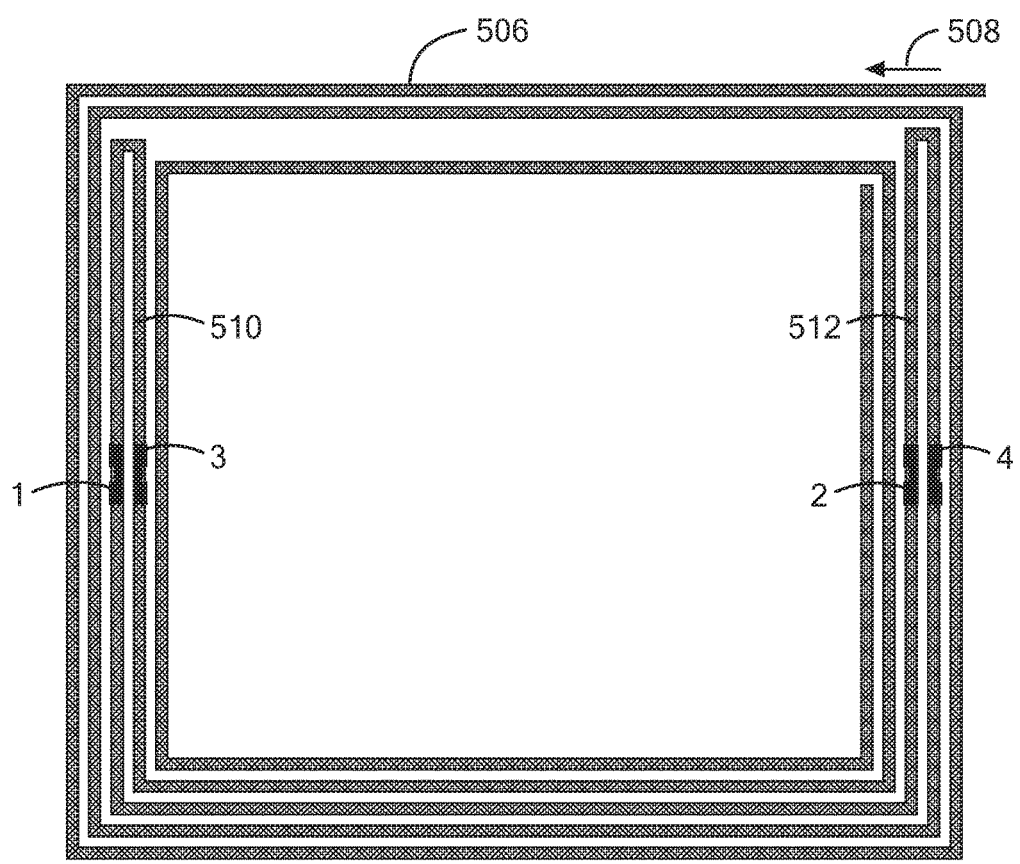
FIG. 5A is schematic diagram of an embodiment of a coil and MR elements for sensing a target.

Referring to FIG. 5A, circuit 500' includes a coil 506 arranged so that, if current flows through coil 506 in the direction shown by arrow 508, the current will flow through coil portion 510 in a clockwise direction and through a counter-loop coil portion 512 in a counterclockwise direction. Thus, coil portions 510 and 512 may produce local magnetic fields having opposite direction, as described above. MR elements 1-4 may be arranged as shown to form a bridge that provides a differential signal as the target approaches. The counter-loop may reduce the directly-coupled magnetic field produced by the coil and detected by the MR elements. For example, a magnetic field produced by coil 506 may be directly detected by (e.g. directly coupled to) MR elements 1-4. Coil portions 510 and 512 may each create a local magnetic field in the opposite direction of the magnetic field produced by coil 506. Thus, the local magnetic fields may (at least partially) cancel out the directly coupled field produced by coil 506 at least in the local area around MR elements 1-4. This may reduce or eliminate the directly-coupled field as detected by MR elements 1-4 so that the magnetic field detected by MR elements 1-4 is the reflected field from the target.

In embodiments, the counter-loop is used to measure reflected field and the direct field of the coil to provide sensitivity detection. Also, in this configuration, MR elements 1-4 can be placed so they do not see the field created by the main coil.

In embodiments, the target may be positioned adjacent to MR elements 1 and 3, but not 2 and 4 (or vice versa). If MR elements 1-4 are arranged in a bridge formation, a differential output of the bridge may change as the target moves toward or away from MR elements 1 and 3, for example.

In embodiments, the target may be positioned so that MR elements 1 and 2 experience the reflected magnetic field in one direction (e.g. experience one side of the reflected magnetic field) and MR elements 3 and 4 experience the reflected magnetic field in the opposite direction (e.g. experience the other side of the reflected magnetic field). In this embodiment, as the target moves closer to the MR elements, signal 504*a* may increase and signal 504*b* may decrease (or vice versa) to produce a differential signal.

Figure 5B:
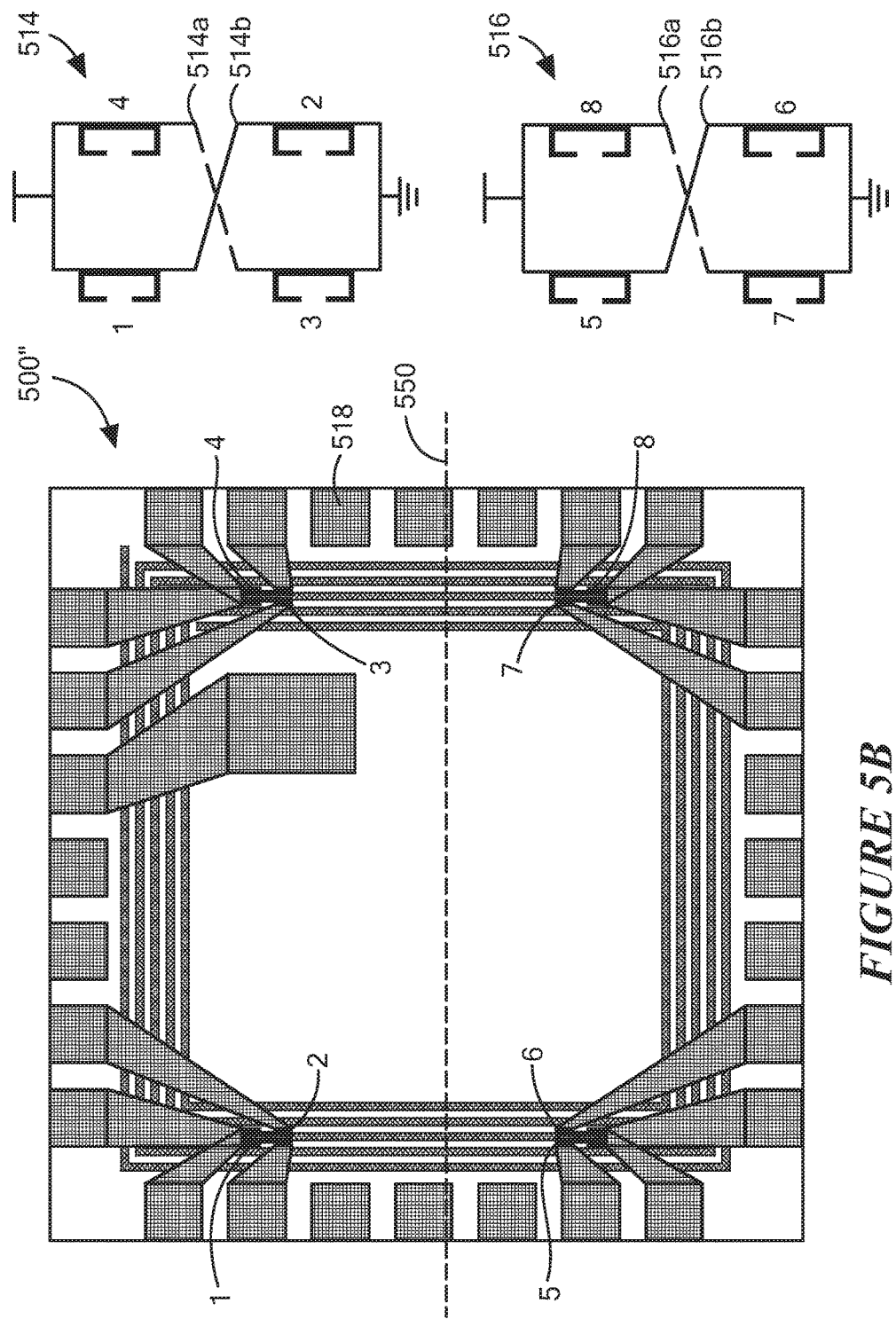
FIG. 5B is schematic diagram of an embodiment of a coil and MR elements for sensing a target, including a lead frame.

Referring to FIG. 5B, circuit 500" includes two MR bridges. MR bridge 514 includes MR elements 1-4 and produces a differential output signal consisting of signals 514*a* and 514*b*, whereas MR bridge 516 includes MR elements 508 and produces a differential output signal consisting of signals 516*a* and 516*b*. As a target approaches the MR elements 1-8, the output signals of MR bridges 514 and 516 may change to indicate the presence and proximity of the target. Circuit 500" is also shown with bond pads 518.

In an embodiment, the target may be positioned adjacent to bridge 514 (MR elements 1-4) so that the differential output of bridge 514 is affected as the target moves closer to or further from bridge 514. In this embodiment, the output of bridge 516 may remain relatively stable as the target moves. Thus, the output of bridge 516 may be used as a reference. In particular, this arrangement may work in situations where the target to be detected is relatively close to bridge 514, so that movement of the target has a greater effect on bridge 514 and a smaller or zero effect on bridge 516.

Additionally or alternatively, the same configuration can be used to measure a difference of distance, the first distance being between a large target and the lock of MR elements 1, 2, 3, and 4 and the second distance being between the corresponding target and MR elements 5, 6, 7, and 8.

Additionally or alternatively, the same configuration of FIG. 5B can be used to determine accurately the centering of a target along a plane perpendicular to the plane of the coil and crossing the plane of the coil along the line 530 situated at equal distance between the bridges 514 and 516.

Figure 5C:
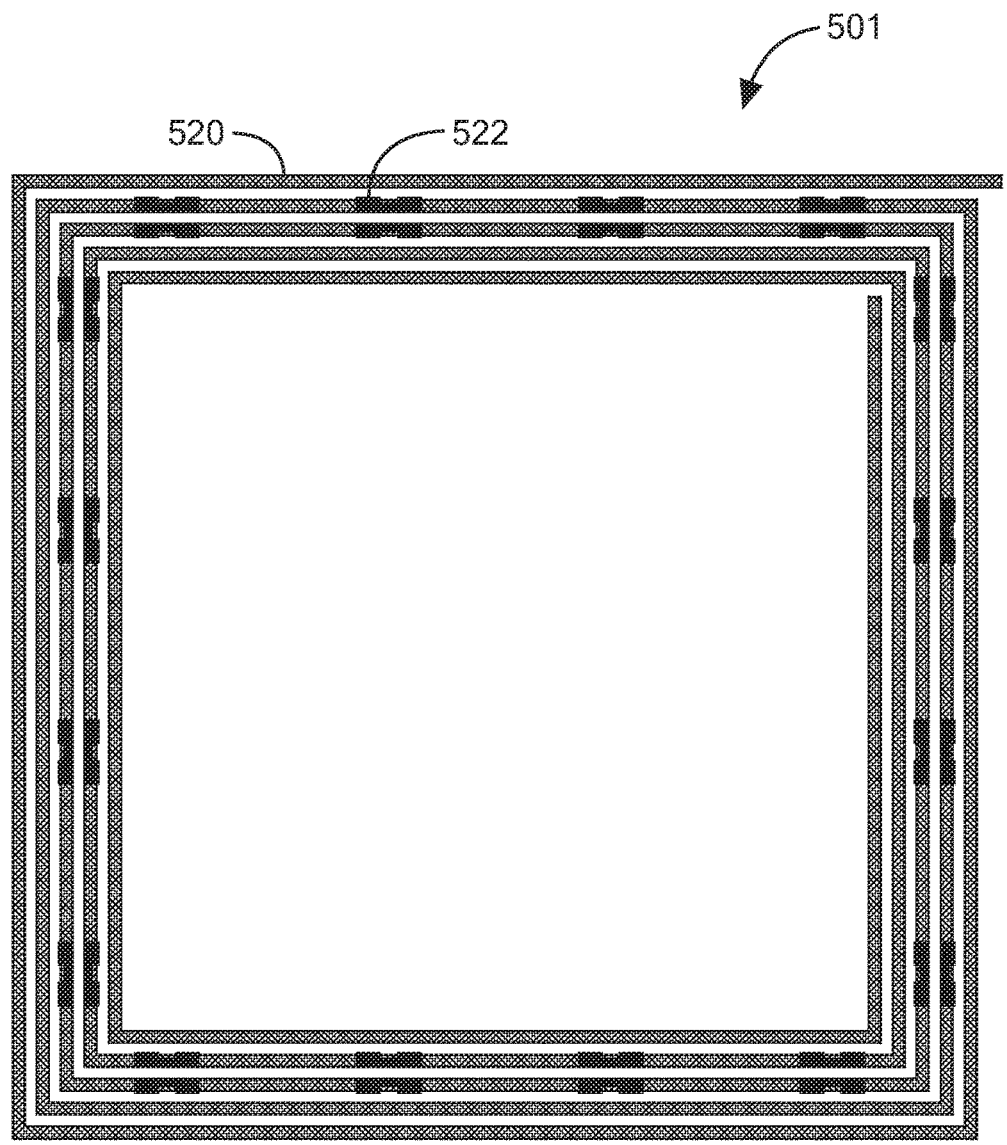
FIG. 5C is schematic diagram of an embodiment of a coil and MR elements for sensing a target.

Referring to FIG. 5C, circuit 501 includes a coil 520 and multiple MR elements 522 arranged at intervals around coil 520. MR elements 522 may form a grid, similar to the grid described above and shown in FIG. 3B. In embodiments, MR elements 522 may be connected in bridge configurations. In other embodiments, MR elements 522 may act (or be part of) individual circuits that are not shared with other MR elements. In either case, MR elements 522 may produce a signal when a target (and its reflected magnetic field) are detected. A processor may receive these signals and calculate the location, position, speed, parallelism, angle or other properties of the target.

In an embodiment, circuit 501 may be used to detect the position of the target in three dimensions with respect to the coil. Because the MR elements are positioned in a plane along coil 520, they may act as a grid. As the target approaches one (or more) of the MR elements, they will produce an output signal that can be used to determine the location of the target along the two dimensions of the grid. Also, as described above, coil 520 and the MR elements may be used to detect distance from the MR elements in a direction orthogonal to the two dimensions of the coil and grid (i.e. a direction into and out of the page).

Figure 6:
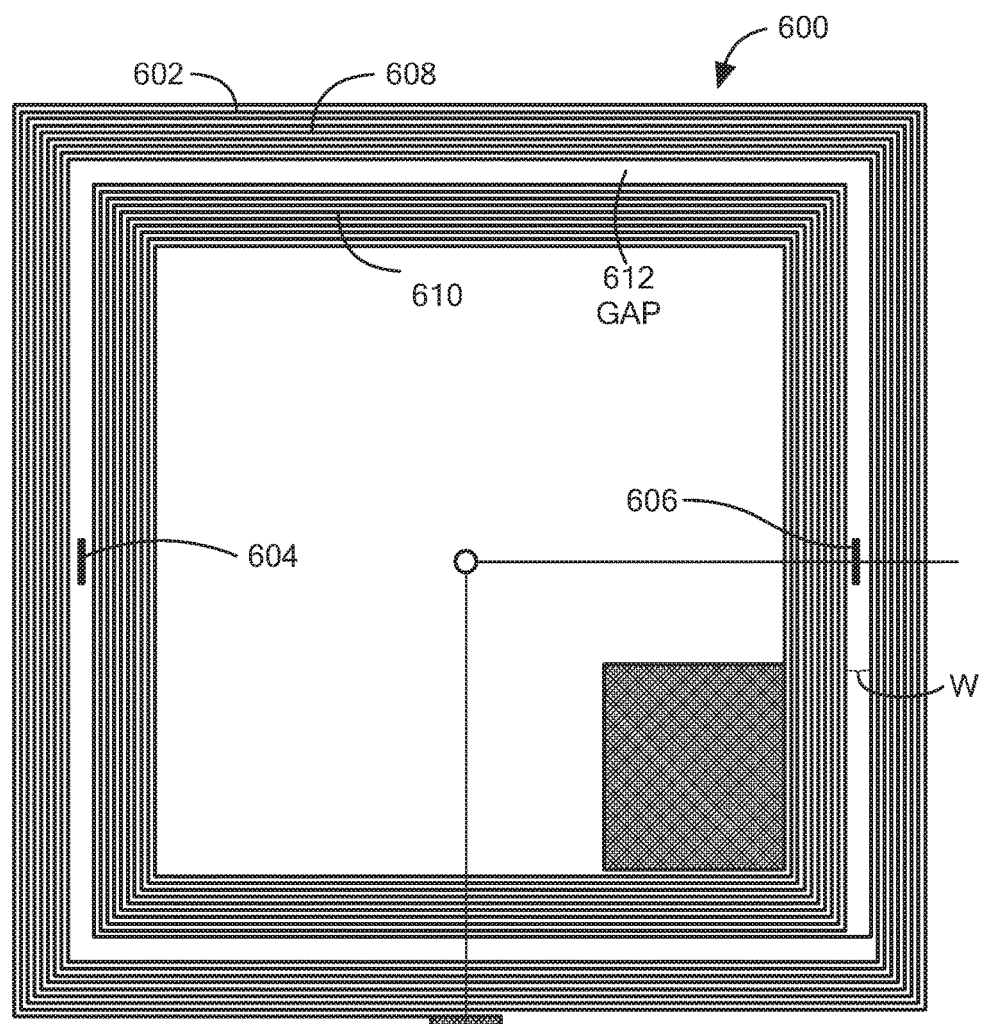
FIG. 6 is schematic diagram of an embodiment of a coil and MR elements for sensing a target.

Referring now to FIG. 6, a circuit 600 for detecting a target may include a coil 602 and one or more MR elements 604 and 606. Coil 602 may have two coiled portions 608 and 610, separated by a gap 612. In embodiments, the current through portions 608 and 610 flows in the same direction. For example, if the current through portion 608 flows in a clockwise direction around the coil, the current through portion 610 may also flow in a clockwise direction.

MR elements 604 and 606 may be placed within the gap so that they are not directly above (or below) traces of coil 602. Placing MR elements within gap 612 may reduce capacitive or inductive coupling between coil 602 and MR elements 604 and 606. Also, gap 612 may have a width W that is smaller than the distance between the MR elements and the target. As a result of gap 612 being relatively small, the eddy currents induced in the target and the resulting reflected magnetic field may appear (i.e. may be detected by the MR elements) as if a single coil without any gap between portions were producing the magnetic field.

In embodiments, positioning MR elements within gap 612 may reduce sensitivity of the MR elements to the directly coupled magnetic field produced by gap 612, thus allowing the MR elements to maintain sensitivity to the reflected field.

In other embodiments, coil 602 may include a jog in one or more of the traces. MR elements 604 and 606 may be aligned with the jog.

Figure 7:
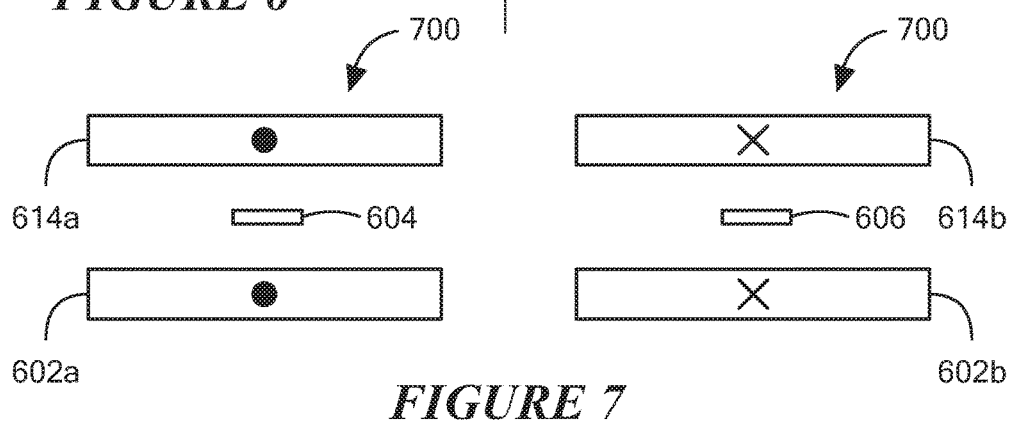
FIG. 7 is a cross-sectional view of coils and MR elements for sensing a target.

FIG. 7 is a cross-sectional view of a circuit having MR elements 604 and 606 sandwiched between traces of coil 700. In an embodiment, coil 700 may be the same as or similar to coil 602. Coil traces 602*a* and 602*b* may be positioned on the surface of a substrate (not shown). MR elements 604 and 606 may be placed atop traces 602*a* and 602*b* so that traces 602*a* and 602*b* are positioned between MR elements 604 and 606 and the substrate. An additional layer of traces 614*a* and 614*b* may be positioned atop MR elements 604 and 606. Traces 602*a*, 602*b*, 614*a*, and 614*b* may be part of the same coil so that current flowing through the traces flows in a circular or spiral pattern to induce a magnetic field. Placing MR elements 604 and 606 between traces of the coil may reduce directly coupled magnetic field produced by the coil.

Figure 8:
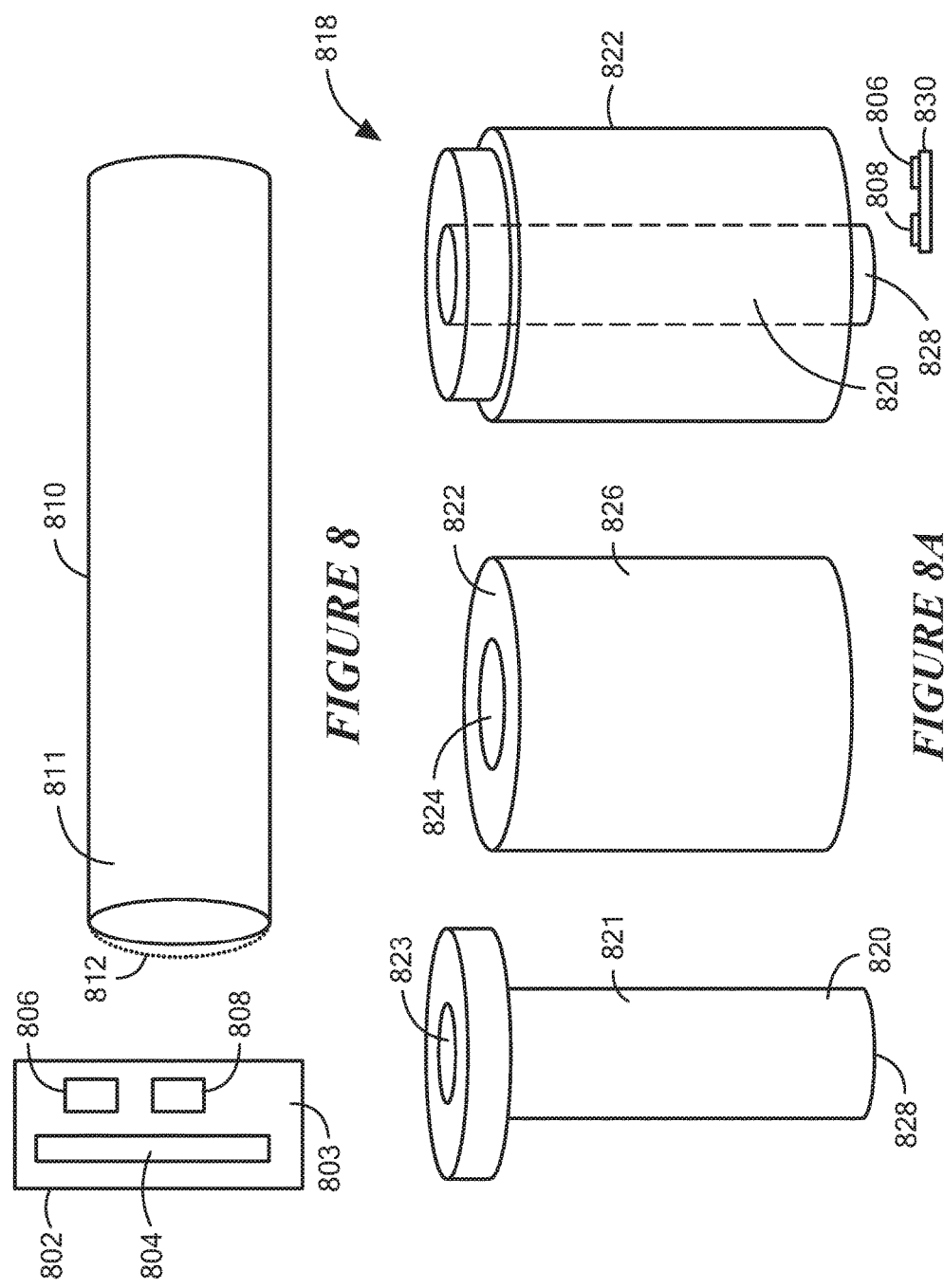
FIG. 8 is an isometric view of a pressure sensor.

Referring to FIG. 8, a pressure sensor 800 includes a magnetic field sensor 802, having a substrate 803 that supports a coil 804 and MR elements 806 and 808. In embodiments, magnetic field sensor 802 may be the same as or similar to circuit 500 in FIG. 5, circuit 300 in FIG. 3, or any of the magnetic field detection circuits described above that can detect proximity of a target.

In embodiments, coil 804 and MR elements 806, 808 may be supported by the same substrate 803. In other embodiments, MR element 806, MR element 808, and coil 804 may be supported on different substrates (not shown). For example, coil 804 may be supported by one substrate while MR elements 806 and 808 may be supported by a different substrate. In another example, MR element 806, MR element 808, and coil 804 may each be supported by a separate substrate. Any other combinations of substrates supporting circuit elements are also possible.

Pressure sensor 800 includes a chamber 810 having a conductive portion 811 and a deformable portion 812. In an embodiment, chamber 810 is formed by an elongate tube. In the embodiment of FIG. 8, the conductive portion and the deformable portion 812 may comprise a membrane disposed at one end of the tube that can act a diaphragm, and can be deformed to move toward or away from magnetic field detection circuit 802.

Deformable portion 812 may be formed of stainless steel, copper beryllium, titanium alloys, super alloys, and/or sapphire. When the pressure inside chamber 810 is greater than the pressure outside chamber 810, deformable portion 812 may extend toward magnetic field detection circuit 802. If the pressure outside chamber 810 is greater, deformable portion 812 may retract away from magnetic field detection circuit 812, and if the pressure inside and outside chamber 810 is in equilibrium, deformable portion may adopt a neutral position between the extended and retracted positions.

In case of a circular deformable portion, the deformation of the membrane is given by the formula:

$$d = \frac{3}{16} \frac{p}{Eh^3} (1-v^2)(a^2-r^2)^2$$

Where h is the thickness of the deformable portion, v is the Poisson module, E is the young module, a is the radius of the deformable portion, r is the point where the deformation is measured.

In embodiments, the maximal deformation may be low enough that the deformable portion is always in the elastic domain of the material even at temperature above 180° C. For that reason, super alloys like maraging alloys or titanium alloys may be suitable materials.

Magnetic field detection circuit 802 may include at least one magnetic field sensing element 806 and/or 808 disposed proximate to coil 804, as described above. Coil 804 may produce a magnetic field that induces eddy current and a reflected magnetic field in the conductive portion 812, similar to the eddy currents and reflected fields described above. Magnetic field detection circuit 802 may also include a circuit to generate an output signal indicative of the pressure differential between the interior and exterior of chamber 810.

In embodiments, magnetic field detection circuit 802 comprises two spaced apart MR elements 806 and 808 and detects a distance between the conductive portion 812 and one of the MR elements 806 and 808 as deformable portion extends toward and/or retracts away from the MR elements. In embodiments, magnetic field detection circuit 802 may be configured to detect a difference between a) the distance between the conductive portion 812 and magnetic field sensor 808, and b) the distance between conductive portion 812 and magnetic field sensor 806. The difference between these distances may be used to produce an output signal of magnetic field detection circuit 802.

The output signal produced by magnetic field detection circuit 802 may represent the distance, which can then be received by a processor to calculate an associated pressure within chamber 810. MR elements 806 and 808 may comprise multiple MR elements and may be arranged in a bridge configuration, as described above, to produce a differential output.

In an embodiment, MR element 806 is aligned with an edge of conductive, deformable portion 812 and MR element 808 is aligned with the center or a central region of conducive, deformable portion 812. In this arrangement, MR element 808 will react as deformable portion 812 moves toward and away from MR element 808, and MR element 806 will not be affected or will be affected to a significantly lesser degree than element 808, and thus may have a relatively constant resistance value. Positioning the MR elements in this way may be used to remove errors due to stray field. It may also help compensate for air gap tolerance between MR elements. For example, the difference in distance detected by the two sensors may be used to compensate for small changes in air gap over time, temperature, etc.

Referring to FIG. 8A, another embodiment of a pressure sensor 818 includes a first elongated tube 820 having a deformable sidewall 821 and an opening 823 that allows a fluid to enter a chamber within elongated tube 820. As the fluid creates pressure within tube 820, the sidewall 821 may expand like a balloon or extend. An end 828 of tube 820 may be conductive.

Pressure sensor 818 also includes a second elongated tube 822 having an opening 824. Elongated tube 822 may have a rigid wall 826, and an opening 824. Opening 824 may have a diameter or size large enough for tube 820 to be inserted into opening 824.

Pressure sensor 818 may include a magnetic field sensor 830, which may be the same as or similar to magnetic field sensor 802, and/or any of the magnetic field sensors described above.

In embodiments, when the tubes 820, 822 are assembled, conductive end 828 of tube 820 may be positioned proximate to MR element 808. As the pressure within tube 820 increases and decreases, the rigid wall of tube 822's may keep deformable sidewall 821 from expanding laterally. However, end 828 may expand and extend toward MR element 808 and retract away from MR element 808 as pressure within tube chamber 823 changes. Magnetic field sensor 830 may detect the change in distance and produce an output signal representing the distance between end 828 and MR element 808. In embodiments, magnetic field detection circuit 802 may be configured to detect a difference between a) the distance between conductive end 828 and magnetic field sensor 808, and b) the distance between conductive 808 and magnetic field sensor 806. The difference between these distances may be used to produce an output signal of magnetic field detection circuit 830. A processor circuit may receive the signal and calculate a pressure within tube 820 based on the distance.

Figure 9:
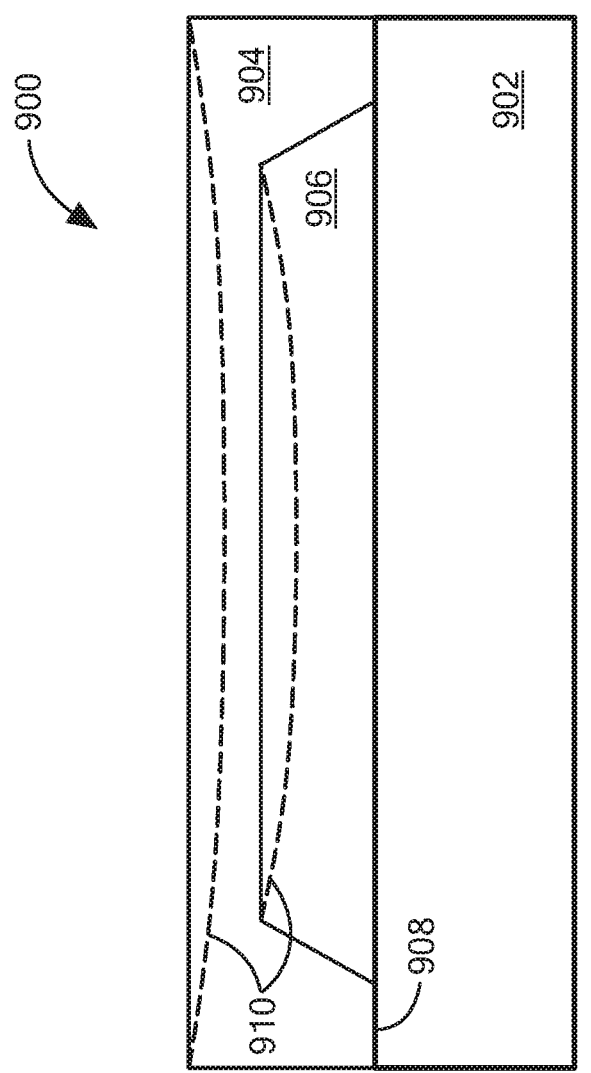
FIG. 9 is a cross-sectional view of an embodiment of a pressure sensor including substrates.

Referring also to FIG. 9, pressure sensor 900 includes a first substrate 902, that may be the same or similar to substrate 803 of FIG. 8, and a second substrate 904 attached to the first substrate 902. Second substrate 904 may include a surface 908 and recess 906 formed in the surface. Recess 906 may be etched into the substrate. In embodiments, wafer 904 may be etched so that it is thin enough to deflect under pressure, as shown by dotted lines 910. MR elements supported by substrate 902 may detect (via a reflected magnetic field as describe above) the deflection of wafer 904. The detected deflection may be subsequently correlated to a pressure.

In embodiments, the MR elements on substrate 902 may be positioned so that one or more MR elements are adjacent to an edge (e.g. a non-deflecting portion) of recess 906 and one or more MR elements are adjacent to the center (e.g. a deflecting portion) of recess 906, similar to the arrangement described above and illustrated in FIG. 8A.

In embodiments, substrate 904 may be formed from a conductive material, for example copper. Therefore, motion of a conductive deformable portion of substrate 904 caused by pressure on substrate 904 (and/or pressure within recess 906) can be detected by a magnetic field sensors on substrate 902.

Alternatively the substrate 904 may be formed by a crystalline material like sapphire coated by a thick enough conductive material like copper for example.

In embodiments, recess 906 is evacuated during the manufacturing process to determine a reference pressure. In embodiments, the reference pressure is a vacuum or a pressure that is less than standard pressure (e.g. less than 100 kPa). In certain configurations, one or more of the output signals of an MR bridge (e.g. bridge 318 in FIG. 3A) may be used to generate to represent the value of the reference pressure.

Figure 10:
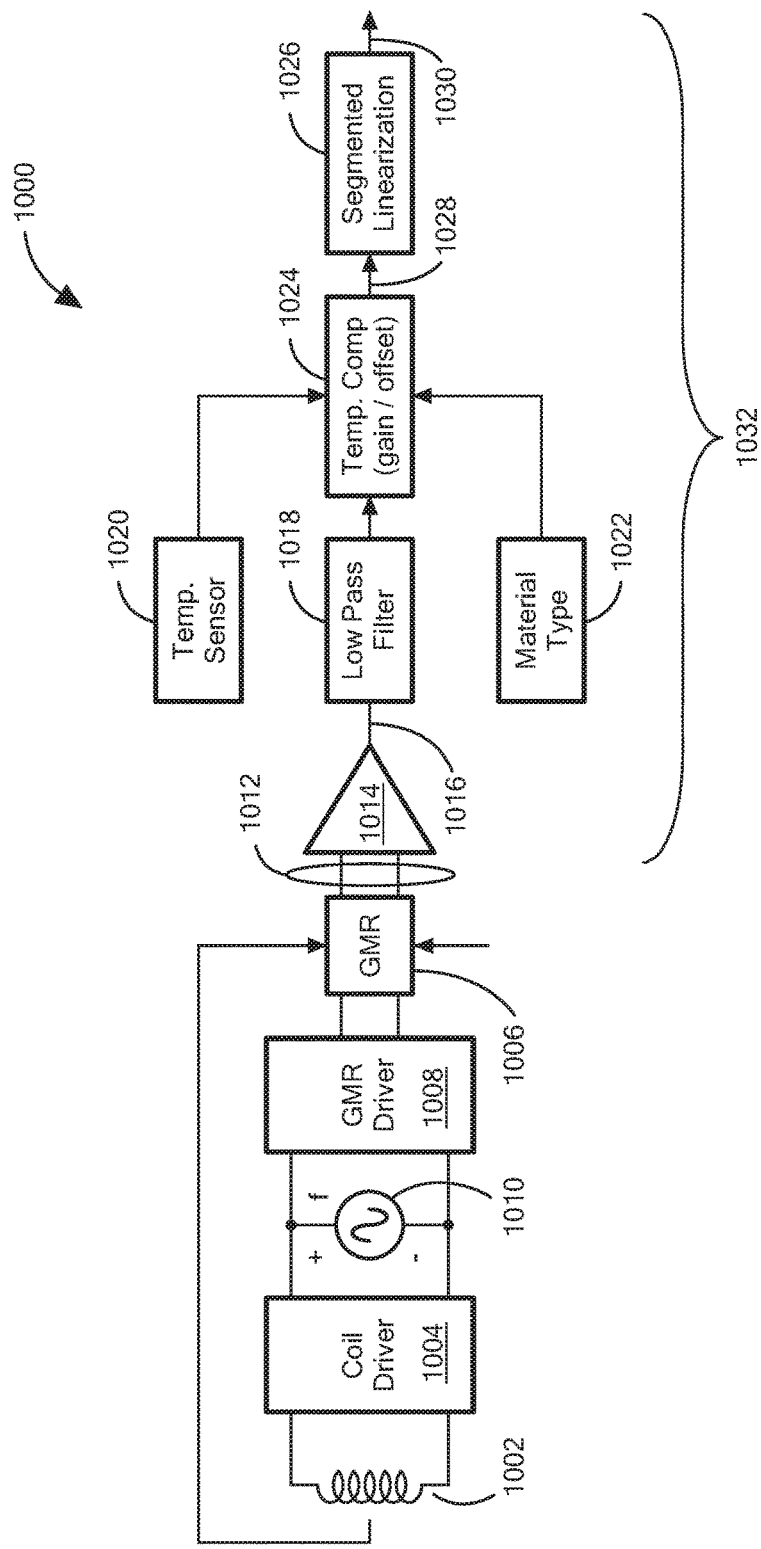
FIG. 10 is a block diagram of a circuit for sensing a magnetic target.

Referring to FIG. 10, a block diagram of a magnetic field sensor 1000 is shown. Magnetic field sensor includes a coil 1002 to produce a magnetic field, coil driver 1004 to provide power to the coil, MR element 1006, and MR driver circuit 1008 to provide power to MR element 1006. MR element 1006 may be a single MR element or may comprise multiple MR elements, which may be arranged in a bridge configuration. As described above, coil 1002 and MR element 1006 may be configured to detect the distance of a conductive target. In embodiments, coil driver 1004 and/or MR driver 1008 may produce an AC output to drive coil 1002 and MR element 1008, as described above and as indicated by AC source 1010. AC source 1010 may be a common source used to drive both coil 1002 and MR element 1006. In embodiments, signal 1012 may be an AC signal.

Magnetic field sensor 1000 also includes an amplifier to amplify the output signal 1012 of MR element 1006. Output signal 1012 may be a differential signal and amplifier 1014 may be a differential amplifier. Output signal 1012 and amplified signal 1016 may a DC signal.

Magnetic field sensor 1000 may also include a low pass filter 1018 to filter noise and other artifacts from signal 1016, and an offset module 1024 which may scale the output signal according to temperature (e.g. a temperature measure by temperature sensor 1020) and a type of material according to material type module 1022. A segmented linearization circuit 1026 may also be included, which may perform a linear regression on compensated signal 1028 and produce output signal 1030.

In embodiments, the reflected magnetic field from the target will have a frequency f (the same frequency as the coil driver 1004). Because the magnetic field produced by coil 1002 and the reflected field have the same frequency, the output of MR element 1006 may include a 0 Hz (or DC) component, a component at frequency f, and harmonic components at multiples of frequency f. One skilled in the art will recognize that the lowest frequency harmonic component may occur at frequency 2*f. However, any difference in the equilibrium of the MR bridge may generate a frequency component that may be present in the signal. Thus, low pass filter 1018 may be configured to remove the frequency f and higher (i.e. low pass filter 1018 may include a cut-off frequency $f_{cutoff}$, where $f_{cutoff} < f$. In embodiments, the filter may be designed to remove possible f signals. Accordingly, the frequency f may be chosen as a frequency greater than the frequency range of motion of the target.

In embodiments, the sensitivity of MR element 1008 changes with temperature. The strength of the reflected field may also change with temperature depending of target material type and frequency. To compensate, module 1022 may contain parameters to compensate for the effects of the temperature and/or material used. The parameters may include linear and/or second order compensation values.

In embodiments, processing circuit 1032 may process the signal representing the magnetic field. Because a common source 1010 is used to drive MR element 1006 and coil 1002, the frequency of coil 1002 and MR element 1006 is substantially the same. In this case, post processing of the signal may include filtering, linear regression, gain and amplification, or other signal shaping techniques.

MR element 1006 may detect the magnetic field directly produced by coil 1002 and also the reflected magnetic field produced by eddy currents in a conductive target, induced by the magnetic field generated by current through coil 1002.

Figure 10A:
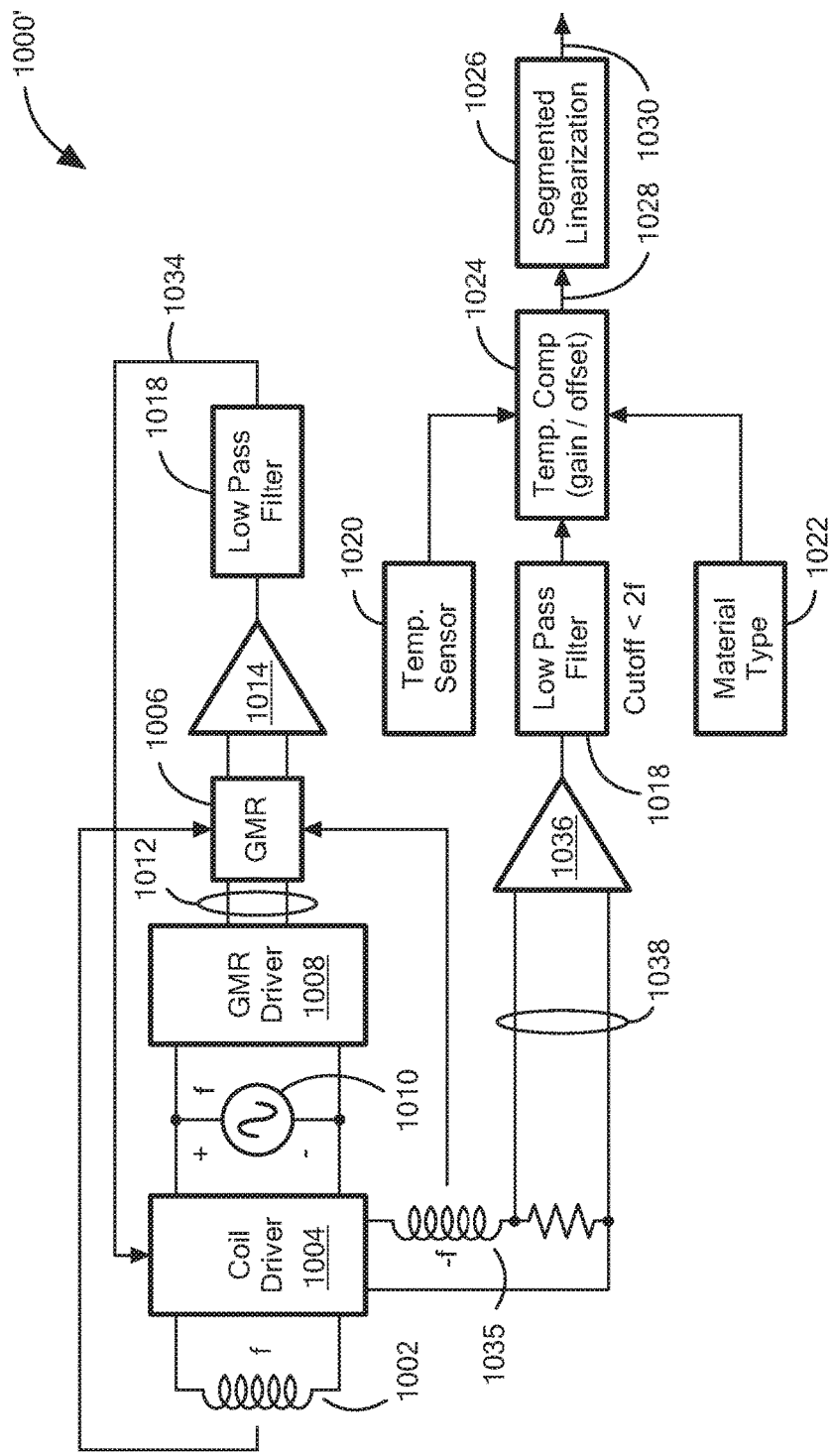
FIG. 10A is a block diagram of an embodiment of a circuit for sensing a magnetic target.

Referring to FIG. 10A, magnetic field sensor 1000' may include coil 1002, coil driver 1004, common AC source 1010, MR driver 1008, MR element 1006, amplifier 1014, and low pass filter 1018 as described above.

Magnetic field sensor 1000' may differ from sensor 1000 of FIG. 10 in that it is a closed loop sensor and so may also include a second coil 1035, which may operate at a different AC frequency than coil 1002. In this example, coil 1035 may be 180 degrees out of phase with coil 1002 as indicated by the "-f" symbol. Coil 1035 may also produce a first magnetic field that can be used to detect a target. In embodiments, coil 1035 may be relatively smaller than coil 1002. Coil 1035 may be placed adjacent to MR element 1006 to produce a magnetic field that can be detected by MR element 1006, but which does not produce eddy currents in the target.

In embodiments, coil 1035 may be used to offset errors due to the magnetoresistance of the MR element. For example, the magnitude of current driven through coil 1035 may be changed until the output of MR element 1006 is zero volts. At this point, the current through coil 1035 may be measured (for example, by measuring voltage across a shunt resistor in series with coil 1035). The measured current may be processed similarly to the output of MR element 1006 to remove a magnetoresistance error associated with MR 1006.

Magnetic field sensor 1000' may also include an amplifier 1036 to receive signal 1038. Magnetic field sensor 1000' may also include low pass filter 1019, material type module 1022, temperature sensor 1020, offset module 1024, and segmented linearization module 1026 as described above.

Figure 11:
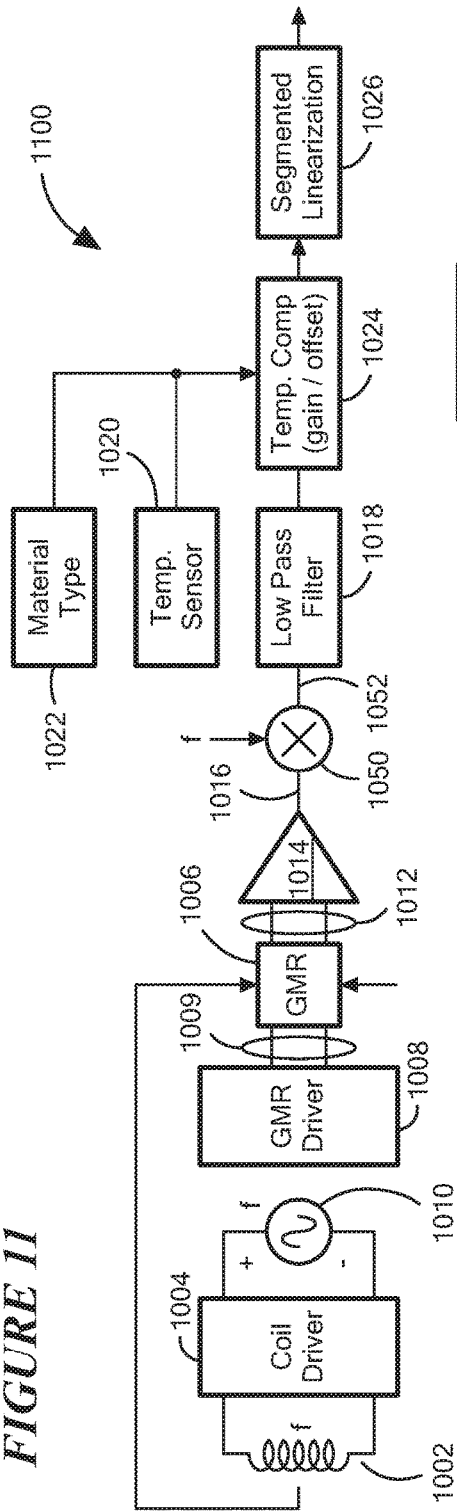
FIG. 11 is a block diagram of an embodiment of a circuit for sensing a magnetic target.
Figure 11A:
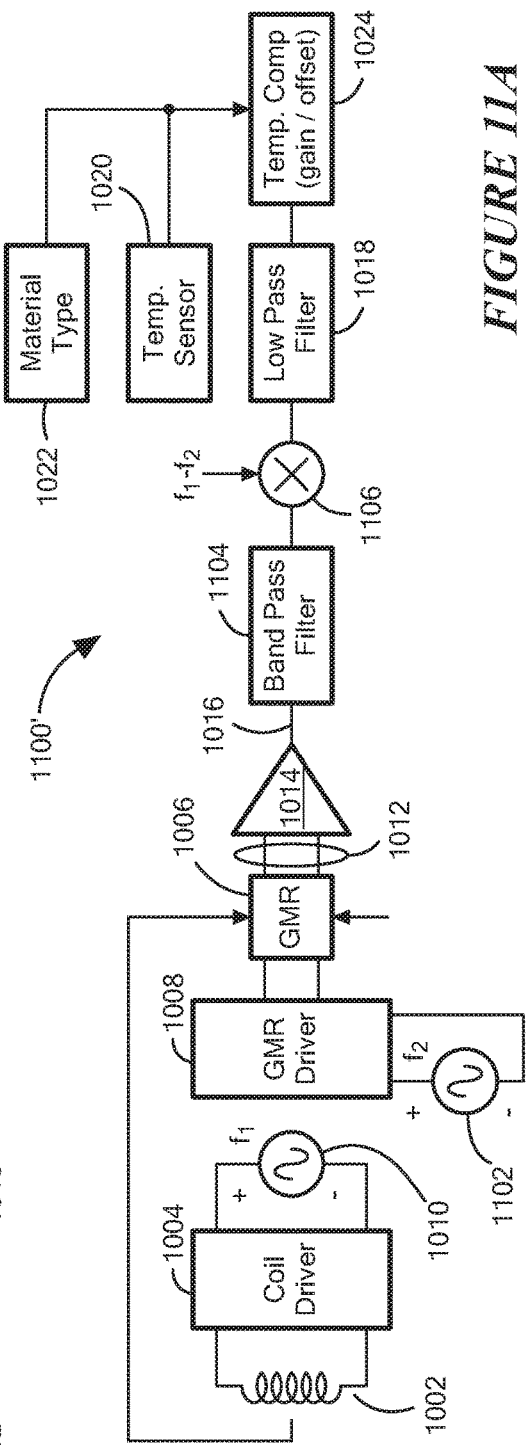
FIG. 11A is a block diagram of an embodiment of a circuit for sensing a magnetic target.
Figure 11B:
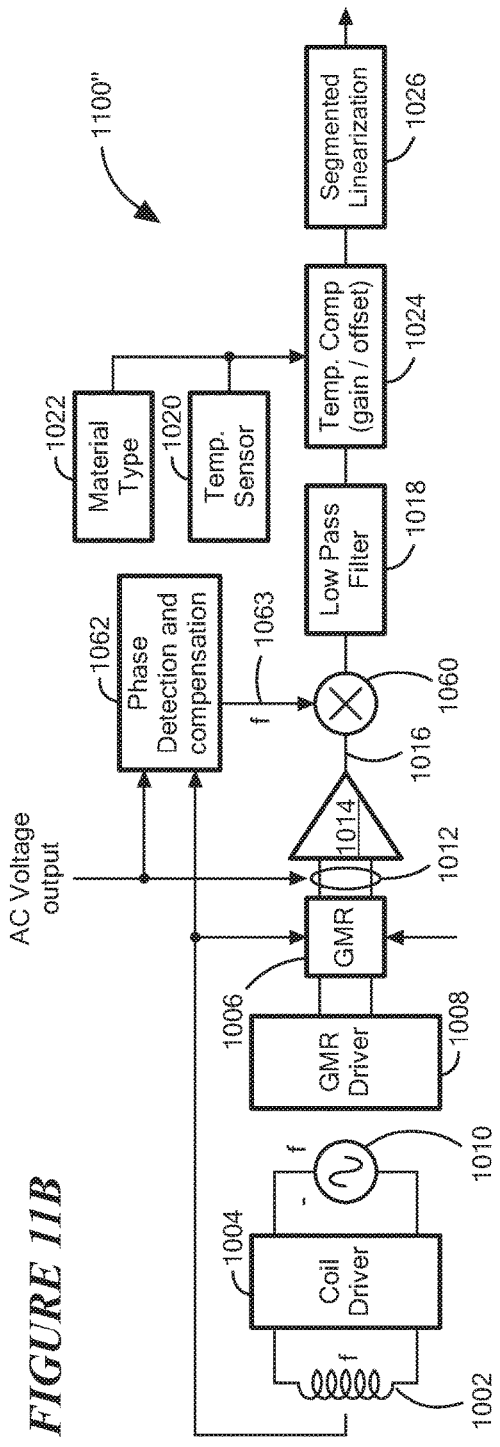
FIG. 11B is a block diagram of an embodiment of a circuit for sensing a magnetic target.
Figure 11C:
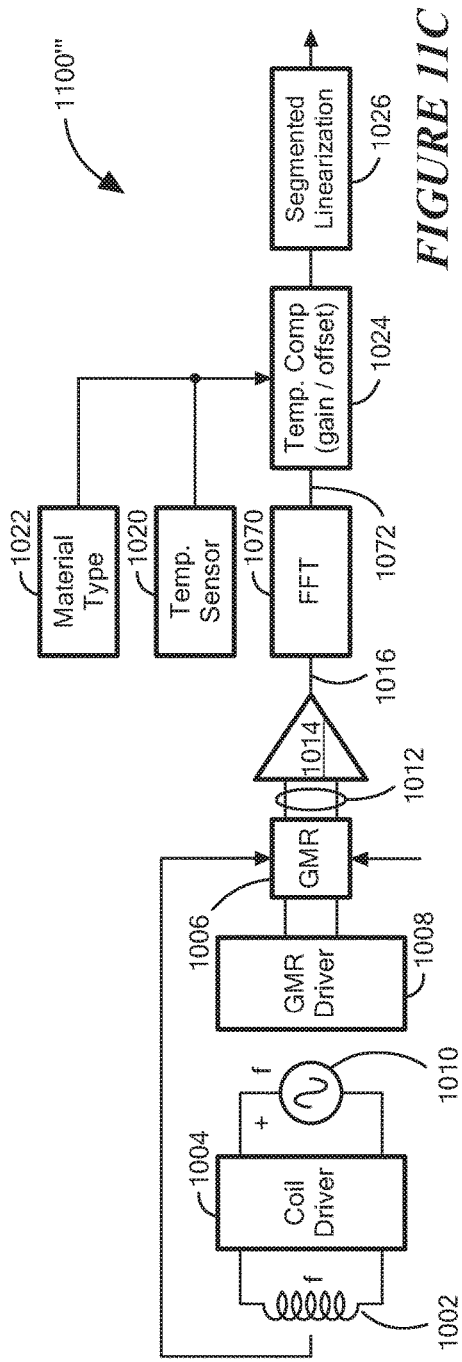
FIG. 11C is a block diagram of an embodiment of a circuit for sensing a magnetic target.
Figure 11D:
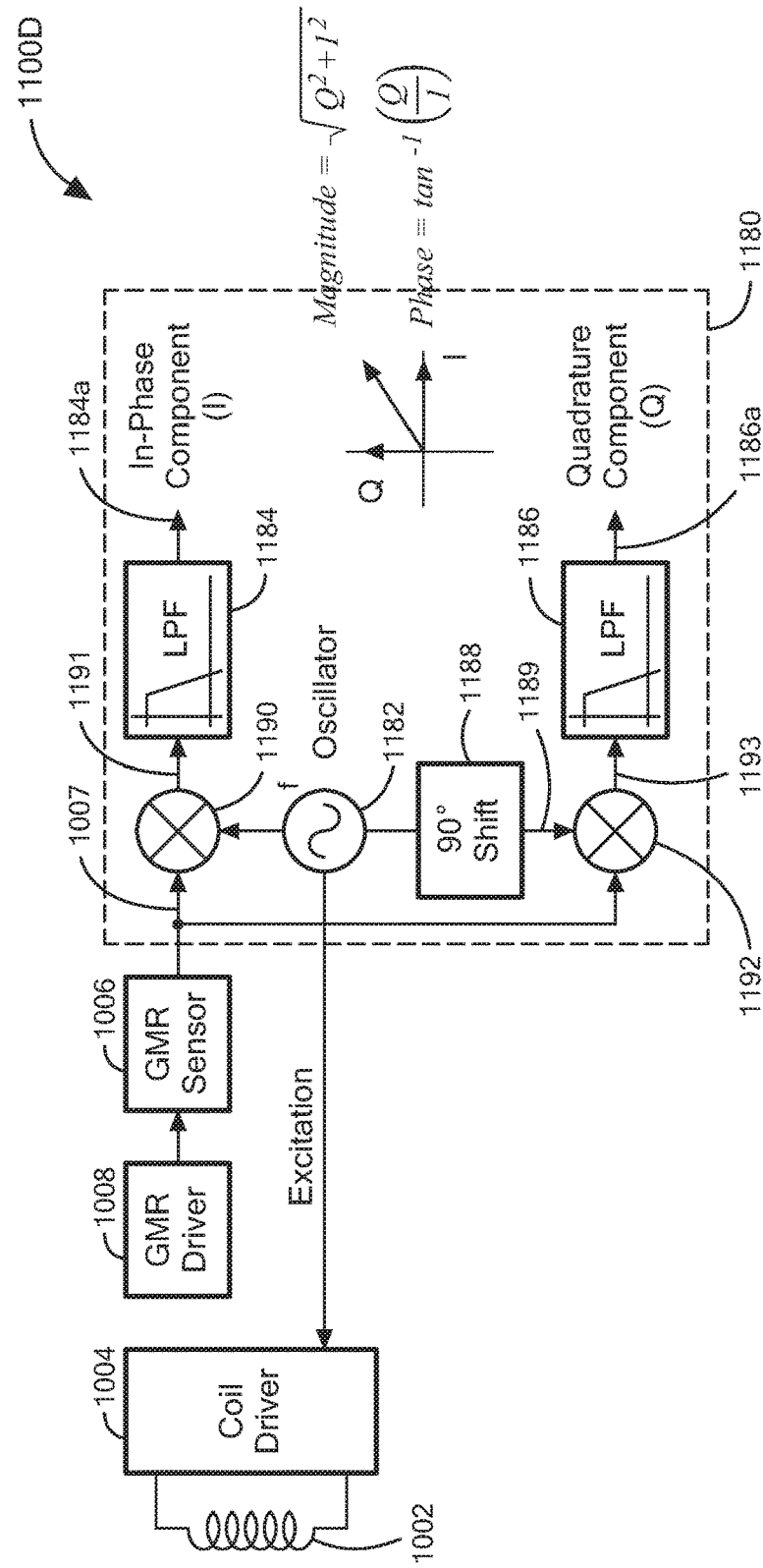
FIG. 11D is a block diagram of an embodiment of a circuit for sensing a magnetic target.
Figure 11E:
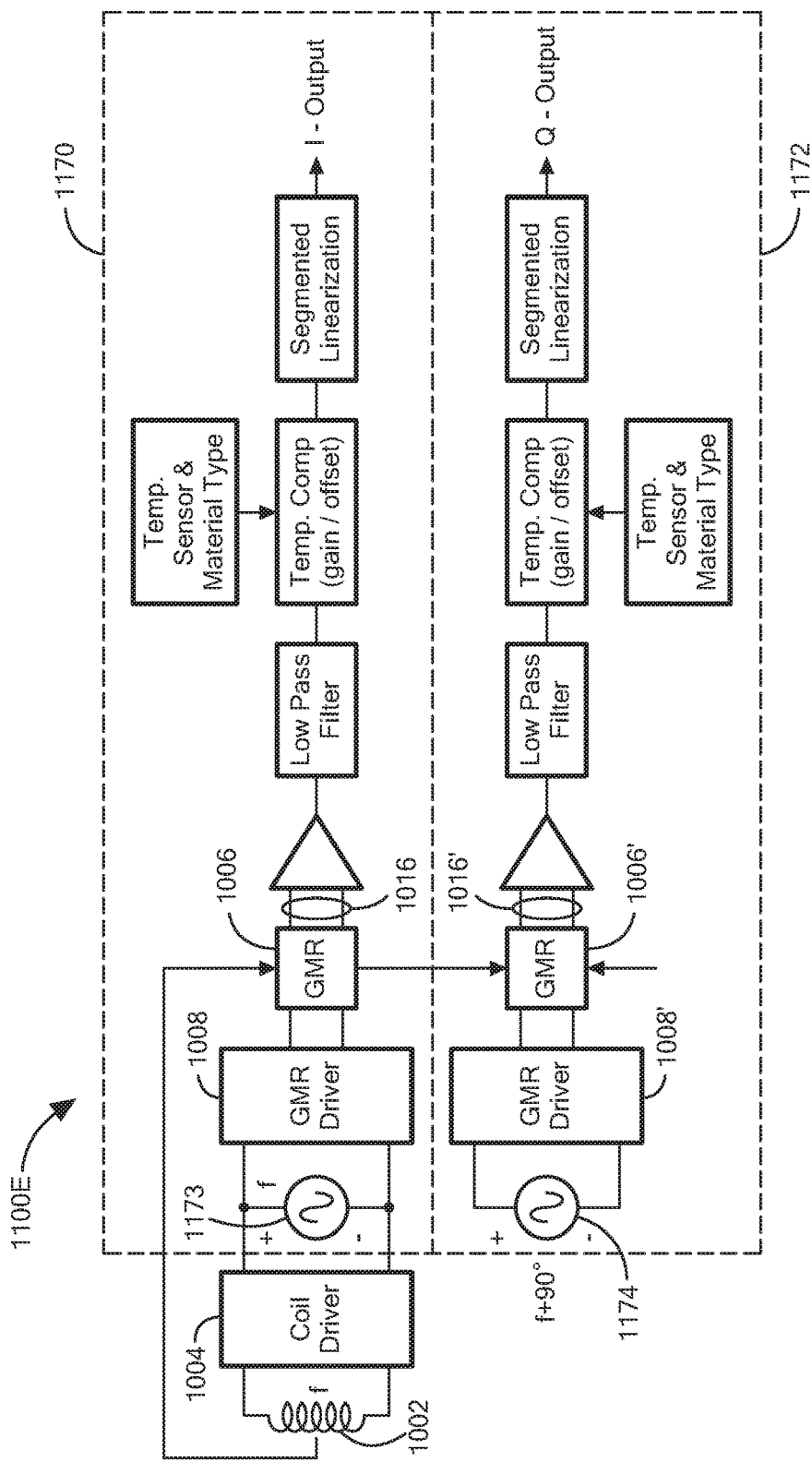
FIG. 11E is a block diagram of an embodiment of a circuit for sensing a magnetic target.
Figure 11F:
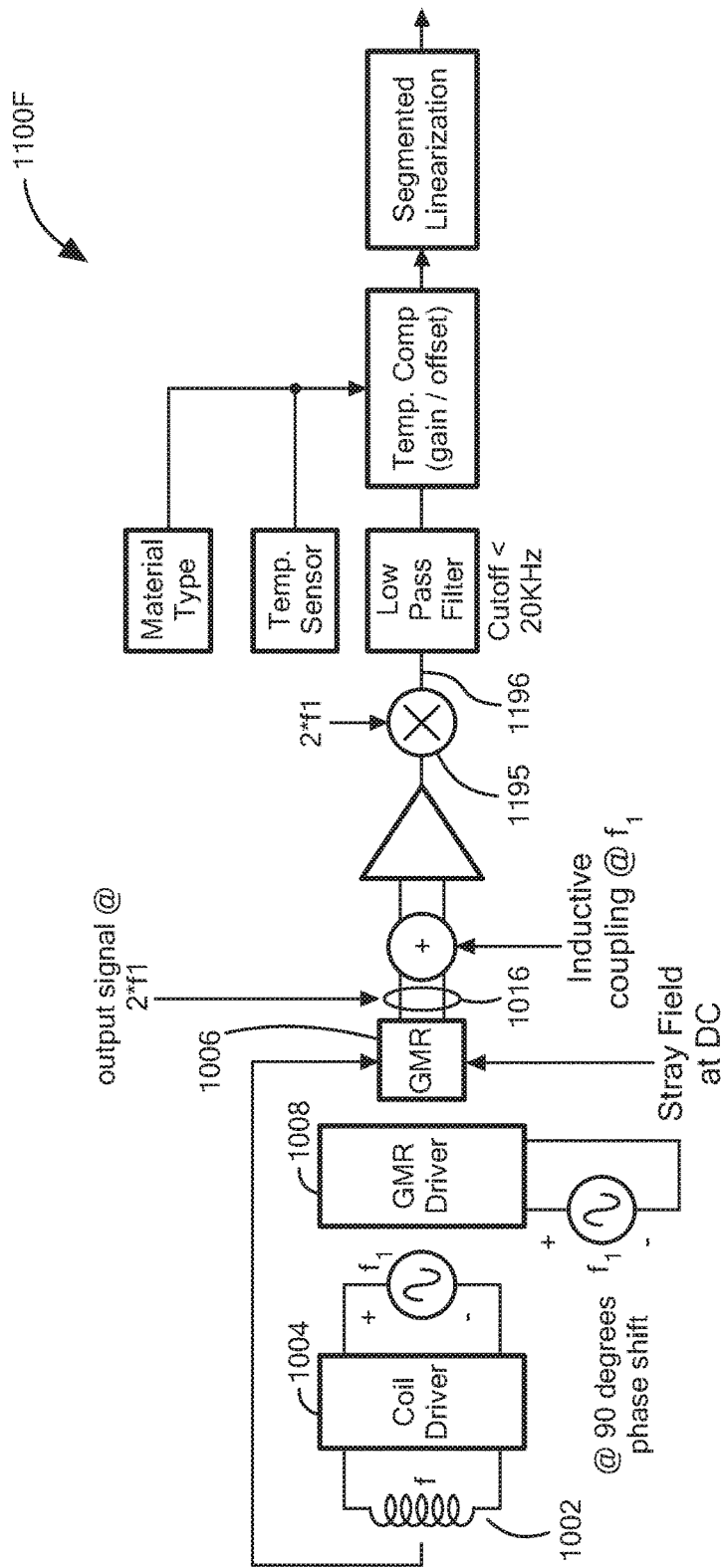
FIG. 11F is a block diagram of an embodiment of a circuit for sensing a magnetic target.

FIGS. 11-11F include various examples of magnetic field sensors having signal processing to reduce inductive coupling or other noise from affecting signal accuracy. The example magnetic field sensors in FIGS. 11-11F may also employ various features related to detecting a reflected field from a target, such as frequency hopping, etc. Such magnetic field sensors may also include circuitry to compute a sensitivity value.

Referring now to FIG. 11, a magnetic field sensor 1100 may include coil 1002, coil driver 1004, AC driver 1010, MR driver 1008, MR element 1006, amplifier 1014, low pass filter 1018, temperature sensor 1020, material type module 1022, offset module 1024, and segmented linearization module 1026.

MR element 1006 may be responsive to a sensing element drive signal and configured to detect a directly-coupled magnetic field generated by coil 1002, to produce signal 1012 in response. Processing circuitry may compute a sensitivity value associated with detection, by MR element 1006, of the directly-coupled magnetic field produced by coil 1002. The sensitivity value may be substantially independent of a reflected field produced by eddy currents in the target.

As shown, AC driver 1010 is coupled to coil driver 1004, but is not coupled to MR driver 1008 in sensor 1100. In this embodiment, MR driver 1008 may produce a DC signal (e.g. a signal with a frequency of about zero) to drive MR element 1006.

Coil 1002 may produce a DC (or substantially low frequency AC) magnetic field that can be detected by MR element 1006, but which does not produce eddy currents in the target. The signal produced by detection of the DC (or substantially low frequency AC) magnetic field may be used to adjust sensitivity of the magnetic field sensor.

Coil 1002 may also produce an AC magnetic field at higher frequencies that induces eddy currents in the target, which produce a reflected magnetic field at those higher frequencies that can be detected by MR element 1006.

MR element 1006 may produce signal 1012, which may include frequency components at the DC or substantially low AC frequency (e.g. a "directly coupled" signal or signal component) representing the lower frequency magnetic field that does not cause eddy currents in the target, and/or frequency components at the higher AC frequency (e.g. a "reflected" signal or signal component) that represent the detected reflected field. The directly coupled signals may be used to adjust sensitivity of the sensor while the reflected signals may be used to detect the target. Coil driver 1004 and/or MR driver 1008 may use the directly coupled signals as a sensitivity signal adjust their respective output drive signals in response to the sensitivity signal.

In embodiments, the directly coupled signal and the reflected signal may be included as frequency components of the same signal. In this case, coil 1002 may be driven to produce both frequency components at the same time. In other embodiments, generation of the directly coupled signal and the reflected signals may be generated at different times, for example using a time-division multiplexing scheme.

Sensor 1100 may also include a demodulator circuit 1050 that can modulate signal 1016 to remove the AC component from the signal or shift the AC component within the signal to a different frequency. For example, demodulator circuit 1050 may modulate signal 1016 at frequency f. As known in the art, because signal 1016 includes signal components at frequency f representing the detected magnetic field, modulating signal 1016 at frequency f may shift the signal elements representing the detected magnetic field to 0 Hz or DC. Other frequency components within signal 1016 may be shifted to higher frequencies so they can be removed by low-pass filter 1018. In embodiments, the DC or low frequency component of signal 1016, which may represent a sensitivity value, can be fed back to coil driver 1004 to adjust the output of coil 1002 in response to the signal, and/or to MR driver 1008 to adjust drive signal 1009 in response to the sensitivity value. DC output signal 1052 may represent proximity of the target to MR element 1006.

In other embodiments, a time-division multiplexing scheme may be used. For example, coil driver 1004 may drive coil 1002 at a first frequency during a first time period, at a second frequency during a second time period, etc. In some instances, the first and second (and subsequent) time periods do not overlap. In other instances, the first and second time periods may overlap. In these instances, coil driver 1004 may drive coil 1002 at two or more frequencies simultaneously. When the first and second time periods do not overlap, demodulator 1050 may operate at the same frequency as the coil driver 1004. When the time periods overlap, multiple modulators can be used, the first running at the first frequency, and the second running at the second frequency in order to separate out the signals at each frequency.

While it can be advantageous to reduce the directly coupled magnetic field that the MR element 1006 detects in order to achieve an accurate read of the reflected field (and thus the detected target), it may also be advantageous to have some amount of direct coupling (i.e., to directly detect the magnetic field produced by coil 1002) to permit a sensitivity value to be computed. The simultaneous measure of both the field reflected and the field created by the coil allows to determine accurately the distance of the object independent of the sensitivity of the MR elements, coil drive current, etc. . . . The sensitivity of MR elements may vary with temperature and/or with the presence of unwanted DC or AC stray fields in the plane of the MR array. The ratio between the reflected field and the coil field is just dependent on geometrical design and is hence a good parameter to accurately determine a distance.

Referring to FIG. 11, a frequency hopping scheme may be used. For example, coil driver 1004 may drive coil 1002 at different frequencies (e.g. alternate between frequencies over time, or produce a signal containing multiple frequencies). In such embodiments, sensor 1100 may include multiple demodulator circuits and/or filters to detect a signal at each frequency.

Referring to FIG. 11A, a magnetic field sensor 1100' includes coil 1002, coil driver 1004, AC driver 1010, MR driver 1008, MR element 1006, amplifier 1014, low pass filter 1018, temperature sensor 1020, material type module 1022 and offset module 1024.

As shown, AC driver 1010 is coupled to coil driver 1004 to drive coil 1002 at a frequency f1. MR driver 1008 is coupled to AC driver 1102 to drive MR element 1006 at a frequency f2. Frequencies f1 and f2 may be different frequencies and may be non-harmonic frequencies (in other words, f1 may not be a harmonic frequency of f2 and vice versa). In embodiments, frequency f1 is lower than frequency f2. In other embodiments, frequency f1 and f2 may be relatively close to each other so that the difference between the two frequencies falls well below f1 and f2. Frequency f2 may be a zero value or non-zero-value frequency but alternatively, we may choose f1 larger than f2. Then the demodulation is done at f2−f1.

In an embodiment, frequency f1 may be selected to avoid generating an eddy current greater than a predetermined level in the target and/or selected to provide full reflection in the target. The reflected field may be related to the skin depth in the target according to the following formula:

$$\delta = \frac{1}{\sqrt{\sigma\mu\pi f}}$$

In the formula above, σ is the conductivity of the target material, μ is the magnetic permittivity of the target material, and f is the working frequency. If the thickness of the target material is larger than about 5 times the skin depth δ, the field may be totally reflected. In the case where the thickness of the target is equal to the skin depth, only about the half of the field may be reflected. Hence a frequency f chosen to be low enough so the skin depth becomes larger than the thickness of the target may induce low eddy currents and a reflected field with reduced strength. The formula given above may be valid for high conductive and low magnetic materials. For material with low conductivity or for ferromagnetic material, losses of the eddy currents, which may be translated at a complex skin depth, may result in reduction of reflected field strength.

Circuit 1100' may also include a band pass filter 1104 and a demodulator circuit 1106. Band pass filter 1104 may have a pass band that excludes frequencies f1 and f2 but conserves frequency |f1−f2|. In this way, inductive noise from the coil and/or GMR driver into the magnetic sensors may be filtered out. Circuit 1100' may also include a demodulator circuit 1106 that demodulates at frequency |f1−f2| and a low pass filter to recover a signal centered around DC, which may represent the magnetic field seen by the magnetic sensors at f1. In embodiments, the signal at frequency |f1−f2| may include information about the target and/or the directly coupled magnetic field, but may have reduced noise from inductive coupling or other noise sources.

Referring now to FIG. 11B, a magnetic field sensor 1100" includes coil 1002, coil driver 1004, AC driver 1010, MR driver 1008, MR element 1006, amplifier 1014, low pass filter 1018, temperature sensor 1020, material type module 1022, offset module 1024, and segmented linearization module 1026.

As shown, AC driver 1010 is coupled to coil driver 1004, but is not coupled to MR driver 1008 in sensor 1100. In this embodiment, MR driver 1008 may produce a DC signal (e.g. a signal with a frequency of about zero) to drive MR element 1006.

Coil 1002 may produce an AC magnetic field that induces eddy currents and a reflected magnetic field in a target.

Sensor 1100" may also include a demodulation circuit 1060 that can demodulate signal 1016. Demodulation circuit 1060 may multiply signal 1016 by a signal at frequency f, which may shift information about the target in signal 1016 to DC, and may shift noise or other information in the signal to higher frequencies. Low pass filter 1018 may the remove the noise at higher frequencies from the signal. In embodiments, demodulation circuit 1060 may be a digital circuit that demodulates signal 1016 in the digital domain or an analog signal the demodulates signal 1016 in the analog domain.

Sensor 1100" may also include a phase detection and compensation circuit 1062 that detects the phase and/or frequency of the current in coil 1002 and the magnetic field it produces. Circuit 1062 may detect and compensate for discrepancies in phase in coil 1002 and f and produce a corrected signal 1063 that can be used to modulate signal 1016.

In embodiments, the frequency f, the type of material of the target, the shape of the target, wiring and electronics, and/or other factors may cause a phase shift between the drive signal 1010 to coil 1002 and the reflected magnetic field detected by MR element 1008. The phase between the signals can be measured and used to adjust the phase of signal 1063 from phase detection and compensation circuit 1062 to match the phase of signal 1016.

A frequency hopping scheme may also be used. For example, coil driver 1004 and/or MR driver 1008 may drive signals at multiple frequencies. At each frequency, phase detection and compensation module 1062 may adjust the phase of signal 1063 to match the phase of signal 1016.

Referring now to FIG. 11C, a magnetic field sensor 1100''' includes coil 1002, coil driver 1004, AC driver 1010, MR driver 1008, MR element 1006, amplifier 1014, temperature sensor 1020, material type module 1022, offset module 1024, and segmented linearization module 1026.

As shown, AC driver 1010 is coupled to coil driver 1004, but is not coupled to MR driver 1008 in sensor 1100. In this embodiment, MR driver 1008 may produce a DC signal (e.g. a signal with a frequency of about zero) to drive MR element 1006.

Coil 1002 may produce an AC magnetic field that induces eddy currents and a reflected magnetic field in a target. The reflected magnetic field can be detected by MR element 1006, which produces signal 1012 representing the detected magnetic field.

Sensor 1100''' may also include a fast Fourier transform (FFT) circuit 1070 that can perform an FFT on signal 1016. Performing the FFT may identify one or more frequency components in signal 1016. In an embodiment, FFT circuit 1070 may identify the frequency component with the greatest amplitude in signal 1016, which may represent the detected magnetic field at frequency f. FFT circuit 1070 may produce an output signal 1072 including the detected signal at frequency f, as well as any other frequency components of signal 1016.

Alternatively, the driver can generate simultaneously different frequencies fa, fb, fc, and the FFT module may calculate the amplitudes at fa, fb, fc, which may be used to determine different parameters of the target including position, material, thickness, etc. In addition, if a disturbance (e.g. from a deformation of the target, a stray magnetic field, a noise source, etc.) occurs at a particular frequency, the system can detect the disturbance and ignore data at that frequency. The amplitudes calculated by the FFT module may also be used to determine if there is a disturbance at any particular frequency, which can be ignored by subsequent processing. In embodiments, the FFT temperature gain compensation and linearization may be calculated in the analog and/or digital domain.

Referring now to FIG. 11D, a magnetic field sensor 1100D includes coil 1002, coil driver 1004, MR driver 1008, and MR element 1006. The output signal 1007 of MR sensor 1006 may represent a detected magnetic field. Although not shown, sensor 1100D may also include amplifier 1014, low pass filter 1018, temperature sensor 1020, material type module 1022, offset module 1024, and segmented linearization module 1026. An oscillator 1182 may be used to operate coil driver 1004 at a frequency f.

As shown, oscillator 1182 is coupled to coil driver 1004, but is not coupled to MR driver 1008 in sensor 1100D. In this embodiment, MR driver 1008 may produce a DC signal (e.g. a signal with a frequency of about zero) to drive MR element 1006.

Sensor 1100D also includes a quadrature demodulation circuit 1180. Quadrature demodulation circuit 1180 includes shift circuit 1188 to produce a 90° shift of the driving frequency f. Oscillator 1182 may produce a cosine signal at frequency f. Thus, the output of 1188 may be a sine signal at frequency f. Hence by a multiplication in the demodulators 1190 and 1192 (and subsequent low pass filtering), the detected signal of the MR sensor 1006 may be separated into in-phase and out-of-phase components (e.g. signals 1184a and 1186a). The resulting phase and magnitude can be used to determine information about the reflected field and the target. For example, phase information may be used to determine if there is a defect or abnormality in the target, to determine magnetic properties of the material of the target, whether the target is aligned properly, etc. Oscillator 1182 may also produce a square wave with period 1/f, and shift circuit 1188 may shift the square wave in time by 1/(4f).

Referring to FIG. 11E, in another embodiment, magnetic field sensor 1100E may produce a quadrature modulated signal via two signal paths as an alternative to providing both the in-phase and out-of-phase information. In circuit 1100E, half of the MR elements may be driven by a signal at frequency f and half of the MR elements may be driven with a frequency 90° out of phase. The demodulation chain (e.g. the circuits that comprise a demodulation function of the system) may be the same as or similar to the demodulation circuits in FIG. 10 including a low pass filter at DC and compensation and linearization.

In embodiments, quadrature modulation may be used to determine the absolute magnitude and phase of the returned signal. This may allow for automatic correction of unwanted dephasing of the signal, which may provide a more accurate determination of target properties and retrieval of information related to magnetic or loss properties of the material.

Referring to FIG. 11F, a magnetic field sensor 1100F includes coil driver 1004 that drives coil 1002 at a frequency of $f_1$. MR driver 1008 may drive MR element at the same frequency $f_1$, but 90 degrees out of phase with respect to coil drive 1004. As a result, the signal 1016 produced by MR element 1006 may have a frequency that is two times $f_1$ (i.e. $2*f_1$), which may be a result of multiplying a sine and a cosine. Sensor 1100F may include a demodulator circuit 1195 that may demodulate the signal to convert the reflected field information to a frequency around DC.

Figure 12:
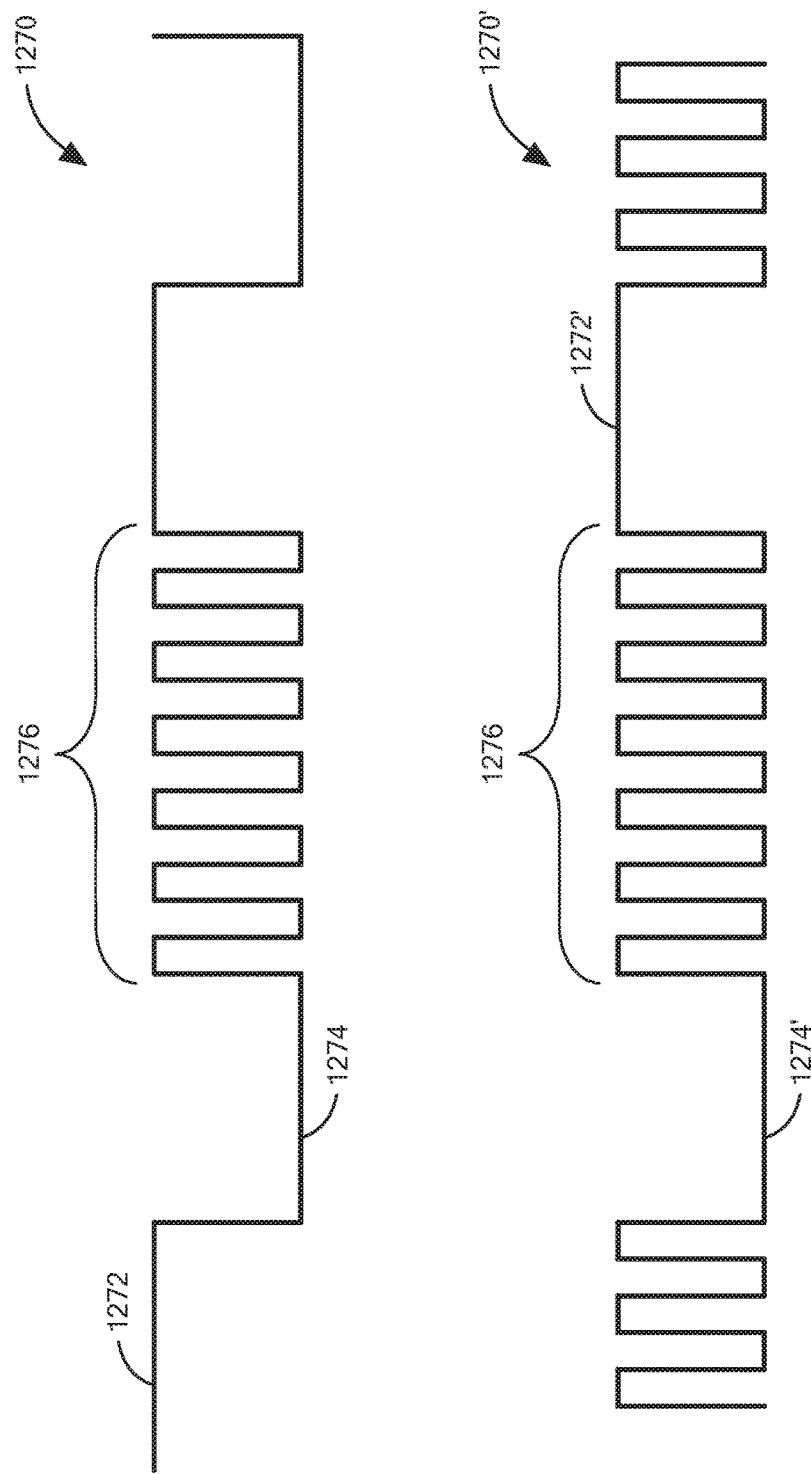
FIG. 12 is a diagram representing an output signal for a system with sensitivity detection.

Referring to FIG. 12, signal 1270 may represent a signal used by coil driver 1004 to drive coil 1002. When the signal is high, coil driver 1004 may drive coil 1002 with current flowing in one direction, and when the signal is low, coil driver may drive coil 1002 with current flowing in the opposite direction. In embodiments, coil driver 1004 may drive coil 1002 with direct current (i.e. at DC) or at a frequency sufficiently low so that the magnetic field produced by coil 1002 does not create eddy currents in the target.

As an example, referring to the skin depth formula above, the skin depth of copper at r 50 Hz may be about 10 mm and at 10 kHz it may be about 600 μm. Hence, given a 0.5 mm thick copper target, a frequency below 5 kHz may create reflected magnetic fields with relatively low strength.

Coil driver 1004 may drive coil 1002 at a relatively low or DC frequency, as shown by signal portions 1272 and 1274. The frequency may be sufficiently low, and thus the duration of portions 1272 and 1274 may be sufficiently long, so that any eddy currents generated in the target by switching of signal 1270 (for example, switching from a high value during portion 1272 to a low value during portion 1274) have time to settle and dissipate. The directly-coupled signal shown during portions 1272 and 1274 may switch from high to low (representing a change in the detected magnetic field) in order to remove any offset due to the directly-coupled magnetic field of coil 1002.

Portion 1276 of signal 1270 may represent the magnetic field detected by MR element 1006 while coil driver 1004 drives coil 1002 at a frequency sufficiently high to induce eddy currents in the target. While portion 1276 is active, MR element 1006 may detect the directly-coupled magnetic field produced directly by coil 1002, and also the magnetic field produced by eddy currents in the target. The detected signal may be subsequently processed to separate the directly-coupled field from the field produced by the eddy currents. Although not shown, portion 1276 may have a larger or smaller magnitude than portion 1272 because the portions may contain different information. For example, portion 1276 may include the reflected signal as well as the directly-coupled signal.

As shown in signal 1270, low frequency portions 1272 and 1274 of different polarities may be adjacent to each other within signal 1270. In other embodiments, as shown in signal 1270', low frequency portions 1272' and 1274' of different polarities may not be adjacent to each other within the signal. For example, they may be separated by high frequency signal portion 1276.

In other embodiments, the coil may be driven at both the low frequency (of low frequency portions 1272 and 1274) and at the high frequency (of high frequency portion 1276) simultaneously. The frequencies may then be separated using signal processing techniques to measure a MR element's response.

In certain instances, the ration of the low frequency portions 1272 and 1274 to the high frequency portion 1276 can be used to determine or indicate the magnitude of the reflected signal. Measuring the ratio in this way may reduce sensitivity of the magnitude measurement to external, unwanted variations such as variations due to temperate, stray magnetic fields, etc.

Figure 12A:
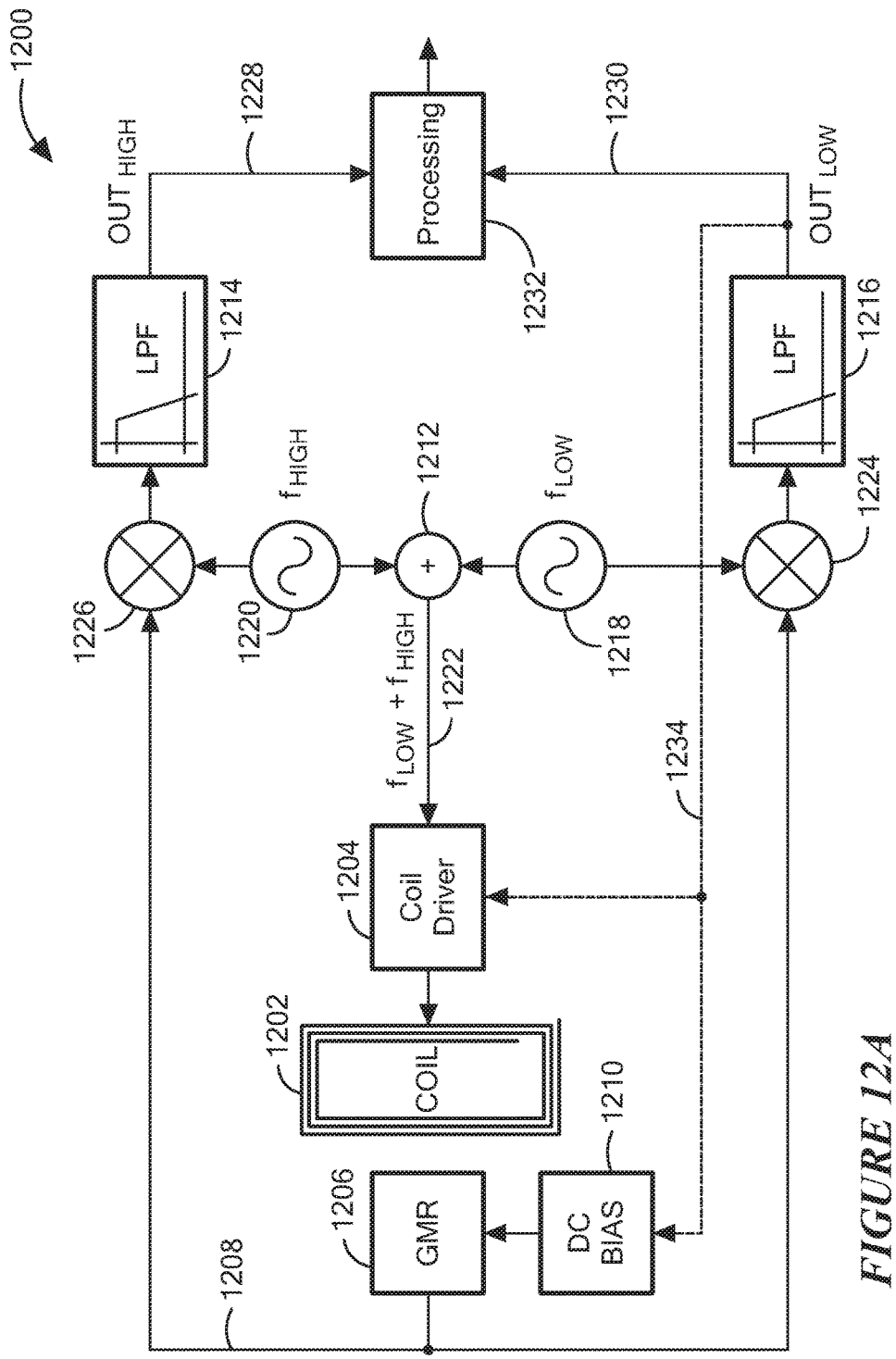
FIG. 12A is a block diagram of a magnetic field detection circuit with sensitivity detection.

Referring now to FIG. 12A, magnetic field sensor 1200 may be configured to adjust the output signal of the magnetic field sensor in response to the sensitivity value. Sensor 1200 may include a coil 1202 and coil driver 1204. MR element 1206 may detect a magnetic field produced by coil 1202, and as reflected by a target, as described above. In embodiments, the output signal 1208 of MR element 1206 may comprise a first frequency and a second frequency. For example, the first frequency may be the frequency of the coil driver, and the second frequency may be 0 Hz, or DC. In this case, MR element 1206 may be driven by a DC bias circuit 1210. In other examples, the second frequency may be a non-zero frequency.

In another embodiment, coil driver 1204 may drive coil 1202 at one frequency during a first time period, and by another frequency during a second time period. The time periods may alternate and not overlap.

Sensor 1200 may also include a separator circuit, which may include one or more low pass filters 1214 and 1216, as well as demodulators 1224 and 1226. Sensor 1200 may also include mixer circuit 1212. Oscillators 1218 and 1220 may provide oscillating signals used to drive coil 1202 and process signal 1208. In embodiments, oscillator 1220 may provide a signal with a higher frequency ($f_{high}$) than that of oscillator 1218 ($f_{low}$). In embodiments, $f_{low}$ is a sufficiently low frequency so that any reflected field produced by the target as a result of frequency flow is zero, sufficiently small that it is not detected, or sufficiently small so that its effect on the output is negligible or within system tolerances.

Mixer 1212 may mix (e.g. add) the signals from oscillator 1218 and 1220 to produce signal 1222, which it feeds to coil driver 1204. Coil driver 1204 may then drive coil 1202 according to the mixed signal 1202.

Because coil 1202 is driven by the mixed signal, output signal 1208 may include oscillations at $f_{high}$ and $f_{low}$ as detected by MR sensor 1206. Demodulator 1226 may demodulate signal 1208 at frequency $f_{high}$ in order to separate the portion of signal 1208 at frequency $f_{high}$ from other frequencies in the signal. One skilled in the art may recognized that the demodulation process may result in the other frequencies being shifted to higher frequencies in the signal. Low pass filter 1214 may then remove these frequencies from the signal and produce a filtered signal 1228 comprising primarily information at frequency $f_{high}$ or at DC.

Similarly, demodulator 1224 may demodulate signal 1208 at frequency $f_{low}$ in order to separate the portion of signal 1208 at frequency $f_{low}$ from other frequencies in the signal. One skilled in the art may recognized that the modulation process may result in the other frequencies being shifted to higher frequencies in the signal. Low pass filter 1216 may then remove these frequencies from the signal and produce a filtered signal 1230 comprising primarily information at frequency $f_{low}$ or at DC. Processing circuit 1232 may process signals 1228 and 1230 to produce output signal 1232 representing the detected target.

Processing circuit 1232 may process signals 1228 and 1230 in various ways including, taking the ratio of the signals to provide an output that is substantially insensitive to undesirable variations caused by stray magnetic field interference, temperature shifts, package stresses, or other external stimuli. Taking the ratio of the signals can also provide an output that is substantially insensitive to variations in the coil driver (e.g. variations in current or voltage provided by the coil driver) due to temperature, changes in supply voltage, external stimuli, etc.

Signal 1230 may also be used as a sensitivity signal fed into DC bias circuit 1220, as shown by arrow 1234. DC Bias circuit 1210 may adjust the voltage level used to drive MR element 1206 based on the value of signal 1230, to compensate for changes in system sensitivity due to temperature, stray magnetic fields, package stress, etc.

Figure 12B:
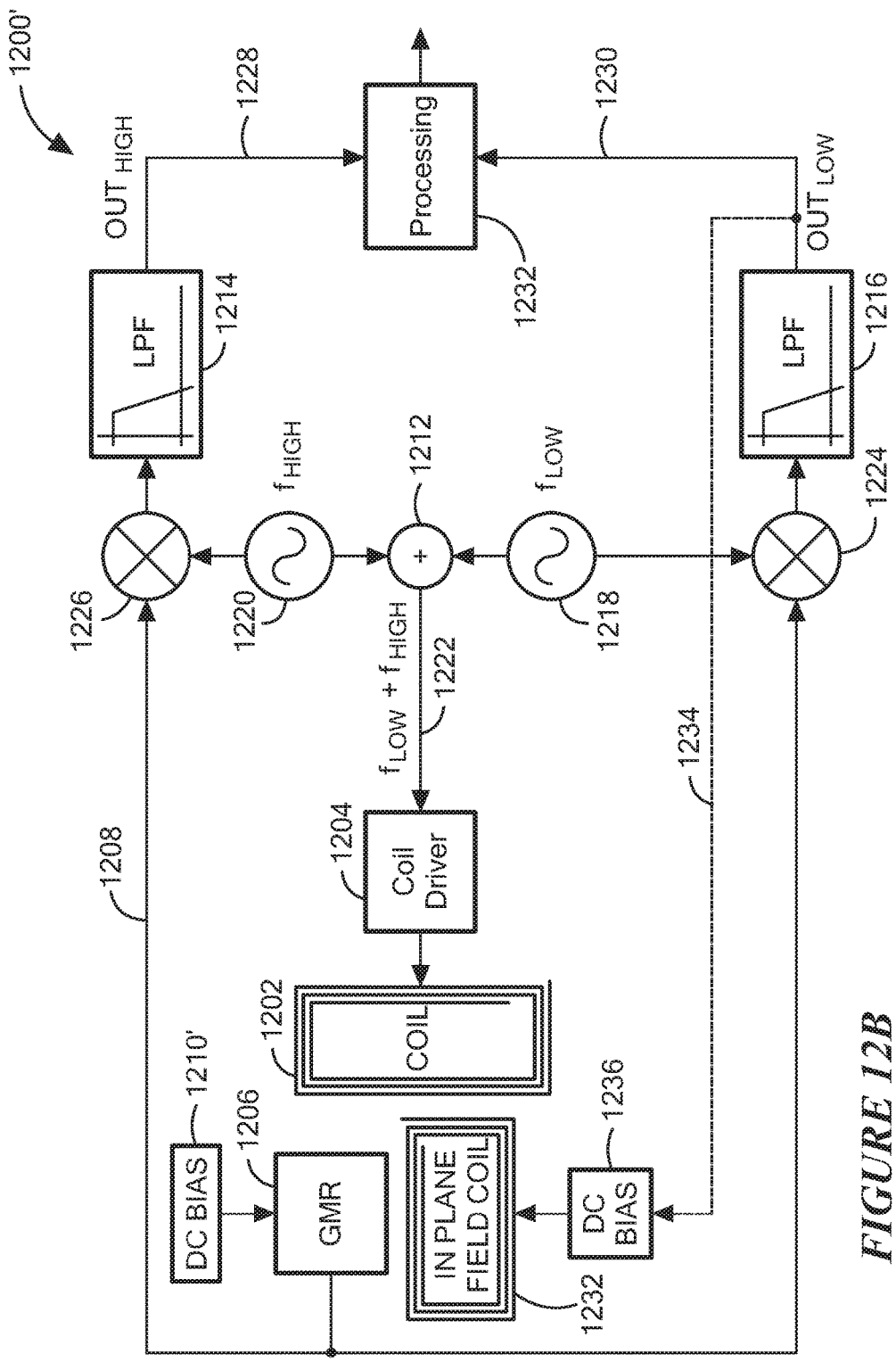
FIG. 12B is a block diagram of an embodiment of a magnetic field detection circuit with sensitivity detection.

Referring to FIG. 12B, magnetic field sensor 1200' may be similar to sensor 1200, and may also include an additional in-plane field coil 1236. DC bias circuit 1236 may drive coil 1232 with a DC current to create a constant magnetic field. The constant magnetic field may be detected directly by MR element 1206 and may be a biasing magnetic field. In other embodiments, the magnetic field produced by in-plane field coil 1232 may be used to generate a signal proportional to the MR sensitivity, which can be detected by MR element 1206 and subsequently fed back and used to adjust the sensitivity of circuit 1200'. In embodiments, the magnetic field produced by in-plane field coil 1232 may be perpendicular to the magnetic field produced by coil 1202 and used to increase/decrease the sensitivity of the MR element. DC bias circuit 1236 may drive coil 1232 in such a way to compensate for changes in sensitivity seen by the closed loop system. In other words, DC bias circuit may change the magnitude of the driving current supplied to coil 1232 in response to feedback signal 1234 to compensate for sensitivity errors up to the bandwidth of the feedback loop system. The bandwidth may be determined (or at least heavily influenced) by the cutoff frequency of filter 1216.

As shown, DC bias circuit 1236 may receive signal 1230 and adjust the amount of current provided to in-plane field coil 1232, which may subsequently adjust thus the strength the magnetic field produced by in-plane field coil 1232. Although not shown in FIG. 12B, DC bias circuit 1210' may also receive signal 1230 and use it to adjust the current that drives MR element 1206. In embodiments, DC bias circuit 1210', DC bias circuit 1236, or both may adjust their outputs based on signal 1230.

Figure 12C:
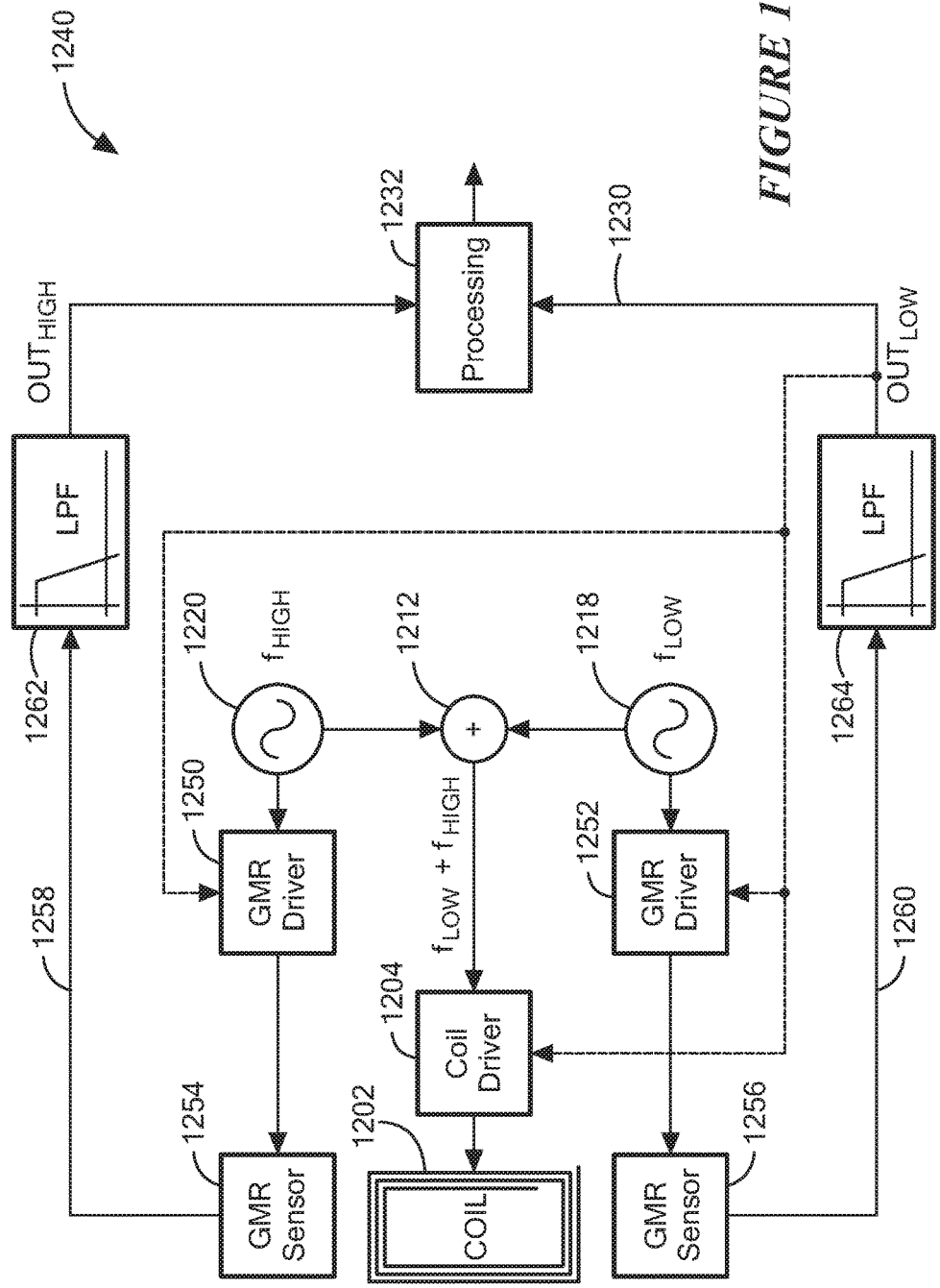
FIG. 12C is a block diagram of an embodiment of a magnetic field detection circuit with sensitivity detection.

Referring to FIG. 12C, a magnetic field sensor 1240 includes oscillator 1220, oscillator 1218, and mixer 1212. Coil driver 1204 receives the signal produced by mixer 1212 and drives coil 1202 with a signal comprising frequencies $f_{high}$ and $f_{low}$.

Sensor 1240 may include two (or more) MR elements 1254 and 1256. MR driver 1250 may be coupled to oscillator 1220 and may drive MR sensor 1254 at frequency $f_{high}$, and MR driver 1252 may be coupled to oscillator 1218 and my driver MR sensor 1256 at frequency $f_{low}$. Low pass filter 1216 may filter output signal 1258 from MR sensor 1254 and low pass filter 1264 may filter output signal 1260 from MR sensor 1256. Due to the frequencies at which MR sensors 1254 and 1256 are driven, output signal 1258 may include a frequency component at $f_{high}$ and output signal 1260 may include a frequency component at $f_{low}$. Filtered signal 1230 may be a sensitivity signal that can be used to adjust the sensitivity of sensor 1240. Thus, signal 1230 may be fed back to MR driver 1252, MR driver 1250, and/or coil driver 1204, which may each adjust their output based on the value of signal 1230. In embodiments, signal 1230 may be a DC or oscillating signal.

Figure 13:
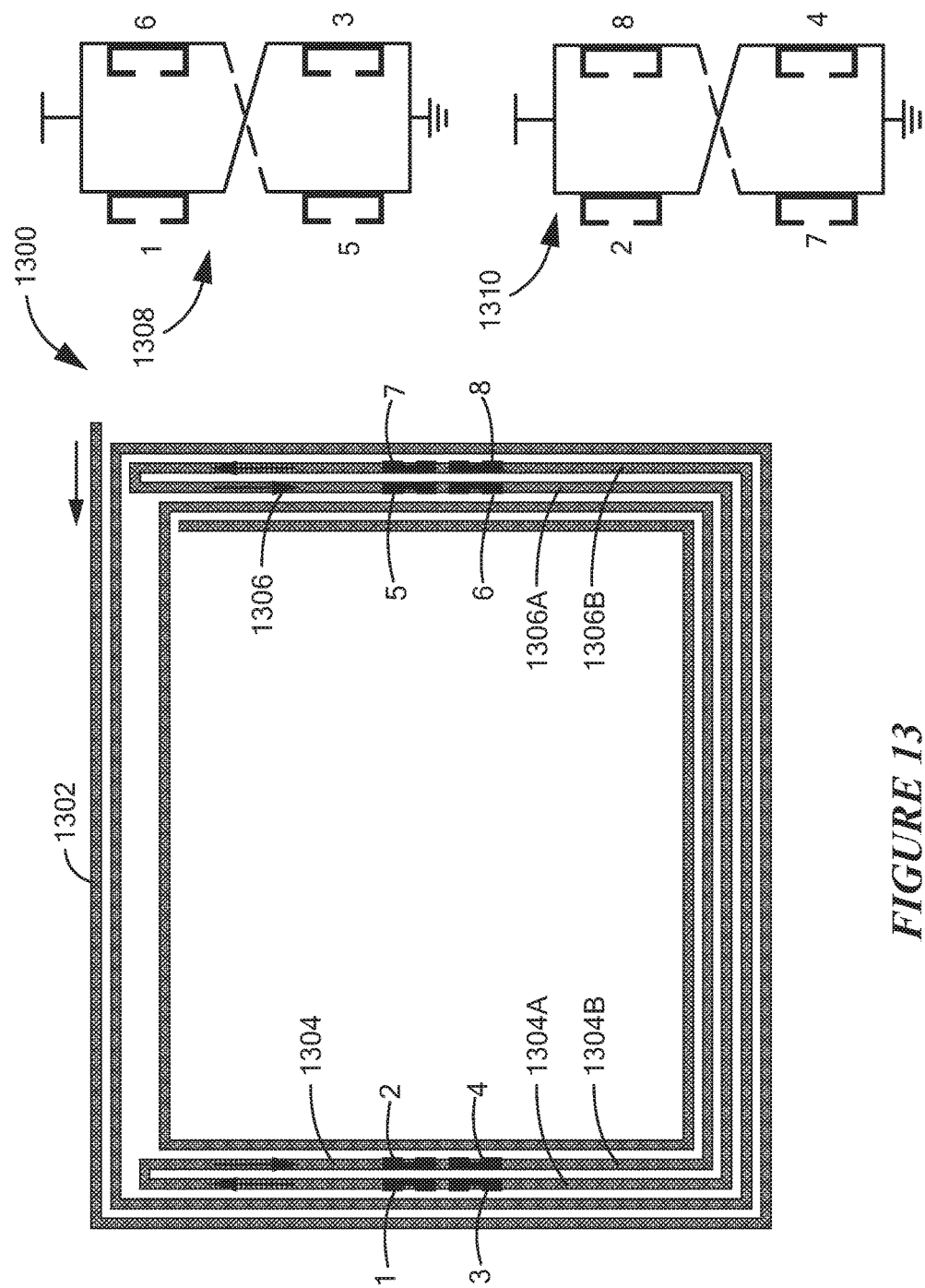
FIG. 13 is a schematic diagram of an embodiment of a magnetic field detection circuit with sensitivity detection including a coil and MR elements.

Referring to FIG. 13, a circuit 1300 includes a coil 1302 and MR elements 1-8 arranged in bridge configurations. Coil 1302 may include so called countercoil portions 1304A, B and 1306A, B. First countercoil portion 1304A may produce a field to the left for MR elements below it. Subsequently, portion 1304B may produce a field to the right, portion 1306A may produce a field to the right, and portion 1306B may produce a field to the left. MR elements 1 and 3 are positioned near countercoil portion 1304A and MR elements 2 and 4 are positioned near countercoil portion 1304B. MR elements 5, 6 are positioned near countercoil portion 1306A, and MR elements 7, 8 are positioned near countercoil portion 1306B. Also, the MR bridges are split so that some of the elements in each bridge are located near countercoil portion 1304 and some of the elements are located near countercoil portion 1306. For example, MR bridge 1308 comprises MR elements 1 and 3 (positioned near countercoil portion 1304) and MR elements 5 and 6 (positioned near countercoil portion 1306). Providing countercoil portions 1304 and 1306 may influence the magnitude and polarity of the directly coupled field on the MR elements.

MR elements 1, 3 may have a first coupling factor with relation to coil 1302, MR elements 2, 4 may have a second coupling factor, MR elements 5 and 6 may have a third coupling factor, and MR elements 7, 8 may have a fourth coupling factor with relation to coil 1302. In an embodiment, the coupling factor of MR elements 1, 3, 7, and 8 may be equal and opposite to the coupling factor of MR elements 2, 4, 5, and 6. This may be due, for example, to coil portions 1304A, B and 1306A, B carrying equal current in opposite coil directions, as well as the positioning of the MR elements in relation to them.

In an embodiment, bridges 1308 and 1310 will respond to a reflected field equally. However, they may respond oppositely to the directly coupled field. The addition of the outputs of the two bridges may contain information about the reflected field and the subtraction of the two bridges may contain information about the directly coupled field. The directly coupled field information can then be used as a measure of system sensitivity and be used to normalize the reflected field information. In another embodiment, bridges 1308 and 1310 respond to a reflected field equally. However, they may respond differently (not necessarily exactly oppositely) to the directly coupled field. The subtraction of the two bridges still results in a signal only containing information about the directly coupled field, which can be used as a measure of system sensitivity. The addition of the two bridges may include some directly coupled field information along with information about the reflected field. However, this can be compensated for with the linearization block, as it shows up as a constant offset.

For example, during operation, the following formulas may apply:

$$V_{bridge1} = (C_r + C_1) * i * S_1$$

$$V_{bridge2} = (C_r + C_2) * i * S_2$$

In the formulas above, $C_r$ represents the reflected field, $C_1$ represents the directly coupled field detected by the first MR bridge, $C_2$ represents the directly coupled field detected by the second MR bridge, i is the current through the coil, $S_1$ represents the sensitivity of the first MR bridge, and $S_2$ represents the sensitivity of the second MR bridge. Assuming that S1=S2 and solving for Cr:

$$C_r = \frac{(V_{bridge2})(C_1) - (V_{bridge1})(C_2)}{V_{bridge1} - V_{bridge2}}$$

The equation above provides a formula for $C_r$ independent of current and sensitivity of the MR elements. In embodiments, the geometry of the coil, MR elements, and target my provide that $C_1 = -C_2$. In other embodiments, the geometry of the system may provide other ratios of $C_1$ and $C_2$. With a known ratio, $C_r$ can be computed to provide a value for the reflected field.

Figure 13A:
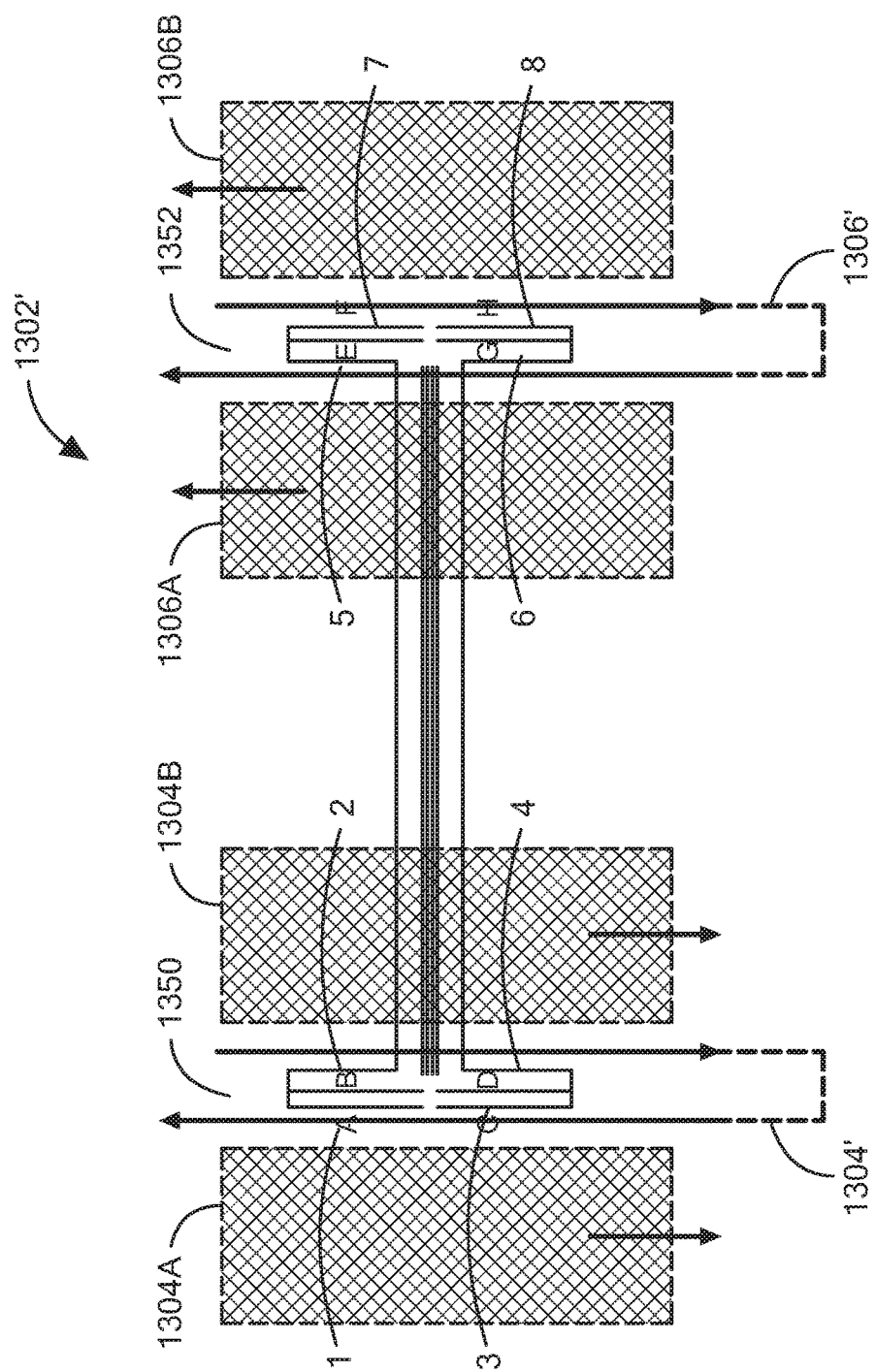
FIG. 13A is a schematic diagram of an embodiment of a coil having countercoils and gaps between traces.

Referring to FIG. 13A, a coil 1302' may include countercoil portions 1304'A, B and 1306'A, B and gap between coil elements. In FIG. 13A, only the middle portion of coil 1302' and MR elements 1-8 are shown.

The countercoil portions 1304' and 1306' may each be placed in a respective gap 1350 and 1352 between traces of the main coil. MR elements 1-8 may be placed within the gaps of the main coil. As with the gap in FIG. 6, placing the MR elements within gaps 1350 and 1350 may reduce sensitivity of the MR elements to the directly coupled magnetic field. Thus, a coil design for coil 1302' may adjust sensitivity of the MR elements to the directly coupled field by including gaps 1350 and 1352 to reduce the sensitivity and countercoil portions 1304' and 1306' to increase the sensitivity in order to achieve the desired direct coupling on each element. In an embodiment, the direct coupling field is similar in magnitude to the reflected field.

Figure 13B:
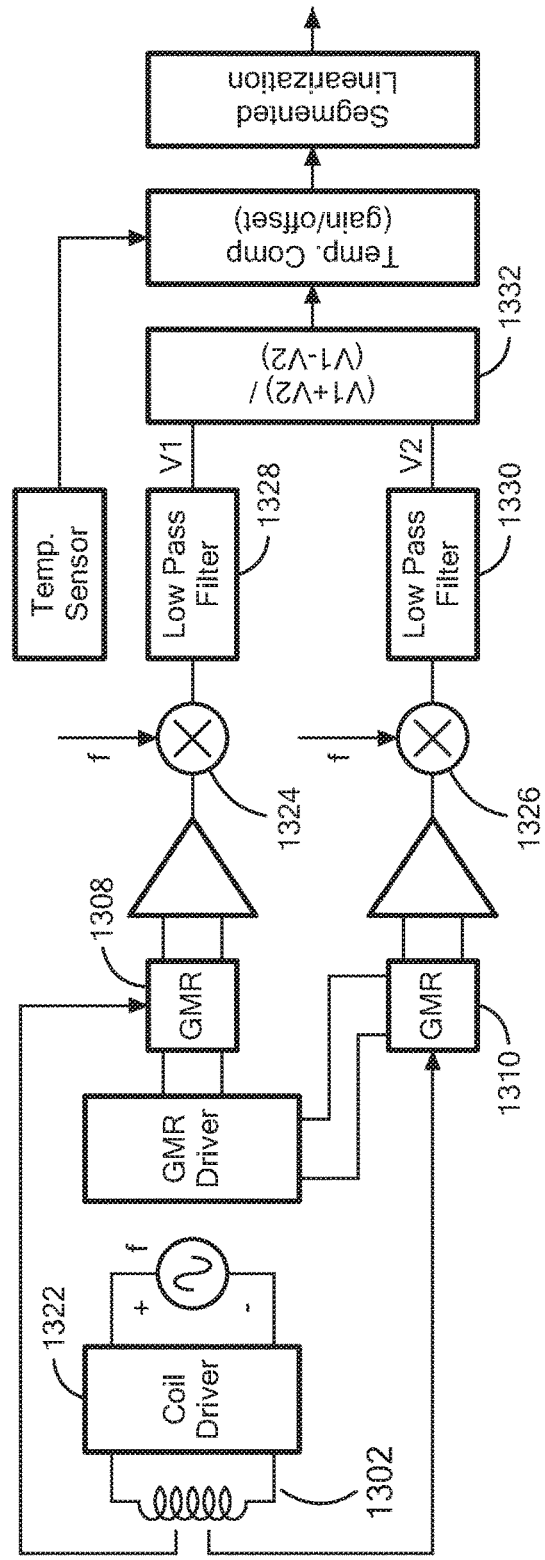
FIG. 13B is a block diagram of an embodiment of a magnetic field detection circuit with sensitivity detection.

Referring to FIG. 13B, magnetic field sensor 1320 may include coil 1302, MR bridge 1308, and MR bridge 1310 as arranged in FIG. 13. Coil driver 1322 may drive coil 1302 at frequency f. MR driver 1324 may drive one or both MR bridges 1308 and 1310 at 0 Hz (i.e. DC) or at another frequency.

Demodulator 1324 and demodulator 1326 may demodulate the output signals from MR bridges 1308 and 1310, respectively, at frequency f. This may shift the frequency components of the signals at frequency f to 0 Hz or DC, and may shift other frequency components in the signal to higher frequency bands. Low pass filters 1328 and 1330 may the remove the higher frequency components from the signals and provide a DC signal V1 (corresponding to the magnetic field detected by MR bridge 1308 and a DC signal V2 (corresponding to the magnetic field detected by MR bridge 1310) to processing block 1332. Processing block 1332 may process signals V1 and V2 to produce a signal representing the detected target. In an embodiment, processing block may perform the operation X=(V1+V2)/(V1−V2), where X is the signal representing the detected target. In this embodiment, the position of the MR of the bridges 1308 and 1310 are chosen in a way that the first bridge sees a negative signal from the coil (directly coupled field) and the second an opposite signal from the coil. Both bridges may see the same reflected signal. Hence V1+V2 may substantially comprise the reflective signal and V1−V2 the coil signal. The ratio gives then a quantity X which is independent on the sensitivity change of the MR elements due to the temperature or stray fields for example, as well as variations in coil current. In this embodiment, the position of the MRs (and/or coils) may be chosen so that each MR is seeing (e.g. can detect) a coil signal and a reflected signal of the same range of amplitude i.e. typically a reflected field varying from 0.1% to 100% of the direct detected field.

Referring now to FIG. 14, system 1400 includes a magnetic field sensor 1402 and target 1404. Magnetic field sensor 1402 may be the same as or similar to magnetic field sensor 100 and/or any of the magnetic field sensors described above. Accordingly, magnetic field sensor 1402 may include a coil to produce a magnetic field and produce eddy currents within conductive target 1404, and one or more magnetic field sensing elements to detect a reflected field from the eddy currents.

The skin effect of target 1404 may be used to detect linear, speed, and angle (in the case of a rotating target) measurements by controlling the amount of reflected magnetic signal, and using the amount of reflected signal to encode the target position. A target can be created by combining a high conductivity material (shallow skin depth, measured with high frequency signal) and relatively low-conductivity materials (deep skin depth, measured using a medium or low frequency signal). The target can be created by milling or etching a linear slope or digital tooth pattern into the low conductivity material. In a subsequent step a high conductivity material can be deposited over the surface then milled or polished to create a planar surface. Alternatively, the low conductivity material can be omitted.

Measurement techniques can also utilize various frequencies (of coil 1002 for example) and the skin effect of the target. A relatively high frequency and shallow skin depth can be used to measure the air gap distance between the sensor and the face of the target. This signal can then be used to calibrate the sensitivity of the system. A medium frequency with a skin depth that exceeds the maximum thickness of the high conductivity material may be used to sense the position of the portion of the target formed by the low conductivity material. A relatively low frequency signal (e.g. low enough that it is not reflected by the target) may be used to measure the overall sensitivity of the MR sensors and provide feedback to compensate for any changes in sensitivity due to stray field, temperature, or package stresses.

Referring again to FIG. 14, target 1404 may comprise a first material portion 1406 and a second material portion 1408. First material portion 1406 may be a high-conductivity material, such as a metal; and second material portion 1408 may be a relatively low-conductivity material, such as a plastic, ceramic, or other insulating material; or vice versa. In embodiments, the first and second material portions 1406 and 1408 may be a unitary structure as may be integrally formed or may be separate elements physically coupled to each other, as shown in FIG. 14.

The thickness 1410 of first material portion 1406 may vary along the length of target 1404 so that, at one end 1412, first material portion 1406 is relatively thick and, at another end 1414, first material portion 1406 is relatively thin. The eddy currents induced by magnetic field sensor 1402 at the thick end 1412 of first material portion 1406 may differ from those induced at the thin end 1414. Accordingly, the reflected magnetic field produced at thick end 1406 may also differ from the reflected magnetic field produced at thin end 1414. Because the thickness of first material portion 1406 varies linearly along the length of target 1404, the reflected magnetic field may also vary linearly along the length of target 1404. Thus, the magnetic field sensing elements of magnetic field sensor 1402 may detect the difference in the reflected magnetic field to determine where magnetic field sensor 1402 is positioned along the length of target 1404. In embodiments, if a relatively high frequency is used to sense the airgap, the thickness at end 1414 may be chosen to be greater than one skin depth and less than five skin depths at the chosen frequency. The thickness at end 1412 may be chosen to be than one skin depth at a relatively lower frequency.

In embodiments, target 1404 may move in a linear direction (shown by arrow 1416) with respect to magnetic field sensor 1402. As target 1404 moves, magnetic field sensor 1402 may detect changes in the reflected field to determine the position of target 1404 with respect to magnetic field sensor 1402. Of course, in other embodiments, target 1416 may be stationary and magnetic field sensor 1402 may move with respect to target 1404.

As another example, multiple frequencies may be used to determine air gap and solve for position of the target 1404. For example, if the thickness of first material portion 1406 at end 1414 is greater than one skin depth at a frequency f1, then the response at frequency f1 may vary only as a function of air gap between target 1404 and the MR elements. Using a second frequency, if the thickness of first material portion 1406 at end 1414 is less than one skin depth at a frequency f2, the response may vary as a function of both air gap and position of target 1404.

Referring now to FIG. 14A, system 1400' may include magnetic field sensor 1402 and a rotating target 1418, which may be in the shape of a cylinder, a gear, etc. Target 1418 may include a first material portion 1420 and a second material portion 1422. First material portion 1420 may be a high-conductivity material, such as a metal; and second material portion 1422 may be a relatively low-conductivity material, such as a plastic, ceramic, or other insulating material; or vice versa. In embodiments, the first and second material portions 1420 and 1422 may be a unitary structure as may be integrally formed or may be separate elements physically coupled to each other, as shown in FIG. 14.

The thickness 1423 of first material portion 1420 may vary around the circumference of target 1418 as a function of angle around target 1418 so that, at point 1424, first material portion 1420 is relatively thin and, at point 1426, first material portion 1420 is relatively thick. The eddy currents induced by magnetic field sensor 1402 in thicker portions of first material 1420 may differ from those induced at thinner portions. Accordingly, the reflected magnetic field produced at point 1424 may also differ from the reflected magnetic field produced at point 1426. Because the thickness of first material portion 1420 varies around the circumference of target 1418 as a function of an angle around target 1418, the reflected magnetic field may also vary around the circumference.

Magnetic field sensor 1402 may be placed outside the radius of target 1418, and adjacent to the outside surface of target 1418. Thus, the magnetic field sensing elements of magnetic field sensor 1402 may detect the difference in the reflected magnetic field to determine the rotational angle of target 1418. Magnetic field sensor 1402 may also detect rotational speed and/or direction of target 1418.

Referring now to FIG. 14B, system 1400" may include magnetic field sensor 1402 and a rotating target 1428. Target 1428 may include a first material portion 1430 and a second material portion 1432. First material portion 1430 may be a high-conductivity material, such as a metal; and second material portion 1432 may be a relatively low-conductivity material, such as a plastic, ceramic, or other insulating material; or vice versa. In embodiments, the first and second material portions 1430 and 1432 may be a unitary structure as may be integrally formed or may be separate elements physically coupled to each other, as shown in FIG. 14.

In FIG. 14B, the thickness of first material portion 1430 may extend into the page. The thickness of first material portion 1430 may vary around the circumference of target 1428 as a function of an angle around target 1428 so that, at point 1434, first material portion 1430 is relatively thick and, at point 1436, first material portion 1430 is relatively thin. The eddy currents induced by magnetic field sensor 1402 in thicker portions of first material 1430 may differ from those induced at thinner portions. Accordingly, the reflected magnetic field produced at point 1434 may also differ from the reflected magnetic field produced at point 1436. Because the thickness of first material portion 1430 varies around the circumference of target 1428, the reflected magnetic field may also vary around the circumference.

Magnetic field sensor 1402 may be placed inside the radius of target 1428, and adjacent to the substantially flat face 1440 of target 1428. In other words, if target 1428 is placed at the end of a rotating shaft, magnetic field sensor 1402 may be positioned adjacent to the face of one end of the shaft. Thus, the magnetic field sensing elements of magnetic field sensor 1402 may detect the difference in the reflected magnetic field to determine the rotational angle of target 1428. Magnetic field sensor 1402 may also detect rotational speed and/or direction of target 1418.

Magnetic sensor 1402 can be mounted in a gradiometer mode as illustrated, for example, in FIG. 3A. Half of the gradiometer may be situated at in a position where the distance between the conductive part 1450 and the target remains substantially constant and half of the gradiometer may be situated in a position where the slope 1404 of the conductive material is present. The difference between the two signals may be used to suppress unwanted fluctuations due to the vibration of the target.

Figure 15:
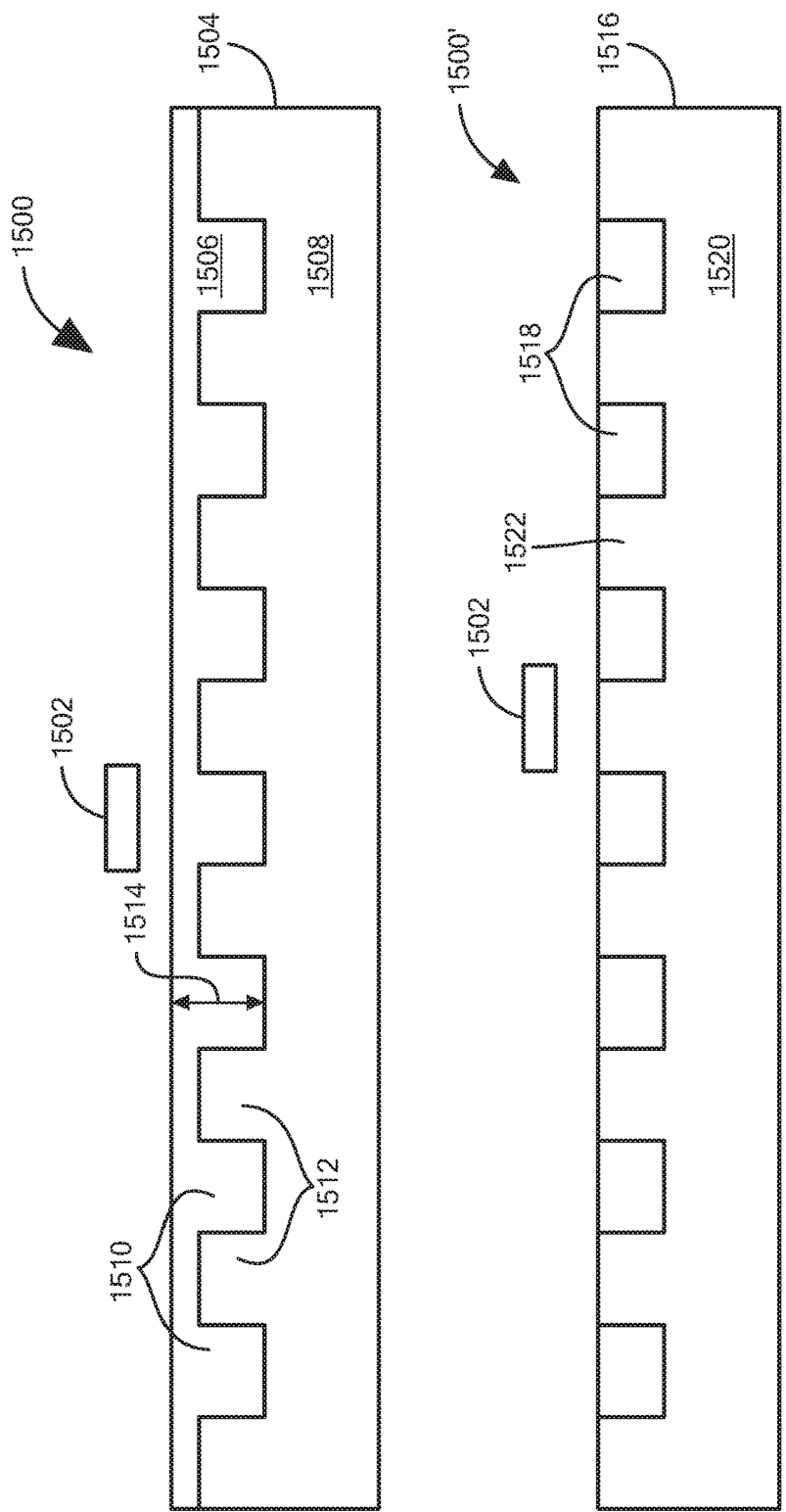
FIG. 15 is a side view of a magnetic field sensor and a magnetic target having material with multiple thicknesses.

Referring to FIG. 15, system 1500 may include magnetic field sensing element 1502 and target 1504. Magnetic field sensor 1502 may be the same as or similar to magnetic field sensor 100 and/or any of the magnetic field sensors described above. Accordingly, magnetic field sensor 1502 may include a coil to produce a magnetic field and produce eddy currents within target 1504, and one or more magnetic field sensing elements to detect a reflected field from the eddy currents.

Target 1504 may comprise a first material portion 1506 and a second material portion 1508. First material portion 1506 may be a high-conductivity material, such as a metal; and second material portion 1508 may be a relatively low-conductivity material, such as a plastic, ceramic, or other insulating material; or vice versa. In embodiments, the first and second material portions 1506 and 1508 may be a unitary structure as may be integrally formed or may be separate elements physically coupled to each other, as shown in FIG. 14.

First material portion 1506 may comprise a series of alternating wells 1510 and valleys 1512. Wells 1510 may have a thickness 1514 relatively greater than the thickness of valleys 1512. Accordingly, the reflected magnetic field produced within wells 1510 may differ from the reflected magnetic field produced at valleys 1512. Thus, the magnetic field sensing elements of magnetic field sensor 1502 may detect the differing magnetic fields produced by wells 1510 and valleys 1512 as target 1504 moves relative to magnetic field sensor 1502. The detected magnetic fields may be used to detect speed, position, rotational angle, and/or direction of magnetic target 1500, for example.

System 1500' may include magnetic field sensor 1502 and target 1516. Target 1516 may comprise one or more first material portions 1518 and a second material portion 1520.

First material portions 1518 may be a high-conductivity material, such as a metal; and second material portion 1522 may be a relatively low-conductivity material, such as a plastic, ceramic, or other insulating material; or vice versa.

First material portions 1518 may comprise a series of discrete wells positioned in a spaced arrangement along the length of target 1516. Accordingly, when magnetic field sensor 1502 is adjacent to a tooth 1518, a reflected magnetic field will be produced and detected. When magnetic field sensing element is adjacent to an insulating area (e.g. area 1522), a reflected magnetic field may not be produced by the insulating area 1522. Thus, the magnetic field sensing elements of magnetic field sensor 1502 may detect the reflected magnetic fields produced by wells 1518 and detect when no reflected magnetic field is produced as target 1516 moves relative to magnetic field sensor 1502. The detected magnetic fields may be used to detect speed and/or direction of magnetic target 1516, for example.

Figure 15B:
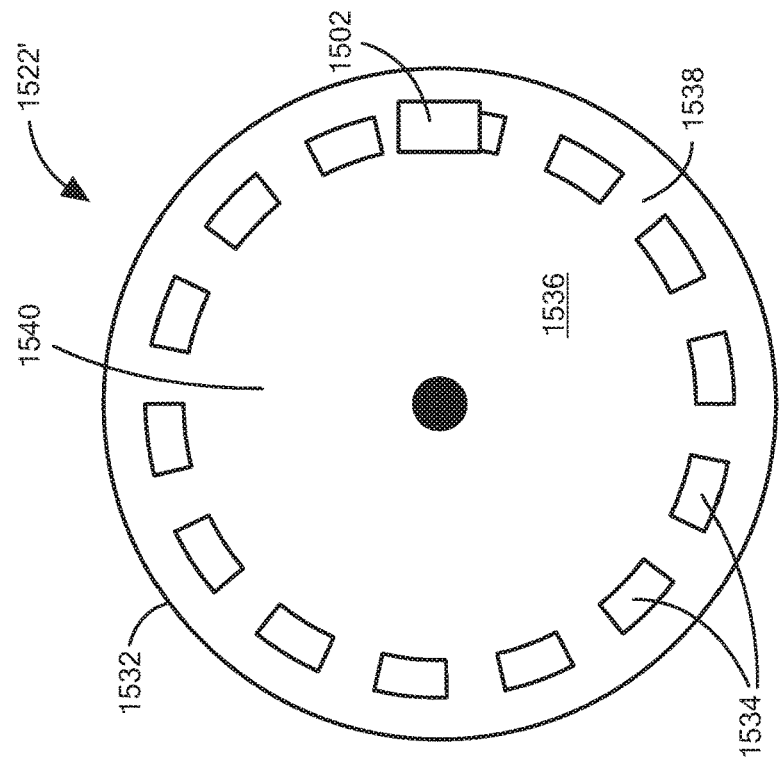
FIG. 15B is a side view of a magnetic field sensor and a magnetic target having material with multiple thicknesses.
Figure 15A:
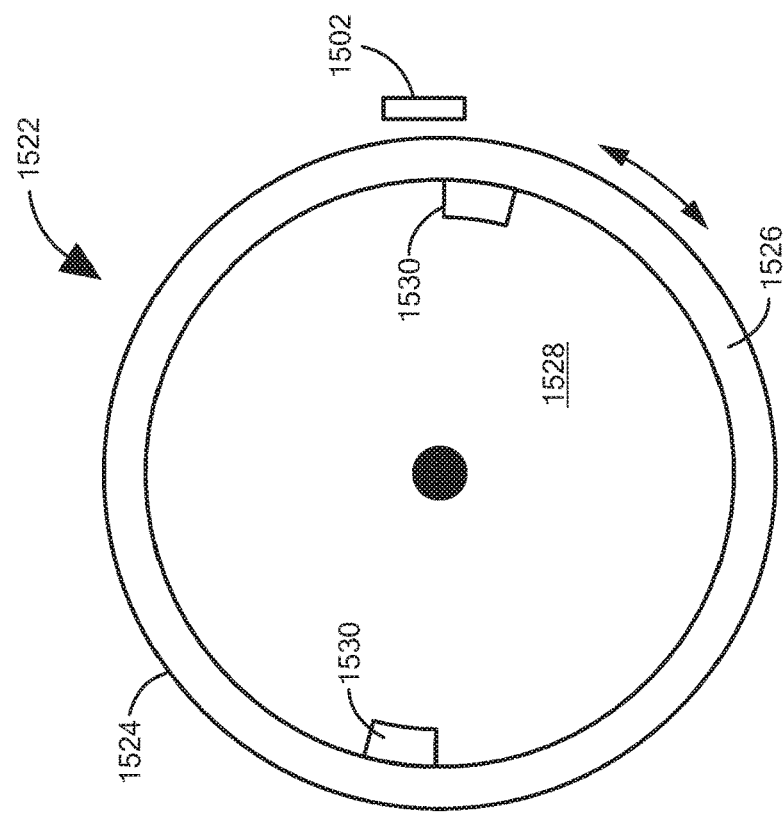
FIG. 15A is a side view of a magnetic field sensor and a magnetic target having material with multiple thicknesses.

Referring to FIG. 15A, system 1522 may include magnetic field sensor 1502 and rotating target 1524. Target 1524 may comprise first material portion 1526 and a second material portion 1528. First material portion 1526 may be a high-conductivity material, such as a metal; and second material portion 1528 may be a relatively low-conductivity material, such as a plastic, ceramic, or other insulating material; or vice versa.

First material portions 1526 may comprise one or more teeth 1530 positioned in a spaced arrangement around the circumference of target 1524 at various angles around target 1524. Although two teeth are shown, target 1524 may include one tooth, two teeth, or more teeth in spaced relation around the circumference of target 1524. The teeth may be spaced evenly or in an uneven pattern.

Accordingly, when magnetic field sensor 1502 is adjacent to a tooth 1530, a reflected magnetic field will be produced and detected. When magnetic field sensing element is not adjacent to tooth, a reflected magnetic field with a different strength may be produced by first material portion 1526. Thus, the magnetic field sensing elements of magnetic field sensor 1502 may detect the reflected magnetic fields produced by teeth 1530, and the reflected magnetic field produced by areas of first material 1526 without teeth, as target 1524 rotates relative to magnetic field sensor 1502. The detected magnetic fields may be used to detect speed and/or direction of magnetic target 1500, for example.

Referring to FIG. 15B, system 1522' may include magnetic field sensor 1502 and rotational 1532. Target 1532 may comprise one or more first material portions 1534 and a second material portion 1536. First material portions 1534 may be a high-conductivity material, such as a metal; and second material portion 1536 may be a relatively low-conductivity material, such as a plastic, ceramic, or other insulating material; or vice versa.

First material portions 1534 may comprise a series of discrete wells positioned in a spaced arrangement around a radial circumference of target 1532. First material portions 1530 may be spaced evenly, or according to any type of pattern. Accordingly, when magnetic field sensor 1502 is adjacent to one of the first material portions 1534, a reflected magnetic field will be produced and detected. When magnetic field sensor 1502 is adjacent to an insulating area (e.g. area 1538), a reflected magnetic field may not be produced by the insulating area 1538. Thus, the magnetic field sensing elements of magnetic field sensor 1502 may detect the reflected magnetic fields produced by first material portions 1534 and detect when no reflected magnetic field is produced by insulating areas 1538 as target 1532 rotates relative to magnetic field sensor 1502. The detected magnetic fields may be used to detect rotational speed and/or direction of magnetic target 1532, for example.

Magnetic field sensor 1502 may be placed inside the outermost radius of target 1532, and adjacent to a substantially flat face 1540 of target 1532. In other words, if target 1532 is placed at the end of a rotating shaft, magnetic field sensor 1502 may be positioned adjacent to the face of one end of the shaft. Thus, as target 1532 rotates, the magnetic field sensing elements of magnetic field sensor 1502 may detect first material portions 1534 as they pass by.

Figure 15C:
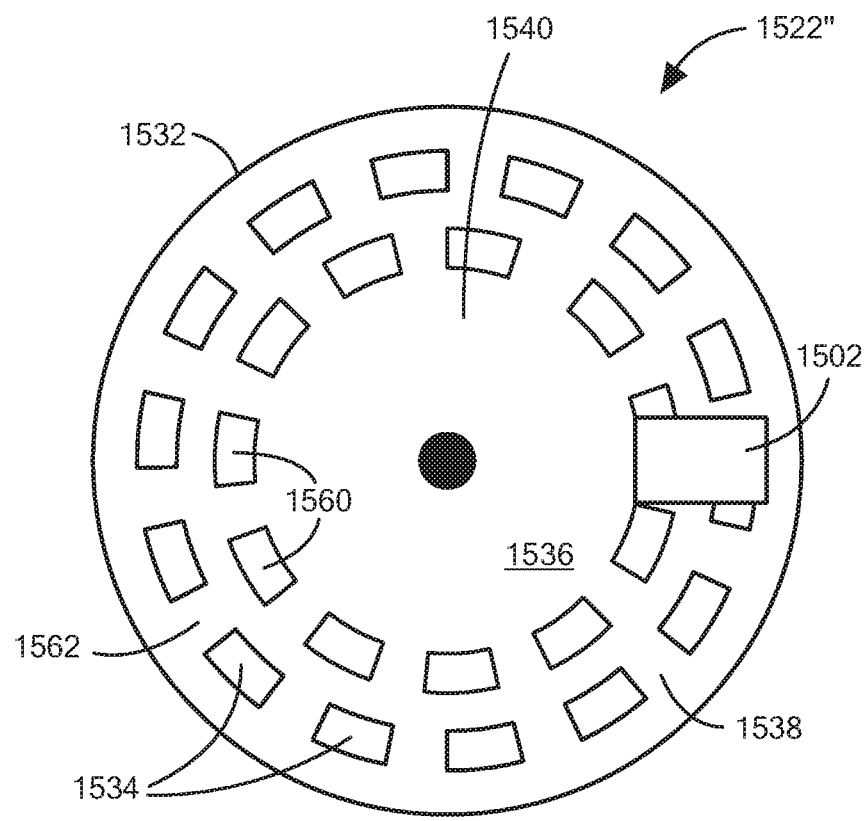
FIG. 15C is a side view of a magnetic field sensor and a magnetic target having material with multiple thicknesses.

Referring to FIG. 15C, system 1522" may include magnetic field sensor 1502 and rotational target 1532. Target 1532 may comprise one or more first material portions 1534' and a second material portion 1536. First material portions 1534 may be a high-conductivity material, such as a metal; and second material portion 1536 may be a relatively low-conductivity material, such as a plastic, ceramic, or other insulating material; or vice versa.

First material portions 1534' may comprise several series of discrete wells positioned in a spaced arrangement around different radial circumference of target 1532. First material portions 1530 may be spaced evenly, or according to any type of pattern. Accordingly, when magnetic field sensor 1502 is adjacent to one of the first material portions 1534, a reflected magnetic field will be produced and detected. When magnetic field sensor 1502 is adjacent to an insulating area (e.g. area 1538), a reflected magnetic field may not be produced by the insulating area 1538. Thus, the magnetic field sensing elements of magnetic field sensor 1502 may detect the reflected magnetic fields produced by first material portions 1534 and detect when no reflected magnetic field is produced by insulating areas 1538 as target 1532 rotates relative to magnetic field sensor 1502. The second radial series of wells may be arranged so that each well 1560 in the second radial series is placed adjacent to a gap 1562 between the wells 1534 in the first radial series. As magnetic field sensor 1502 detects each radial series, there may be a 90-degree shift of phase or a different pitch between detection of the first radial series of wells and the second radial series of wells, which may be used to increase the accuracy of angle by a Vernier type of approach.

Magnetic field sensor 1502 may be placed inside the outermost radius of target 1532, and adjacent to a substantially flat face 1540 of target 1532. In other words, if target 1532 is placed at the end of a rotating shaft, magnetic field sensor 1502 may be positioned adjacent to the face of one end of the shaft. Thus, as target 1532 rotates, the magnetic field sensing elements of magnetic field sensor 1502 may detect first material portions 1534 as they pass by.

Figure 16:
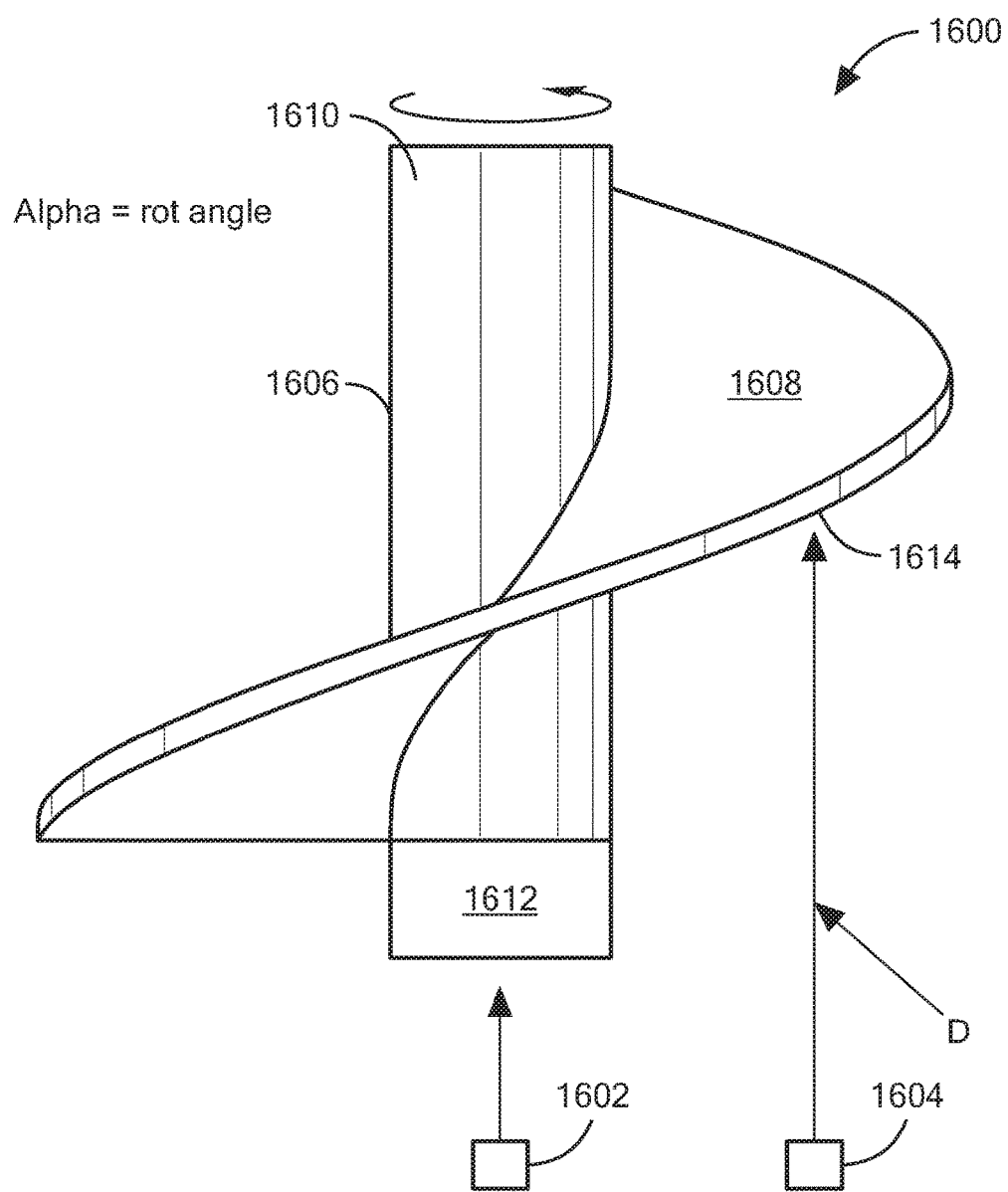
FIG. 16 is a side view of a magnetic field sensor and a magnetic target having an inclined plane.

Referring to FIG. 16, system 1600 may include a first magnetic field sensor 1602, a second magnetic field sensor 1604, and a rotating target 1606. Magnetic field sensors 1602 and 1604 may be the same as or similar to magnetic field sensor 100 and/or any of the magnetic field sensors described above.

Target 1606 may include a spiral inclined plane 1608 positioned around a central axis 1610. In embodiments, central axis 1610 may be a rotating shaft. Target 1606 may also include a conductive reference portion 1612. Reference portion 1612 and inclined plane 1608 may be formed from conductive material.

In an embodiment, magnetic field sensor 1602 is positioned adjacent to reference portion 1612. A coil of magnetic field sensor 1602 produces a magnetic field, which in turn produces eddy currents in reference portion 1612. Magnetic field sensor 1602 may detect the reflected magnetic field produced by the eddy currents.

Similarly, magnetic field sensor 1604 may be positioned relative to inclined plane 1608. A coil of magnetic field sensor 1608 may produce a magnetic field, which in turn may produce eddy currents in a portion 1614 of inclined plane adjacent to magnetic field sensor 1604. Magnetic field sensor 1604 may detect the reflected magnetic field produced by the eddy currents in inclined plane 1608.

As target 1606 rotates, the portion 1614 of inclined plane 1608 adjacent to magnetic field sensor 1604 will move toward and/or away from magnetic field sensor 1604. The proximity D of portion 1614 to magnetic field sensor 1604 can be detected by magnetic field sensor 1604. Processing circuitry (not shown) can correlate the proximity D to a rotational angle of target 1606 and determine position, speed of rotation, direction of rotation, etc.

Figure 16A:
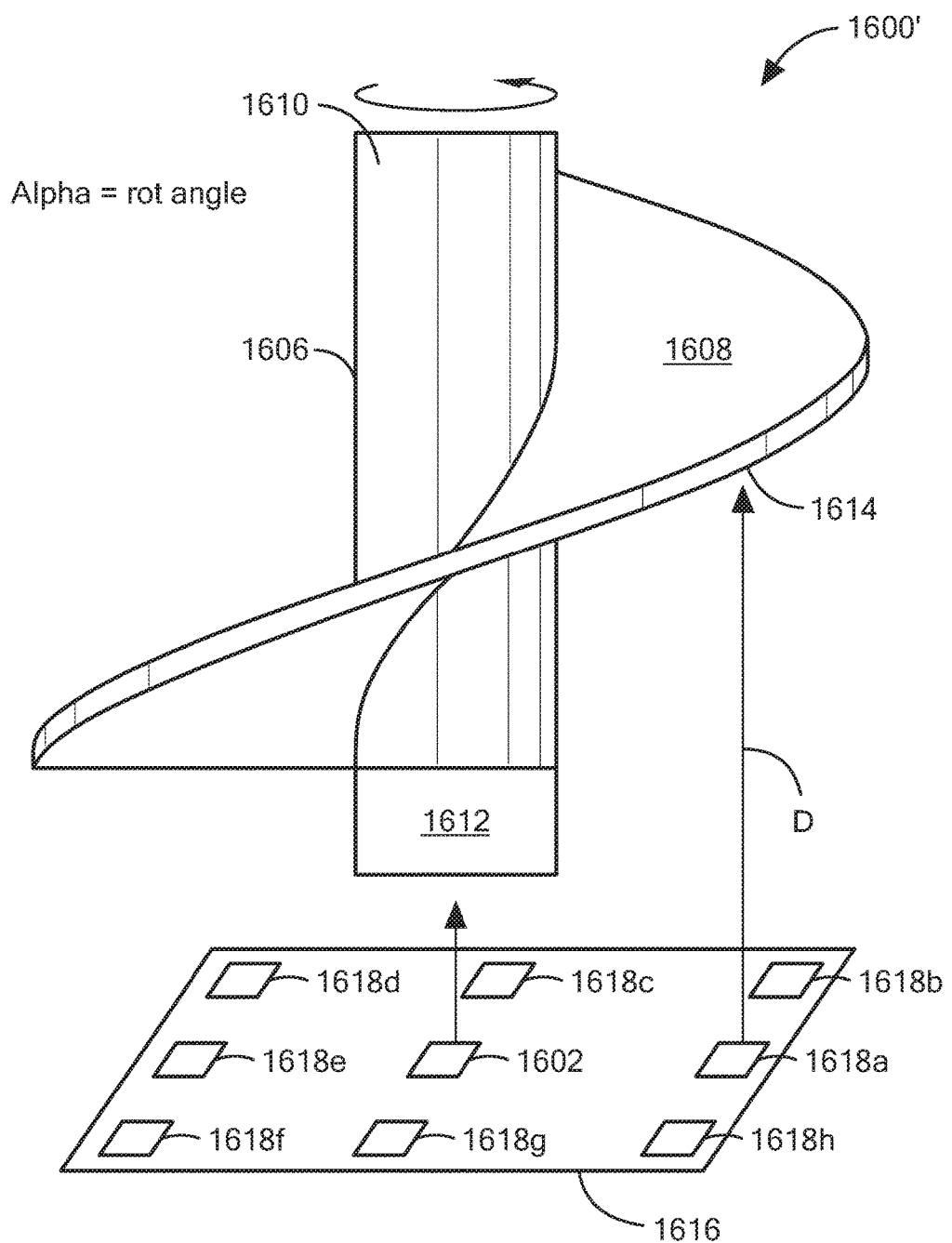
FIG. 16A is a side view of a magnetic field sensor and a magnetic target having an inclined plane.

Referring to FIG. 16A, system 1600' may include a grid of magnetic field sensors 1616, and a rotating target 1606.

Target 1606 may include a spiral inclined plane 1608 positioned around a central axis 1610. In embodiments, central axis 1610 may be a rotating shaft. Target 1606 may also include a conductive reference portion 1612. Reference portion 1612 and inclined plane 1608 may be formed from conductive material.

In an embodiment, magnetic field sensor 1602 of grid 1616 is positioned adjacent to reference portion 1612. A coil of magnetic field sensor 1602 produces a magnetic field, which in turn produces eddy currents in reference portion 1612. Magnetic field sensor 1602 may detect the reflected magnetic field produced by the eddy currents.

The other magnetic field sensors 1618a-h may be positioned in various locations on the grid 1616 relative to inclined plane 1608. A coil of each of magnetic field sensors 1618a-h may produce a magnetic field, which in turn may produce eddy currents in a portion of the inclined plane adjacent to each magnetic field sensor 1618a-h, which may each detect the local reflected magnetic field produced by the eddy currents in inclined plane 1608.

As target 1606 rotates, the portions of inclined plane 1608 adjacent to magnetic field sensors 1618a-h will move toward and/or away from magnetic field sensors 1618a-h. The proximity D of any portion 1614 to any magnetic field sensor 1618a-h can be detected by each magnetic field sensor. Processing circuitry (not shown) can correlate the proximity D to a rotational angle of target 1606 and determine position, speed of rotation, direction of rotation, etc.

Referring to FIG. 16A, a plurality of sensors 1618a-h forming a grid may be used to measure the distance of the spiral at different points so it allows to correct vibrations of the spiral on directions perpendicular to the axe of rotation whereas the central sensor of the grid is suppressing the vibrations along the axe of rotation.

Figure 17:
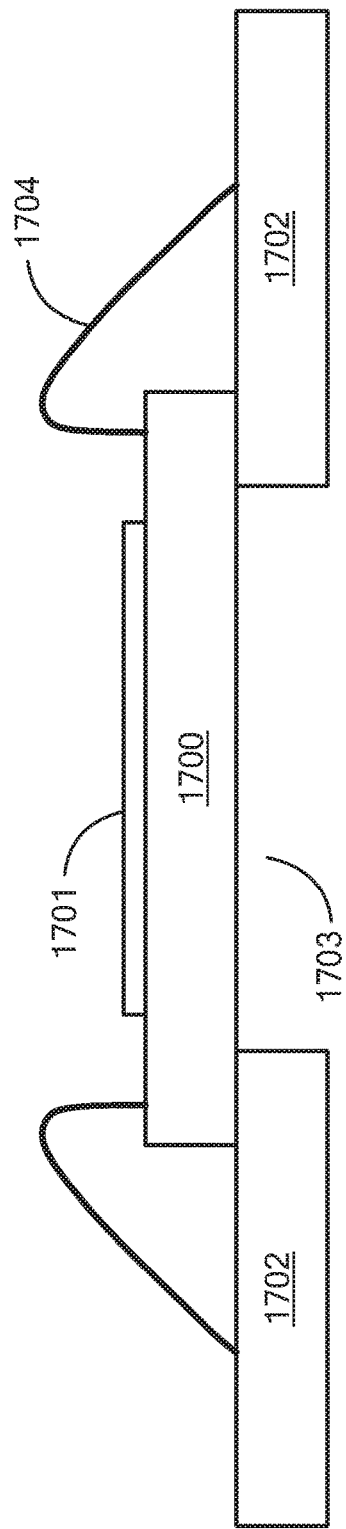
FIG. 17 is a side view of a substrate and lead frame connected by lead wires.

Referring to FIG. 17, a substrate 1700 may support one or more of the magnetic field sensor circuits described above, including coils and magnetic field sensing elements. Substrate 1700 may be positioned (and adhered to) frame 1702. Substrate 1700 may be a semiconductor substrate, a glass substrate, a ceramic substrate, or the like. Bond wires 1704 may electrically couple connection pads on substrate 1700 to leads of frame 1702. Frame 1702 may be a lead frame, a pad frame, or any structure that can support substrate 1700.

In embodiments, substrate 1700 may support coil 1701, which may be the same as or similar to the coils described above. Coil 1701 may produce a magnetic field that may induce eddy current and a reflected magnetic field in a target and/or a magnetic field that may be directly coupled to (e.g. directly detected by) MR elements. As shown, coil 1701 may be positioned adjacent to (or opposite) a gap 1703 in frame 1702. If frame 1702 is a conductive material (such as metal), the magnetic field produced by coil 1701 could induce eddy currents and a reflected field from frame 1702. Placing coil 1701 near gap 1703 may reduce or eliminate any unwanted reflected field that might otherwise by generated by frame 1702.

Figure 17A:
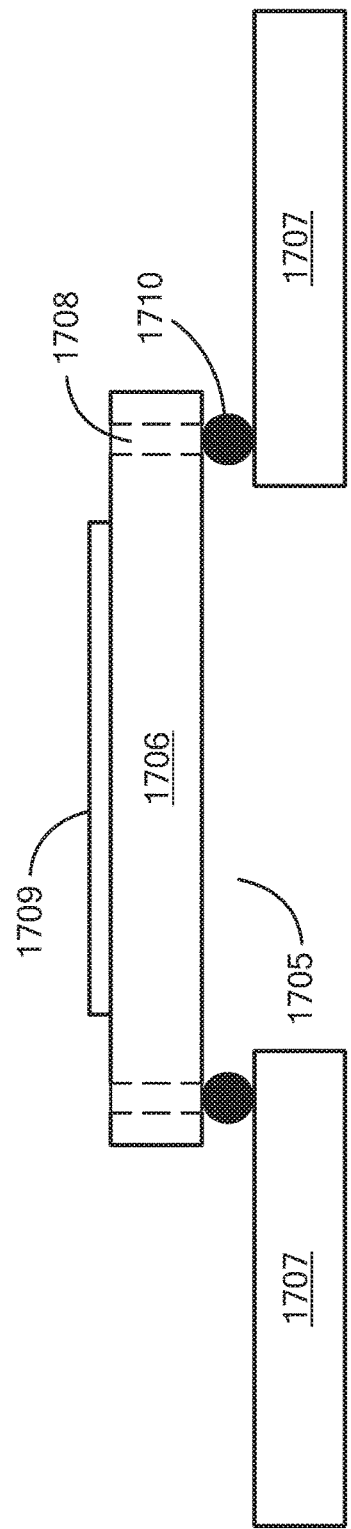
FIG. 17A is a side view of a substrate and lead frame connected by solder bumps.

In FIG. 17A, substrate 1706 may support one or more of the magnetic field sensor circuits described above, including coils and magnetic field sensing elements. Substrate 1706 may be positioned (and adhered to) lead frame 1707. Substrate 1706 may include one or more vias 1708, which may be coupled to solder balls (or solder bumps) 1710. Solder balls 1710 may be coupled to leads of lead frame 1707 to provide an electrical connection between vias 1708 and leads of lead frame 1707. The electrical connection may couple the sensor circuitry (generally supported by one surface of substrate 1700) to external system and components through leads 1707.

In embodiments, substrate 1706 may support coil 1709, which may be the same as or similar to the coils described above. Coil 1709 may produce a magnetic field that may induce eddy current and a reflected magnetic field in a target and/or a magnetic field that may be directly coupled to (e.g. directly detected by) MR elements. As shown, coil 1709 may be positioned adjacent to (or opposite) a gap 1705 in frame 1707. If frame 1707 is a conductive material (such as metal), the magnetic field produced by coil 1709 could induce eddy currents and a reflected field from frame 1707. Placing coil 1709 near gap 1705 may reduce or eliminate any unwanted reflected field that might otherwise by generated by frame 1707.

In embodiments, the grid of sensors 1608a-h in FIG. 16A may be formed on the surface of substrate 1700 or 1706.

Figure 18:
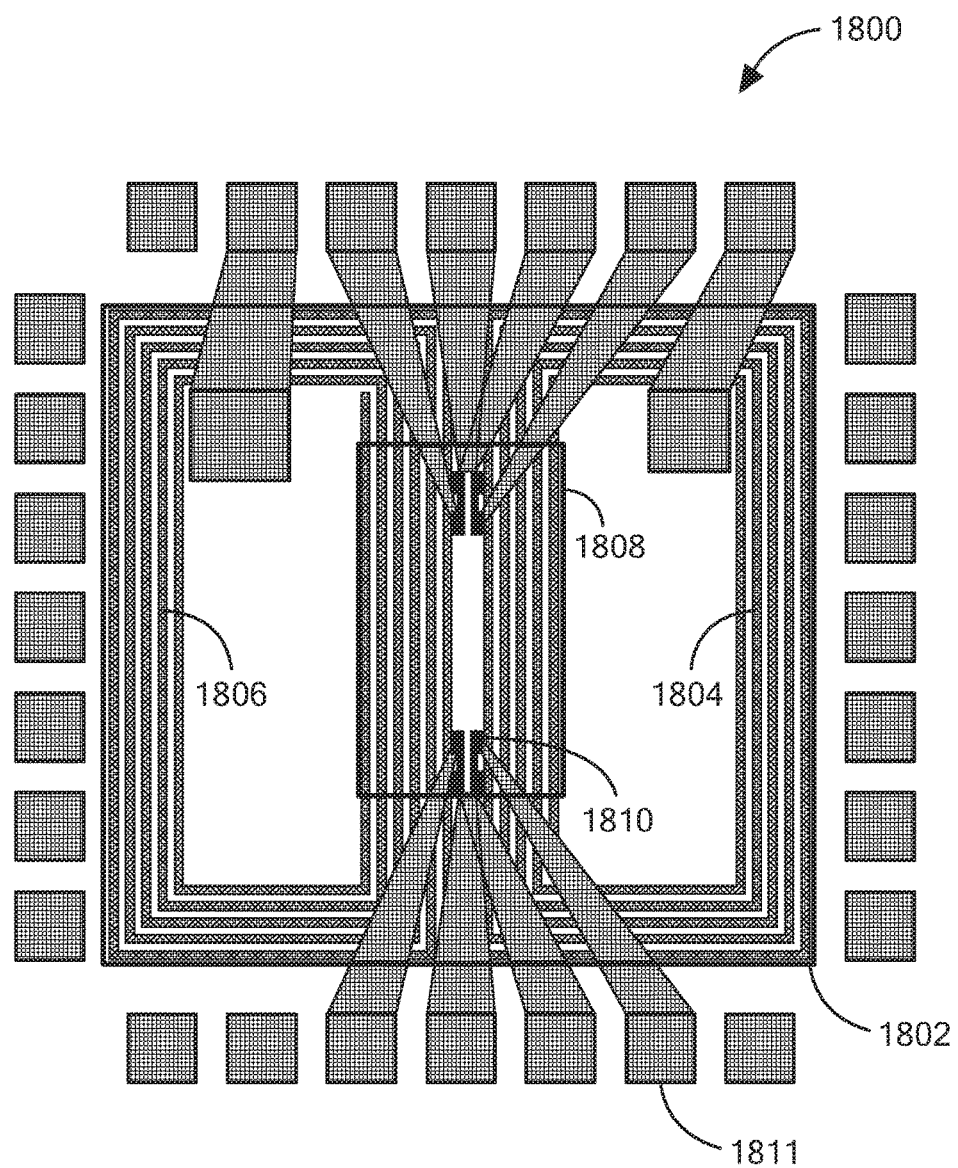
FIG. 18 is a schematic diagram of a dual-die package including one or more coils.

Referring to FIG. 18, a magnetic field sensor circuit 1800 may be supported by one or more substrates. As shown in FIG. 18, a first substrate 1802 may support one or more coils 1804, 1806, which may produce a magnetic field. A second substrate 1808 may support one or more magnetic field sensing elements 1810, which may detect the reflected magnetic field as discussed above. The semiconductor dies 1802, 1808 may also include additional circuitry discussed above. Circuits supported by substrate 1802 may be electrically coupled to circuits supported by substrate 1808 with lead wires (not shown). The supported circuits may also be coupled to leads of a frame 1811 by lead wires. A semiconductor package (not shown) may enclose the substrates.

In an embodiment, second die 1808 may be glued to a top surface of first die 1802. Alternatively, die 1808 may be reversed and electrically connected to die 1802 with die-to-die electrical connections.

The magnetic fields produced by coils 1804 and 1808 may cancel each other out in the area between coils 1804 and 1806, i.e. the area where MR elements 1810 are positioned. Thus, substrate 1808 may be positioned so that MR elements 1810 fall within the area where the magnetic fields cancel, to minimize any stray or directly coupled field detected by MR elements 1810.

In embodiments, substrates 1802 and 1808 may be different types of substrates. For example, substrate 1802 may be an inexpensive substrate for supporting metal traces such as coils 1804 and 1806, while substrate 1808 may be a substrate for supporting MR elements and/or other integrated circuits.

Figure 18A:
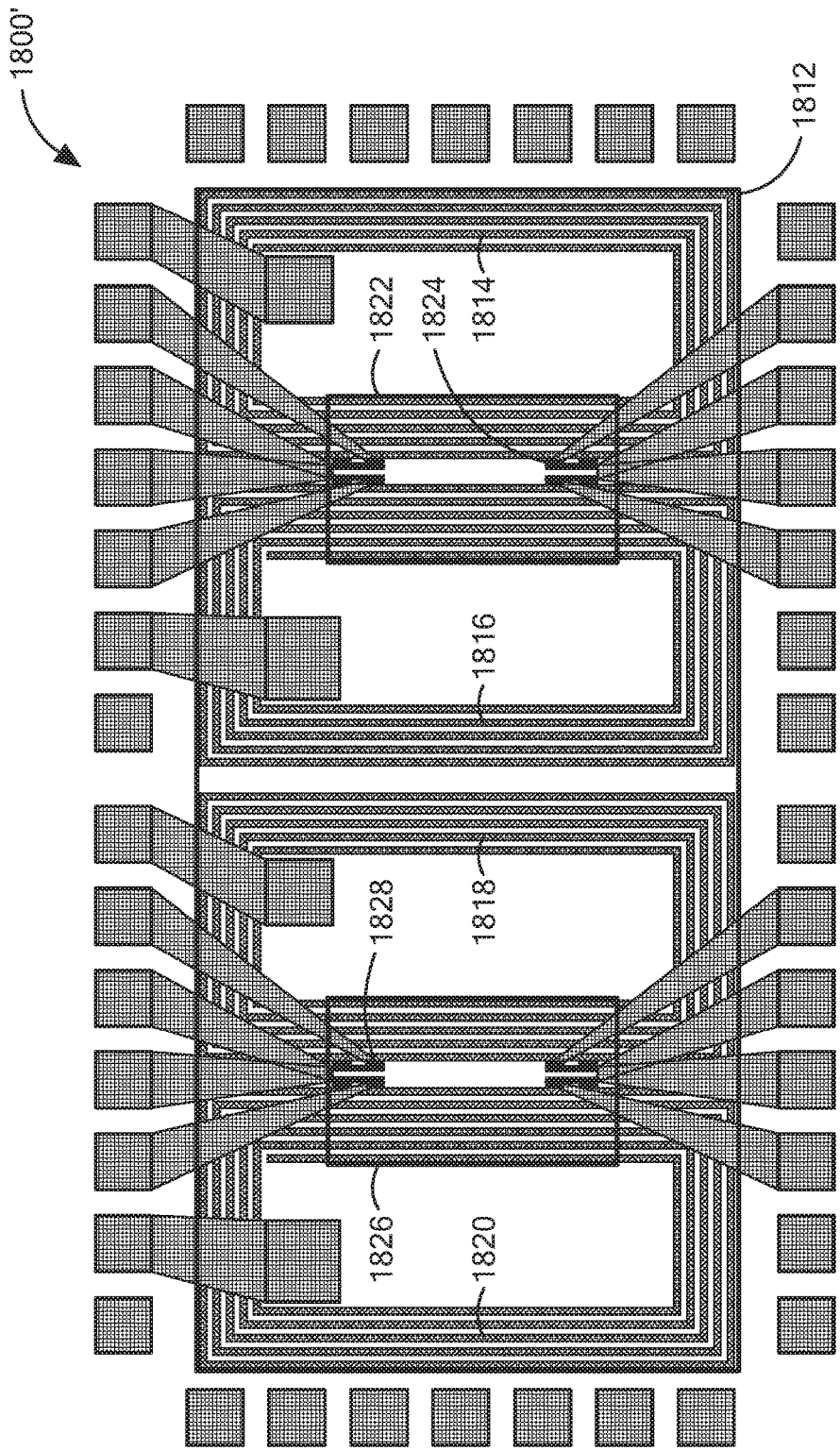
FIG. 18A is a schematic diagram of a dual-die package including one or more coils.

Referring to FIG. 18A, a magnetic field sensor circuit 1800' may be supported by multiple semiconductor dies. As shown, a first die 1812 may support two (or more) sets of coils. A first set of coils may include coils 1814 and 1816. A second set may include coils 1818 and 1820. A second die 1822 may support a first set of magnetic field sensing elements 1824, and a third die 1826 may support a second set of magnetic field sensing elements 1828.

In an embodiment, magnetic field sensor circuit 1800' may include two magnetic field sensors. The first sensor may include coils 1814 and 1816, die 1822, and magnetic field sensing elements 1824. The second magnetic field sensor may include coils 1818 and 1820, die 1826, and magnetic field sensing elements 1828. In other embodiments, magnetic field sensor circuit 1800' may include additional magnetic field sensors comprising additional coils, dies, and magnetic field sensing elements.

Magnetic field sensor circuit 1800' may be used in any of the systems described above that employ two (or more) magnetic field sensors. Additionally or alternatively, the two magnetic field sensors in circuit 1800' may be driven at different frequencies to avoid cross-talk between the two sensors.

Figure 19:
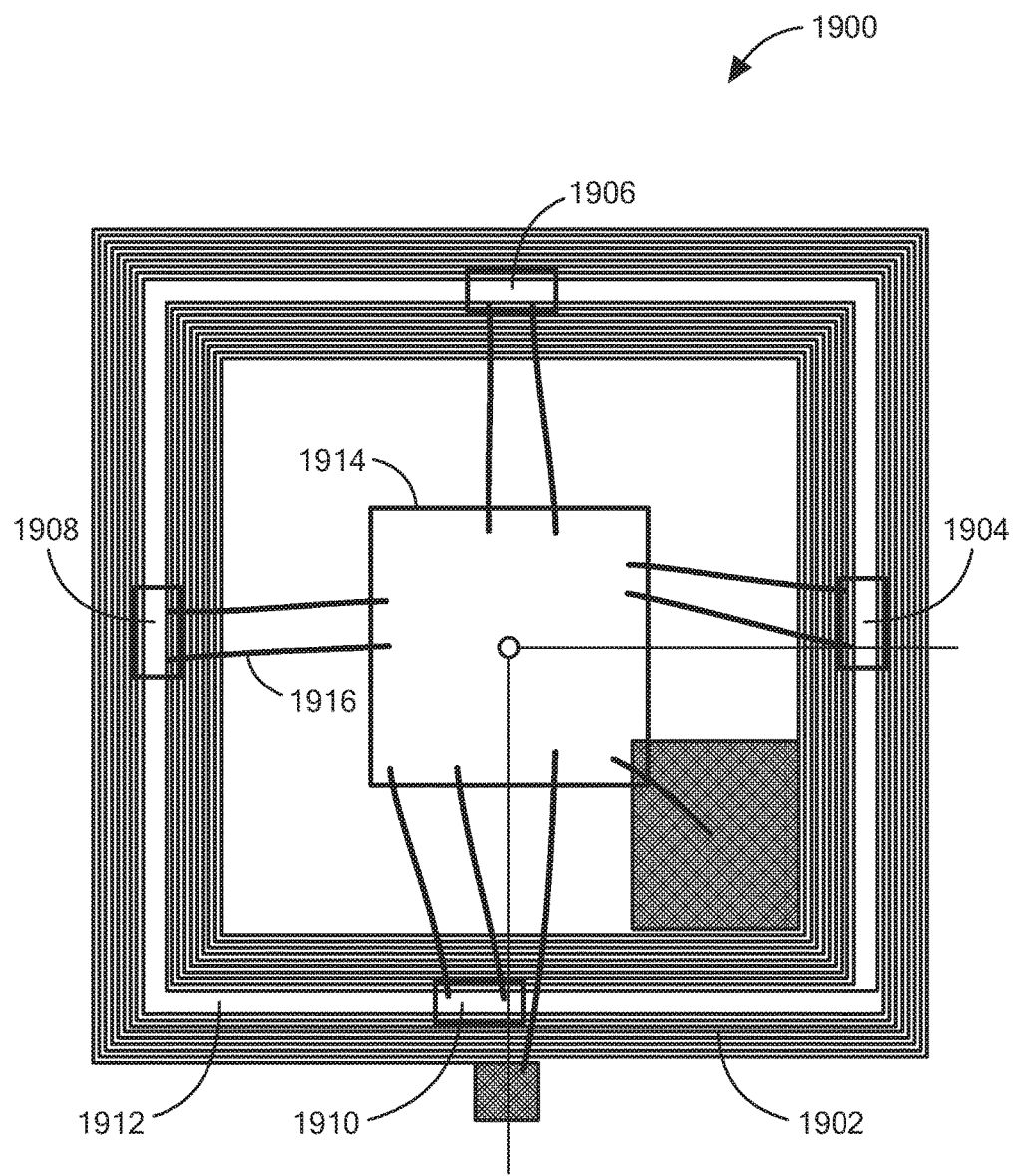
FIG. 19 is a schematic diagram of a multi-die package including one or more coils.

Referring to FIG. 19, a magnetic field sensor circuit 1900 may be supported by multiple substrates. A first substrate may support coil 1902. Four smaller substrates 1904-1910 may each support one or more magnetic field sensing elements. As shown, substrates 1904-1910 may be positioned adjacent to traces of coil 1902. In some embodiments, substrates 1904-1910 may be positioned so the magnetic field sensing elements they support are placed adjacent to gap 1912 between traces of coil 1902.

A fifth substrate 1914 may support circuitry to drive coil 1902 and the magnetic field sensing elements, as well as processing circuitry to process signals received from the magnetic field sensing elements. Circuits on the various die may be coupled together by lead wires 1916.

Although not shown, in another embodiment, the larger substrate 1402 may support the coils and MR elements. The smaller substrate 1904-1908 may support circuitry to drive the coils and MR elements and/or circuits to process the magnetic field signals.

In an embodiment, the magnetic field sensing elements and coil 1902 may be the same as or similar to the magnetic field sensing elements (e.g. MR elements) and coils described in some or all of the magnetic field detection systems described above.

Having described preferred embodiments, which serve to illustrate various concepts, structures and techniques, which are the subject of this patent, it will now become apparent to those of ordinary skill in the art that other embodiments incorporating these concepts, structures and techniques may be used. Accordingly, it is submitted that that scope of the patent should not be limited to the described embodiments but rather should be limited only by the spirit and scope of the following claims. All references cited herein are hereby incorporated herein by reference in their entirety.

The invention claimed is:

1. An apparatus comprising:
   one or more substrates;
   one or more coil supported by at least one of the one or more substrates, at least one of the coils configured to produce a first magnetic field that induces eddy currents in a conductive target that generates a reflected magnetic field;
   one or more magnetic field sensing elements supported by the one or more substrates to detect the reflected magnetic field; and
   a conductive support structure to support the one or more substrates, the support structure having a gap in an area adjacent to the one or more coils so that the support structure does not generate a reflected magnetic field in response to the first magnetic field.

2. The apparatus of claim 1 wherein the one or more magnetic field sensing elements are arranged in a grid pattern on the one or more substrates.

3. The apparatus of claim 1 wherein at least one of the coils comprises a plurality of traces and wherein the one or more magnetic field sensing elements are positioned on the substrate in a space between traces of the coil.

4. The apparatus of claim 1 wherein the coil includes a counter coil to produce a local magnetic field in a direction opposite to the direction of the first magnetic field.

5. The apparatus of claim 4 wherein at least one of the coils comprises a plurality of traces and wherein the one or more magnetic field sensing elements are positioned in a space between one or more traces of the counter coil.

6. The apparatus of claim 1 wherein the one or more substrates comprise one or more of: a semiconductor material, a glass material, or a ceramic material.

7. The apparatus of claim 1 wherein a first substrate of the one or more substrates supports the one or more coils and one or more second substrates of the one or more substrates support the one or more magnetic field sensing elements.

8. The apparatus of claim 7 wherein a third substrate of the one or more substrates supports a processing circuit.

9. The apparatus of claim 7 wherein the first substrate supports two or more coils.

10. The apparatus of claim 1 wherein the first substrate supports one or more coils and one or more magnetic field sensing elements.

11. The apparatus of claim 10 wherein the second one or more substrates support one or more processing circuits.

12. The apparatus of claim 1 wherein each of the magnetic field sensing elements is supported by a different substrate.

13. The apparatus of claim 1 wherein the substrates, coils, and magnetic field sensing elements form one or more magnetic field sensors.

14. The apparatus of claim 1 further comprising an adhesive to adhere at least two of the one or more substrates to each other.

15. The apparatus of claim 1 wherein the conductive support structure comprises a lead frame or a pad frame.

* * * * *